(12) United States Patent
Maruyama et al.

(10) Patent No.: US 8,344,154 B2
(45) Date of Patent: Jan. 1, 2013

(54) 2-THIOETHENYL SUBSTITUTED CARBAPENEM DERIVATIVES

(75) Inventors: Takahisa Maruyama, Yokohama (JP); Yuko Kano, Yokohama (JP); Takashi Ando, Yokohama (JP); Toshiro Sasaki, Yokohama (JP); Kazuhiro Aihara, Yokohama (JP); Toshiki Fujita, Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 204 days.

(21) Appl. No.: 12/656,606

(22) Filed: Feb. 4, 2010

(65) Prior Publication Data

US 2010/0145063 A1 Jun. 10, 2010

Related U.S. Application Data

(62) Division of application No. 11/401,892, filed on Apr. 12, 2006, now Pat. No. 7,687,490.

(60) Provisional application No. 60/673,892, filed on Apr. 22, 2005, provisional application No. 60/710,157, filed on Aug. 23, 2005.

(30) Foreign Application Priority Data

Apr. 12, 2005 (JP) ................... 2005-114690
Aug. 16, 2005 (JP) ................... 2005-235590

(51) Int. Cl.
 *C07D 277/24* (2006.01)
 *C07D 277/26* (2006.01)
(52) U.S. Cl. ......... 548/203; 548/110; 548/204; 548/205
(58) Field of Classification Search .................. 548/203, 548/204, 205
See application file for complete search history.

(56) References Cited

U.S. PATENT DOCUMENTS

| | | | |
|---|---|---|---|
| 4,413,000 A | 11/1983 | Eglington | |
| 4,477,662 A | 10/1984 | Corbett et al. | |
| 4,985,555 A * | 1/1991 | Takaya et al. | 540/229 |
| 5,395,845 A | 3/1995 | Benoit et al. | |
| 2003/0114478 A1* | 6/2003 | Guay et al. | 514/300 |

FOREIGN PATENT DOCUMENTS

| | | |
|---|---|---|
| JP | 06-025196 | 2/1994 |
| JP | 08-012676 | 1/1996 |
| JP | 09-249667 | 9/1997 |
| JP | 2002-332288 | 11/2002 |
| WO | 97/25325 | 7/1997 |
| WO | 03/089431 | 10/2003 |
| WO | 2004/067532 | 8/2004 |

OTHER PUBLICATIONS

An English translation of JP 2002/332288, 2002.*
Chinese Office Action (with English translation) issued Jan. 8, 2010 in corresponding Chinese Patent Application No. 200680020785.2.
Supplementary European Search Report issued Dec. 1, 2009 in corresponding European Patent Application No. 06 731 645.5.
Yokoo, C. et al., "Synthesis, Antibacterial Activity and Oral Absorption of New 3-(2-Substituted-Vinylthio)-7B-[(Z)-2-(2-Aminothiazol-4-yl)-2(Carboxymethoxyimino)Acetamido]Cephalosporins", The Journal of Antibiotics, Dec. 1991, pp. 1422-1431.
Nishimura, S. et al., "Synthesis and Biological Activity of 3-Vinylthio-and 3-Vinylthiomethylcephem Derivatives", The Journal of Antibiotics, Sep. 1990, pp. 1160-1168.

* cited by examiner

*Primary Examiner* — Laura L. Stockton
(74) *Attorney, Agent, or Firm* — Wenderoth, Lind & Ponack, L.L.P.

(57) ABSTRACT

2-Ethenylthio-type carbapenem derivatives of formula (I) or pharmaceutically acceptable salts thereof are provided. The compounds according to the present invention have potent antimicrobial activity and a wide antimicrobial spectrum against pneumococci including penicillin resistant *Streptococcus pneumoniae* (PRSP), *Haemophilus influenzae* including β-lactamase-negative, ampicillin-resistant *Haemophilus influenzae* (BLNAR), and *Moraxella* (*Branhamella*) *catarrhalis*.

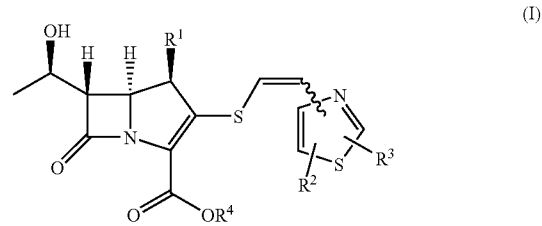

(I)

6 Claims, No Drawings

2-THIOETHENYL SUBSTITUTED CARBAPENEM DERIVATIVES

CROSS-REFERENCE TO RELATED APPLICATIONS

This application is a Divisional of U.S. application Ser. No. 11/401,892, filed Apr. 12, 2006 now U.S. Pat. No. 7,687,490, which claims the benefit of U.S. Provisional Application No. 60/673,892, filed Apr. 22, 2005 and U.S. Provisional Application No. 60/710,157, filed Aug. 23, 2005), and is based upon and claims the benefit of priority from prior Japanese Patent Application No. 114690/2005, filed Apr. 12, 2005 and prior Japanese Patent Application No. 235590/2005, filed Aug. 16, 2005, the entire contents of which are incorporated herein by reference.

BACKGROUND OF THE INVENTION

1. Field of the Invention

The present invention relates to carbapenem compounds which have excellent antimicrobial activity and a broad antimicrobial spectrum. More particularly, the present invention relates to novel carbapenem derivatives having a thioethenylthiazole group at the 2-position on the carbapenem ring.

2. Background Art

Carbapenem derivatives have potent antimicrobial activity and an excellent broad antimicrobial spectrum and thus have been energetically studied as a highly useful β-lactam agent, and Imipenem, Panipenem, Meropenem, and Biapenem have already been clinically used.

A group of compounds using various linking modes at the 2-position of the carbapenem ring have been studied (Expert Opinion Therapeutic Patents, (England), 2001, 11(8), pp. 1267-1276). Among others, a group of compounds having a heterocyclic ring at the 2-position of the carbapenem ring through a sulfur atom have been studied.

Further, for example, Japanese Patent Laid-Open No. 40487/1982 discloses compounds having a hydrogen atom at the 1-position of the carbapenem ring and a thioethenyltetrazole group at the 2-position of the carbapenem ring. Japanese Patent Laid-Open No. 12675/1996 and Japanese Patent Laid-Open No. 12676/1996 disclose compounds having methyl at the 1-position on the carbapenem ring (sometimes called "1β-methyl") and a thioalkenylenehalophenyl or thioalkenylenepyridyl group at the 2-position on the carbapenem ring. Furthermore, Japanese Patent Laid-Open No. 279888/1989 discloses compounds having methyl at the 5-position on the carbapenem ring and having a side chain through a sulfur atom at the 2-position on the carbapenem ring.

All the above publications, however, neither disclose nor suggest compounds having a thioethenylthiazole group at the 2-position of the carbapenem ring.

Japanese Patent Laid-Open No. 332288/2002 discloses cephalosporin compounds having thioethenylthiazole. This publication, however, neither discloses nor suggests antimicrobial activity against pneumococci including penicillin resistant Streptococcus pneumoniae (hereinafter often abbreviated to "PRSP"), Haemophilus influenzae including β-lactamase-negative, ampicillin-resistant Haemophilus influenzae (hereinafter often abbreviated to "BLNAR"), Moraxella (Branhamella) catarrhalis, and resistant Pseudomonas aeruginosa which currently pose clinical problems.

Further, Japanese Patent Laid-Open No. 332288/2002 describes 4-tritylthioethenylthiazole having methyl at the 4-position of the thiazole ring. However, any thiazole having other substituent is not disclosed. Further, the production process of this compound is different from that of the present invention. Furthermore, in the same publication, although 5-ethynyl-4-methylthiazole is disclosed, any thiazole having other substituent is not disclosed.

It is hard to say that the above compounds have satisfactory antimicrobial activity against methicillin resistant Staphylococcus aureus (MRSA), vancomycin resistant Enterococcus, penicillin resistant Streptococcus pneumoniae (PRSP), β-lactamase-negative, ampicillin-resistant Haemophilus influenzae (BLNAR), and resistant Pseudomonas aeruginosa which currently pose serious clinical problems. Thus, any satisfactory medicament has not been developed.

The carbapenem derivatives and cephalosporin derivatives disclosed in the above prior art documents are not always satisfactory in terms of antimicrobial activity against bacteria including various resistant bacteria. Accordingly, the development of compounds having satisfactory activity against various resistant bacteria and infectious disease causing bacteria has still been desired.

SUMMARY OF THE INVENTION

The present inventors have now found that novel carbapenem derivatives represented by formula (I) have a broad spectrum of and potent anitimicrobial activity against Gram positive and Gram negative bacteria. These derivatives had potent antimicrobial activity against Haemophilus influenzae, Moraxella (Branhamella) catarrhalis, and β-lactamase producing bacteria. Further, compounds of formula (I) could be produced efficiently by using compounds of formula (III) and compounds of formula (IV) as an intermediate. The present invention has been made based on such finding.

An object of the present invention is to provide carbapenem derivatives having excellent antimicrobial activity and a broad antimicrobial spectrum. More particularly, an object of the present invention is to provide carbapanem derivatives having potent antimicrobial activity and a broad microbial spectrum against infectious disease causing bacteria, particularly against pneumococci including PRSP, Haemophilus influenzae including BLNAR, Moraxella (Branhamella) catarrhalis, and β-lactamase producing bacteria.

According to the present invention, there are provided compounds represented by formula (I) and pharmaceutically acceptable salts thereof:

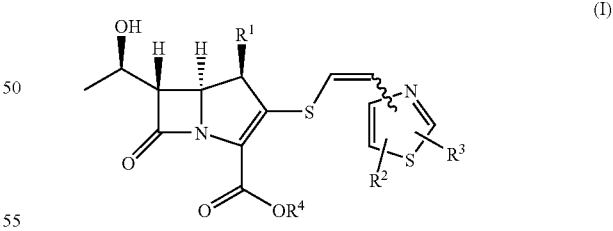

(I)

wherein
R$^1$ represents a hydrogen atom or methyl,
R$^2$ and R$^3$, which may be the same or different, each represent
 a hydrogen atom,
 a halogen atom,
 amino,
 substituted amino,
 lower alkyl,
 substituted lower alkyl,
 carbamoyl, substituted aminocarbonyl,
lower alkoxycarbonyl,
substituted lower alkoxycarbonyl,
heterocyclic carbonyl, or
substituted heterocyclic carbonyl, and
$R^4$ represents a hydrogen atom or a biohydrolyzable group.

In a preferred embodiment of the present invention, the compounds represented by formula (I) are compounds represented by formula (II):

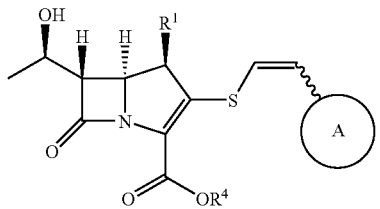

(II)

wherein
$R^1$ represents a hydrogen atom or methyl,
ring A represents
4-hydroxymethylthiazole,
5-hydroxymethylthiazole,
4-(2-hydroxyethoxy)methylthiazole,
4-N,N-dimethylcarbamoylthiazole,
2-N,N-dimethylcarbamoylthiazole,
4-methylthiazole,
4-carbamoylthiazole,
2-carbamoylthiazole,
4-N-methylcarbamoylthiazole,
4-N-cyanomethyl-N-methylcarbamoylthiazole,
4-N-cyanomethylcarbamoylthiazole,
4-N-(2-cyanoethyl)carbamoylthiazole,
4-cyanomethylthiazole,
4-(2-methoxyethoxy)methylthiazole,
4-(3-cyanoazetidin-1-yl)carbonylthiazole,
4-N-(2-hydroxyethyl)carbamoylthiazole,
4-N-(3-hydroxypropan-1-yl)carbamoylthiazole,
4-N-(2-hydroxyethyl)-N-methylcarbamoylthiazole,
4-(azetidin-1-yl)carbonylthiazole,
4-(3-hydroxyazetidin-1-yl)carbonylthiazole,
4-(3-hydroxypropan-1-yloxy)methylthiazole,
2-amino-4-carbamoylthiazole,
2-aminothiazole,
4,5-dicarbamoylthiazole,
4-acetoxymethylthiazole,
4-(2-acetoxyethoxy)methylthiazole,
4-(L-valyloxymethyl)thiazole,
4-methoxycarbonylthiazole,
4-ethoxycarbonylthiazole,
2-amino-4-methoxycarbonylthiazole, or
2-amino-4-ethoxycarbonylthiazole, and
$R^4$ represents a hydrogen atom or a biohydrolyzable group.

According to another aspect of the present invention, there are provided compounds represented by formula (III) or pharmaceutically acceptable salts thereof as synthetic intermediates of the compounds represented by formula (I):

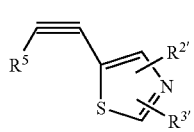

(III)

wherein
one of $R^{2'}$ and $R^{3'}$ represents
hydroxy lower alkyl,
hydroxy lower alkyl protected by a protective group of hydroxyl,
lower alkoxy-lower alkyl, or
lower alkoxycarbonyl, and
the other represents a hydrogen atom, and
$R^5$ represents a hydrogen atom or a protective group of alkynyl.

According to still another aspect of the present invention, there are provided compounds represented by formula (IV) or pharmaceutically acceptable salts thereof as synthetic intermediates of the compounds of formula (I):

(IV)

wherein
$R^{2'}$ and $R^{3'}$, which may be the same or different, each represent
a hydrogen atom,
a halogen atom,
amino,
substituted amino,
hydroxy lower alkyl,
cyano lower alkyl,
lower alkoxy-lower alkyl,
substituted lower alkoxy-lower alkyl,
lower alkoxy-lower alkoxy-lower alkyl,
substituted lower alkoxy-lower alkoxy-lower alkyl,
acyloxy lower alkyl,
substituted acyloxy lower alkyl,
carbamoyl,
mono-lower alkylcarbamoyl,
substituted mono-lower alkylcarbamoyl,
di-lower alkylcarbamoyl,
substituted di-lower alkylcarbamoyl,
lower alkoxycarbonyl,
azetidinylcarbonyl, or
substituted azetidinylcarbonyl, and
$R^6$ represents $$R^7-S-C\equiv C-$$

wherein $R^7$ represents a hydrogen atom, a metal ion, or a protective group of thiol.

According to a further aspect of the present invention, there is provided a process for producing a compound of formula (I). This process is characterized by comprising reacting a compound of formula (V) with a compound of formula (IVc):

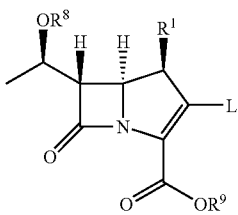
(V)

wherein
$R^1$ represents a hydrogen atom or methyl,
$R^8$ represents a hydrogen atom or a protective group of hydroxyl,
$R^9$ represents a protective group of carboxyl, and
L represents a leaving group; and

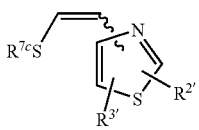
(IVc)

wherein
$R^{7c}$ represents a metal ion and
$R^{2'}$ and $R^{3'}$, which may be the same or different, each represent
  a hydrogen atom,
  a halogen atom,
  amino,
  substituted amino,
  hydroxy lower alkyl,
  cyano lower alkyl,
  lower alkoxy-lower alkyl,
  substituted lower alkoxy-lower alkyl,
  lower alkoxy-lower alkoxy-lower alkyl,
  substituted lower alkoxy-lower alkoxy-lower alkyl,
  acyloxy lower alkyl,
  substituted acyloxy lower alkyl,
  carbamoyl,
  mono-lower alkylcarbamoyl,
  substituted mono-lower alkylcarbamoyl,
  di-lower alkylcarbamoyl,
  substituted di-lower alkylcarbamoyl,
  lower alkoxycarbonyl,
  azetidinylcarbonyl, or
  substituted azetidinylcarbonyl.

In a preferred embodiment of the present invention, the process for producing compounds represented by formula (I) further comprises reacting a compound of formula (III) with a corresponding thiol represented by formula $R^{7b}SH$ to give the compound of formula (IVc):

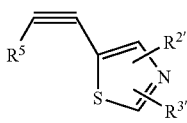
(III)

wherein
one of $R^{2'}$ and $R^{3'}$ represents
  hydroxy lower alkyl,
  hydroxy lower alkyl protected by a protective group of hydroxyl,
  lower alkoxy-lower alkyl, or
  lower alkoxycarbonyl, and
the other represents a hydrogen atom, and
$R^5$ represents a hydrogen atom or a protective group of alkynyl, and
wherein $R^{7b}$ in the corresponding thiol represents a group selected from the group consisting of triphenylmethyl, diphenylmethyl, acyl protective groups, optionally substituted benzyl, and silyl protective groups.

According to the present invention, there is provided a pharmaceutical composition comprising a compound of formula (I) or a pharmaceutically acceptable salt thereof according to the present invention. Preferably, the pharmaceutical composition comprises a compound of formula (I) or a pharmaceutically acceptable salt thereof according to the present invention and a pharmaceutically acceptable carrier. More preferably, this pharmaceutical composition is used as an antimicrobial agent.

According to another aspect of the present invention, there is provided a method for treating or preventing a bacterial infectious disease or a symptom related thereto, comprising the step of administering an effective amount of a compound of formula (I) or a pharmaceutically acceptable salt thereof according to the present invention to a patient requiring such treatment or prevention. Preferably, bacteria involved in the bacterial infectious disease are selected from the group consisting of pneumococci, *Haemophilus influenzae, Moraxella (Branhamella) catarrhalis*, and β-lactamase producing bacteria.

According to a further aspect of the present invention, there is provided use of a compound of formula (I) or a pharmaceutically acceptable salt thereof according to the present invention, for the manufacture of medicaments for treating or preventing bacterial infectious diseases or symptoms related thereto.

The carbapenem derivatives represented by formula (I) according to the present invention have potent antimicrobial activity against a wide spectrum of Gram positive and Gram negative bacteria, particularly against various bacteria, for example, pneumococci including PRSP, *Haemophilus influenzae* including BLNAR, *Moraxella (Branhamella) catarrhalis*, and β-lactamase producing bacteria. Among the compounds represented by formula (I) according to the present invention, carbapenem derivatives represented by formula (I), wherein $R^4$ represents a biohydrolyzable group, have oral absorptivity, are metabolically deesterified in vivo to produce an original substance (a compound of formula (I')) having antimicrobial activity. Accordingly, the compounds represented by formula (I) according to the present invention is useful as injections, and, at the same time, the ester thereof is also useful as oral preparations. Further, the carbapenem derivatives according to the present invention are low in toxicity and thus are highly safe.

DETAILED DESCRIPTION OF THE INVENTION

Definition

The term "lower alkyl" and the term "lower alkoxy" as used herein as a group or a part of a group respectively mean straight chain or branched chain alkyl and alkoxy having 1 to 6, preferably 1 to 4 carbon atoms.

Examples of "lower alkyl" as a group or a part of a group include methyl, ethyl, n-propyl, isopropyl, n-butyl, i-butyl, s-butyl, t-butyl, n-pentyl, neopentyl, i-pentyl, t-pentyl, n-hexyl, and i-hexyl.

Examples of "lower alkoxy" as a group or a part of a group include methoxy, ethoxy, n-propoxy, i-propoxy, n-butoxy, s-butoxy, t-butoxy, n-pentyloxy, neopentyloxy, i-pentyloxy, t-pentyloxy, n-hexyloxy, and i-hexyloxy.

The term "lower cycloalkyl" as used herein as a group or a part of a group means monocyclic alkyl having 3 to 6 carbon atoms, and examples thereof include cyclopropyl, cyclobutyl, cyclopentyl, and cyclohexyl.

Examples of "acyl" as a group or a part of a group include formyl, acetyl, propionyl, butyryl, pivaloyl, isobutyryl, valeryl, benzoyl, phthaloyl, arylcarbonyl, and heterocyclic carbonyl.

The term "halogen atom" means a fluorine, chlorine, bromine, or iodine atom. Preferably, the halogen atom is a chlorine or bromine atom.

The term "aryl" as used herein as a group or a part of a group means phenyl or naphthyl.

The term "heterocyclic ring" as used herein as a group or a part of a group means a four- to seven-membered, preferably five- or six-membered, heterocyclic ring having one or a plurality of heteroatoms, which may be the same or different, selected from the group consisting of nitrogen, oxygen, and sulfur. Preferred heterocyclic rings include furan, pyrrole, imidazole, pyrazole, thiazole, triazole, thiadiazole pyridine, pyrazine, pyridazine, pyrimidine, isoxazole, thiophene, azetidine, pyrrolidine, piperidine, piperazine, morpholine, thiomorpholine, and thiazoline. More preferred are furan, thiophene, imidazole, thiazole, pyridine, pyrimidine, azetidine, pyrrolidine, piperidine, piperazine, morpholine, and thiazoline.

Compounds $R^1$ represents a hydrogen atom or methyl. In one preferred embodiment of the present invention, $R^1$ represents methyl.

$R^2$ and $R^3$, and $R^{2'}$ and $R^{3'}$, which may be the same or different, represent a hydrogen atom, a halogen atom, amino, substituted amino, lower alkyl, substituted lower alkyl, carbamoyl, substituted aminocarbonyl, lower alkoxycarbonyl, substituted lower alkoxycarbonyl, heterocyclic carbonyl, or substituted heterocyclic carbonyl.

Substituents for amino in "substituted amino" and "substituted aminocarbonyl" include lower alkyl, lower cycloalkyl, lower alkoxy, lower alkoxyalkyl, lower alkylcarbonyl, lower alkoxycarbonyl, formyl, aminocarbonyl, aminosulfonyl, lower alkylcarbamoyl, hydroxy lower alkyl, amino lower alkyl, aryl, or heteroaryl.

Substituents for "lower alkyl," or "lower alkyl" as a part of a group in "substituted lower alkyl," "substituted lower alkoxycarbonyl," "substituted lower alkoxycarbonyl," "substituted lower alkoxy-lower alkyl," "substituted lower alkoxy-lower alkoxy-lower alkyl," "substituted mono-lower alkylcarbamoyl," and "substituted di-lower alkylcarbamoyl" include hydroxyl, lower alkoxy, lower alkylthio, amino, aryl, heterocyclic group, carbamoyl, lower alkylaminocarbonyl, formylamino, lower alkylcarbonylamino, aminosulfonylamino, or aminocarbonylamino.

Substituents for the heterocyclic ring in "substituted heterocyclic carbonyl" include hydroxyl, amino, lower alkyl, or lower alkoxy.

Preferred groups indicated by $R^2$ and $R^3$, and $R^{2'}$ and $R^{3'}$ include a hydrogen atom, a halogen atom, amino, substituted amino, lower alkyl, hydroxy lower alkyl, hydroxy lower alkyl protected by a protective group of hydroxyl, cyano lower alkyl, lower alkoxy-lower alkyl, substituted lower alkoxy-lower alkyl, lower alkoxy-lower alkoxy-lower alkyl, substituted lower alkoxy-lower alkoxy-lower alkyl, acyloxy lower alkyl, substituted acyloxy lower alkyl, carbamoyl, mono-lower alkylcarbamoyl, substituted mono-lower alkylcarbamoyl, di-lower alkylcarbamoyl, substituted di-lower alkylcarbamoyl, lower alkoxycarbonyl, azetidinylcarbonyl, and substituted azetidinylcarbonyl.

Protective groups of hydroxyl as used herein include silyl-type protective groups, methyl, methoxymethyl, aryl, benzyl, aryloxycarbonyl, t-butoxycarbonyl, optionally substituted benzyloxycarbonyl, and acyl. Preferred are trimethylsilyl, triethylsilyl, t-butyldimethylsilyl, aryloxycarbonyl, t-butoxycarbonyl, 4-nitrobenzyloxycarbonyl, and 4-methoxybenzyloxycarbonyl.

More preferred groups indicated by $R^2$ and $R^3$, and $R^{2'}$ and $R^{3'}$ include a hydrogen atom, a halogen atom, amino, methyl, ethyl, propyl, cyanomethyl, hydroxymethyl, hydroxyethyl, acetoxymethyl, (2-hydroxyethoxy)methyl, (3-hydroxypropyloxy)methyl, (2-methoxyethoxy)methyl, (2-acetoxyethoxy)methyl, L-valyloxymethyl, carbamoyl, N-methylcarbamoyl, N-cyanomethylcarbamoyl, N-(2-cyanoethyl)carbamoyl, N-(2-hydroxyethyl)carbamoyl, N-(3-hydroxypropyl)carbamoyl, N,N-dimethylcarbamoyl, N-(2-hydroxyethyl)-N-methylcarbamoyl, N-cyanomethyl-N-methylcarbamoyl, methoxycarbonyl, ethoxycarbonyl, (azetidin-1-yl)carbonyl, (3-cyanoazetidin-1-yl)carbonyl, and (3-hydroxyazetidin-1-yl)carbonyl.

In a more preferred embodiment of the present invention, Examples of ring A in formula (II) include 2-hydroxymethylthiazole, 4-hydroxymethylthiazole, 5-hydroxymethylthiazole, 4-(2-hydroxyethoxy)methylthiazole, 2-N,N-dimethylcarbamoylthiazole, 4-N,N-dimethylcarbamoylthiazole, 5-N,N-dimethylcarbamoylthiazole, 4-methylthiazole, 2-carbamoylthiazole, 4-carbamoylthiazole, 5-carbamoylthiazole, 4-N-methylcarbamoylthiazole, 4-N-cyanomethyl-N-methylcarbamoylthiazole, 4-N-cyanomethylcarbamoylthiazole, 4-N-(2-cyanoethyl)carbamoylthiazole, 4-cyanomethylthiazole, 4-(2-methoxyethoxy)methylthiazole, 4-(3-cyanoazetidin-1-yl)carbonylthiazole, 4-N-(2-hydroxyethyl)carbamoylthiazole, 4-N-(3-hydroxypropan-1-yl)carbamoylthiazole, 4-N-(2-hydroxyethyl)-N-methylcarbamoylthiazole, 4-(azetidin-1-yl)carbonylthiazole, 4-(3-hydroxyazetidin-1-yl)carbonylthiazole, 4-(3-hydroxypropan-1-yloxy)methylthiazole, 2-amino-4-carbamoylthiazole, 2-aminothiazole, 4,5-dicarbamoylthiazole, 4-acetoxymethylthiazole, 4-(2-acetoxyethoxy)methylthiazole, 4-(L-valyloxymethyl)thiazole, 4-methoxycarbonylthiazole, 4-ethoxycarbonylthiazole, 2-amino-4-methoxycarbonylthiazole, and 2-amino-4-ethoxycarbonylthiazole.

$R^4$ represents a hydrogen atom or a biohydrolyzable group. $R^{4'}$ is a biohydrolyzable group as defined in $R^4$.

Biohydrolyzable groups indicated by $R^4$ are preferably ester residues, and examples thereof include conventional groups such as lower alkyl, lower alkenyl, lower alkylcarbonyloxy-lower alkyl, lower cycloalkylcarbonyloxy-lower alkyl, lower cycloalkylmethylcarbonyloxy-lower alkyl, lower alkenylcarbonyloxy-lower alkyl, arylcarbonyloxy lower alkyl, tetrahydrofuranylcarbonyloxymethyl, lower alkoxy-lower alkyl, lower alkoxy-lower alkoxy-lower alkyl, arylmethyloxy lower alkyl, arylmethyloxy-lower alkoxy-lower alkyl, lower alkoxycarbonyloxy lower alkyl, lower alkoxycarbonyloxy-lower alkoxy, lower cycloalkoxycarbonyloxy-lower alkyl, lower cycloalkylmethoxycarbonyloxy-lower alkyl, aryloxycarbonyloxy lower alkyl, 3-phthalidyl optionally having a substituent on its aromatic ring, 2-(3-phthalidylidene)ethyl optionally having a substituent on its aromatic ring, 2-oxotetrahydrofuran-5-yl, mono-lower alkylaminocarbonyloxymethyl, di-lower alkylaminocarbonyloxymethyl, 2-oxo-5-lower alkyl-1,3-dioxolen-4-ylmethyl, optionally substituted piperidinylcarbonyloxy lower alkyl, and lower alkyl-lower cycloalkylaminocarbonyloxy-lower alkyl.

Preferably, $R^4$ represents methyl, ethyl, 1-(cyclohexyloxycarbonyloxy)ethyl, acetoxymethyl, 1-(isopropyloxycarbonyloxy)ethyl, 1-(ethoxycarbonyloxy)ethyl, pivaloyloxymethyl, cyclohexyloxycarbonyloxymethyl, 1-(isobutyloxycarbonyloxy)ethyl, 1-(cyclohexyloxycarbonyloxy)-2-methylpropan-1-yl, isobutyloxycarbonyloxymethyl, isopropyloxycarbonyloxymethyl, isobutyryloxymethyl, (pentan-1-yl)oxycarbonyloxymethyl, (butan-1-yl)oxycarbonyloxymethyl, (1-ethylpropan-1-yl)oxycarbonyloxymethyl, isopentyloxycarbonyloxymethyl, (propan-1-yl)oxycarbonyloxymethyl, ethoxycarbonyloxymethyl, neopentyloxycarbonyloxymethyl, methoxycarbonyl oxymethyl, cyclopentyloxycarbonyloxymethyl, t-butoxycarbonyloxymethyl, phthalidyl, 1-(methoxycarbonyloxy)ethyl, 1-(cyclopentyloxycarbonyloxy)ethyl, (tetrahydropyran-4-yl)oxycarbonyloxymethyl, 1-(neopentyloxycarbonyloxy)ethyl, (piperidin-1-yl)carbonyloxymethyl, aryl, 1-(t-butoxycarbonyloxy)ethyl, (N,N-di-n-propylamino)carbonyloxymethyl, phenyloxycarbonyloxymethyl, (5-methyl-2-oxo-1,3-dioxolen-4-yl)methyl, (cis-2,6-dimethylpiperidin-1-yl)carbonyloxymethyl, N,N-di-(butan-1-yl)aminocarbonyloxymethyl, hexan-1-yl, N-(hexan-1-yl)-N-methylaminocarbonyloxymethyl, N,N-diisobutylaminocarbonyloxymethyl, N,N-diisopropylaminocarbonyloxymethyl, N-cyclohexyl-N-methylaminocarbonyloxymethyl, N-pentan-1-ylaminocarbonyloxymethyl, N-cyclohexyl-N-ethylaminocarbonyloxymethyl, N-isobutyl-N-isopropylaminocarbonyloxymethyl, N-t-butyl-N-ethylaminocarbonyloxymethyl, 1-[(cis-2,6-dimethylpiperidin-1-yl)carbonyloxy]ethyl, 1-(N,N-diisopropylaminocarbonyloxy)ethyl, or N-ethyl-N-isoamylaminocarbonyloxymethyl.

$R^5$ represents a hydrogen atom or a protective group of alkynyl.

$R^6$ represents $R^7$—S—C≡C— wherein $R^7$ represents a hydrogen atom, a metal ion, or a protective group of thiol.

Protective groups of alkynyl indicated by $R^5$ include silyl-type protective groups and 2-(2-hydroxypropyl). Preferred are trimethylsilyl, triethylsilyl, and t-butyldimethylsilyl.

Metal ions indicated by $R^7$ include alkali metal ions, alkaline earth metal ions, mercury ions, copper ions, silver ions, and iron ions. Preferred are lithium ions, sodium ions, potassium ions, silver ions, and mercury ions. $R^{7c}$ represents and is a metal ion as defined in $R^7$.

Protective groups of thiol indicated by $R^7$ include triphenylmethyl, diphenylmethyl, acyl-type protective groups (for example, acetyl, benzoyl, or trifluoroacetyl), optionally substituted benzyl, and silyl-type protective groups. Preferred are triphenylmethyl, acetyl, benzoyl, and 4-methoxybenzyl. $R^{7b}$ represents and is a protective group of thiol as defined in $R^7$.

Protective groups of hydroxyl indicated by $R^8$ include silyl-type protective groups, methyl, methoxymethyl, aryl, benzyl, aryloxycarbonyl, t-butoxycarbonyl, optionally substituted benzyloxycarbonyl, and acyl. Preferred are trimethylsilyl, triethylsilyl, t-butyldimethylsilyl, aryloxycarbonyl, t-butoxycarbonyl, 4-nitrobenzyloxycarbonyl, and 4-methoxybenzyloxycarbonyl.

Protective groups of carboxyl indicated by $R^9$ include lower alkyl, optionally substituted benzyl, silyl-type protective groups, aryl, triphenylmethyl, and diphenylmethyl. Preferred are methyl, t-butyl, benzyl, 4-methoxybenzyl, 4-nitrobenzyl, and aryl.

L represents a leaving group, and examples thereof include halogen atoms, lower alkylsulfonyloxy, optionally substituted arylsulfonyloxy, perfluoroalkanesulfonyloxy, fluorosulfonyloxy, lower alkylsulphenyl, optionally substituted arylsulphenyl, heterocyclic sulphenyl, and diphenylphosphoryloxy. Preferred are methanesulfonyloxy, toluenesulfonyloxy, trifluoromethanesulfonyloxy, and diphenylphosphoryloxy.

$R^{10}$ represents a hydrogen atom or a metal ion, preferably a hydrogen atom, a sodium ion, or a potassium ion.

Salts of the compounds represented by general formula (I) are pharmaceutically acceptable salts, and examples thereof include, inorganic salts such as lithium, sodium, potassium, calcium, and magnesium salts; ammonium salts; organic base salts such as triethylamine salts or diisopropylethylamine salts; mineral acid salts such as hydrochloric acid salts, sulfuric acid salts, phosphoric acid salts, or nitric acid salts; and organic acid salts such as acetic acid salts, carbonic acid salts, citric acid salts, malic acid salts, oxalic acid salts, or methanesulfonic acid salts. Preferred are sodium salts, potassium salts, and hydrochloric acid salts.

The compounds according to the present invention may form solvates. Such solvates include, for example, hydrates, alcoholates, for example, methanolates and ethanolates, and etherates such as diethyl etherates.

In one preferred embodiment of the present invention, in formula (III), one of $R^{2'}$ and $R^{3'}$ represents
hydroxymethyl,
acetoxymethyl,
methoxycarbonyl, or
ethoxycarbonyl, and
the other represents a hydrogen atom.

In one preferred embodiment of the present invention, in formula (IV), one of $R^{2'}$ and $R^{3'}$ represents
hydroxy lower alkyl,
hydroxy lower alkyl protected by a protective group of hydroxyl,
lower alkoxy-lower alkyl, or
lower alkoxycarbonyl, and
the other represents a hydrogen atom.

In one more preferred embodiment of the present invention, in formula (IV), one of $R^{2'}$ and $R^{3'}$ represents
hydroxymethyl,
acetoxymethyl,
methoxycarbonyl, or
ethoxycarbonyl, and
the other represents a hydrogen atom.

In one preferred embodiment of the present invention, $R^6$ is present at the 5-position on the thiazole ring in formula (IV).

Next, specific examples of carbapenem derivatives represented by general formula (I) according to the present invention and intermediates thereof will be described. The present invention, however, is not limited to these specific examples. The number described before the compound name represents the number of the compound.

1. 4-Hydroxymethyl-5-((Z)-2-tritylthioethen-1-yl)thiazole
2. 4-(2-Hydroxyethoxy)methyl-5-((Z)-2-tritylthioethen-1-yl)thiazole
3. 4-N,N-Dimethylcarbamoyl-5-((Z)-2-tritylthioethen-1-yl)thiazole
4. 4-Hydroxymethyl-2-((Z)-2-tritylthioethen-1-yl)thiazole
5. 4-Methyl-5-((Z)-2-tritylthioethen-1-yl)thiazole
6. 4-Carbamoyl-5-((Z)-2-tritylthioethen-1-yl)thiazole
7. 4-N-Methylcarbamoyl-5-((Z)-2-tritylthioethen-1-yl)thiazole
8. 4-N-Cyanomethyl-N-methylcarbamoyl-5-((Z)-2-tritylthioethen-1-yl)thiazole
9. 4-N-cyanomethylcarbamoyl-5-((Z)-2-tritylthioethen-1-yl)thiazole 10. 4-N-(2-Cyanoethyl)carbamoyl-5-((Z)-2-tritylthioethen-1-yl)thiazole
11. 4-Cyanomethyl-5-((Z)-2-tritylthioethen-1-yl)thiazole
12. 4-(2-Methoxyethoxy)methyl-5-((Z)-2-tritylthioethen-1-yl)thiazole
13. 4-(3-Cyanoazetidin-1-yl)carbonyl-5-((Z)-2-tritylthioethen-1-yl)thiazole
14. 4-N-(2-Hydroxyethyl)carbamoyl-5-((Z)-2-tritylthioethen-1-yl)thiazole
15. 4-N-(3-Hydroxypropan-1-yl)carbamoyl-5-((Z)-2-tritylthioethen-1-yl)thiazole
16. 4-N-(2-Hydroxyethyl)-N-methylcarbamoyl-5-((Z)-2-tritylthioethen-1-yl)thiazole
17. 4-(Azetidin-1-yl)carbonyl-5-((Z)-2-tritylthioethen-1-yl)thiazole
18. 4-(3-Hydroxyazetidin-1-yl)carbonyl-5-((Z)-2-tritylthioethen-1-yl)thiazole
19. 4-(3-Hydroxypropan-1-yloxy)methyl-5-((Z)-2-tritylthioethen-1-yl)thiazole
20. 2-Amino-4-carbamoyl-5-((Z)-2-tritylthioethen-1-yl)thiazole
21. 4-Hydroxymethyl-5-((E)-2-tritylthioethen-1-yl)thiazole
22. 2-Carbamoyl-5-((Z)-2-tritylthioethen-1-yl)thiazole
23. 2-Amino-5-((Z)-2-tritylthioethen-1-yl)thiazole
24. 2-N,N-Dimethylcarbamoyl-5-((Z)-2-tritylthioethen-1-yl)thiazole
25. 4-Carbamoyl-2-((Z)-2-tritylthioethen-1-yl)thiazole
26. 4-N-(2-Hydroxyethyl)carbamoyl-2-((Z)-2-tritylthioethen-1-yl)thiazole
27. 4-N,N-Dimethylcarbamoyl-2-((Z)-2-tritylthioethen-1-yl)thiazole
28. 4-N-Methylcarbamoyl-2-((Z)-2-tritylthioethen-1-yl)thiazole
29. 4-N-Cyanomethylcarbamoyl-2-((Z)-2-tritylthioethen-1-yl)thiazole
30. 4-N-Cyanomethyl-N-methylcarbamoyl-2-((Z)-2-tritylthio ethen-1-yl)thiazole
31. 4-Cyanomethyl-2-((Z)-2-tritylthioethen-1-yl)thiazole
32. 4-(3-Hydroxyazetidin-1-yl)carbonyl-2-((Z)-2-tritylthioethen-1-yl)thiazole
33. 4-(3-Cyanoazetidin-1-yl)carbonyl-2-((Z)-2-tritylthioethen-1-yl)thiazole
34. 5-Hydroxymethyl-2-((Z)-2-tritylthioethen-1-yl)thiazole
35. 4,5-Dicarbamoyl-2-((Z)-2-tritylthioethen-1-yl)thiazole
36. 4-((Z)-2-Tritylthioethen-1-yl)thiazole
37. 2-Carbamoyl-4-((Z)-2-tritylthioethen-1-yl)thiazole
38. 5-Hydroxymethyl-4-((Z)-2-tritylthioethen-1-yl)thiazole
39. 4-Ethoxycarbonyl-5-(2-trimethylsilylethynyl)thiazole
40. 4-Ethoxycarbonyl-5-ethynylthiazole
41. Sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
42. Sodium (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate
43. Sodium (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate
44. Sodium (1R,5S,6S)-6-((1R)-1-hydroxyethyl)-2-[[(Z)-2-(4-hydroxymethylthiazol-2-yl)ethen-1-yl]thio]-1-methyl-1-carbapen-2-em-3-carboxylate
45. Sodium (1R,5S,6S)-6-((1R)-1-hydroxyethyl)-1-methyl-2-[[(Z)-2-(4-methylthiazol-5-yl)ethen-1-yl]thio]-1-carbapen-2-em-3-carboxylate
46. Sodium (1R,5S,6S)-2-[[(Z)-2-(4-carbamoylthiazol-5-yl)ethen-1-yl]thio]-6-((1R)-1-hydroxyethyl)-1-methyl-1-carbapen-2-em-3-carboxylate
47. Sodium (1R,5S,6S)-6-((1R)-1-hydroxyethyl)-1-methyl-2-[[(Z)-2-(4-N-methylcarbamoylthiazol-5-yl)ethen-1-yl]thio]-1-carbapen-2-em-3-carboxylate
48. Sodium (1R,5S,6S)-2-[[(Z)-2-(4-N-cyanomethyl-N-methylcarbamoylthiazol-5-yl)ethen-1-yl]thio]-6-((1R)-1-hydroxyethyl)-1-methyl-1-carbapen-2-em-3-carboxylate
49. Sodium (1R,5S,6S)-2-[[(Z)-2-(4-N-cyanomethylcarbamoylthiazol-5-yl)ethen-1-yl]thio]-6-((1R)-1-hydroxyethyl)-1-methyl-1-carbapen-2-em-3-carboxylate
50. Sodium (1R,5S,6S)-2-[[(Z)-2-[4-N-(2-cyanoethyl)carbamoylthiazol-5-yl]ethen-1-yl]thio]-6-((1R)-1-hydroxyethyl)-1-methyl-1-carbapen-2-em-3-carboxylate
51. Sodium (1R,5S,6S)-2-[[(Z)-2-(4-cyanomethylthiazol-5-yl)ethen-1-yl]thio]-6-((1R)-1-hydroxyethyl)-1-methyl-1-carbapen-2-em-3-carboxylate
52. Sodium (1R,5S,6S)-6-((1R)-1-hydroxyethyl)-2-[[(Z)-2-[4-(2-methoxyethoxy)methylthiazol-5-yl]ethen-1-yl]thio]-1-methyl-1-carbapen-2-em-3-carboxylate
53. Sodium (1R,5S,6S)-2-[[(Z)-2-[4-(3-cyanoazetidin-1-yl)carbonylthiazol-5-yl]ethen-1-yl]thio]-6-((1R)-1-hydroxyethyl)-1-methyl-1-carbapen-2-em-3-carboxylate
54. Sodium (1R,5S,6S)-6-((1R)-1-hydroxyethyl)-2-[[(Z)-2-[4-N-(2-hydroxyethyl)carbamoylthiazol-5-yl]ethen-1-yl]thio]-1-methyl-1-carbapen-2-em-3-carboxylate
55. Sodium (1R,5S,6S)-6-((1R)-1-hydroxyethyl)-2-[[(Z)-2-[4-N-(3-hydroxypropan-1-yl)carbamoylthiazol-5-yl]ethen-1-yl]thio]-1-methyl-1-carbapen-2-em-3-carboxylate
56. Sodium (1R,5S,6S)-6-((1R)-1-hydroxyethyl)-2-[[(Z)-2-[4-N-(2-hydroxyethyl)-N-methylcarbamoylthiazol-5-yl]ethen-1-yl]thio]-1-methyl-1-carbapen-2-em-3-carboxylate
57. Sodium (1R,5S,6S)-2-[[(Z)-2-[4-(azetidin-1-yl)carbonylthiazol-5-yl]ethen-1-yl]thio]-6-((1R)-1-hydroxyethyl)-1-methyl-1-carbapen-2-em-3-carboxylate
58. Sodium (1R,5S,6S)-2-[[(Z)-2-(4-(3-hydroxyazetidin-1-yl)carbonylthiazol-5-yl)ethen-1-yl]thio]-6-((1R)-1-hydroxyethyl)-1-methyl-1-carbapen-2-em-3-carboxylate
59. Sodium (1R,5S,6S)-6-((1R)-1-hydroxyethyl)-2-[[(Z)-2-[4-(3-hydroxypropan-1-yloxy)methylthiazol-5-yl]ethen-1-yl]thio]-1-methyl-1-carbapen-2-em-3-carboxylate
60. Sodium (1R,5S,6S)-2-[[(Z)-2-(2-amino-4-carbamoylthiazol-5-yl)ethen-1-yl]thio]-6-((1R)-1-hydroxyethyl)-1-methyl-1-carbapen-2-em-3-carboxylate
61. Sodium (1R,5S,6S)-6-((1R)-1-hydroxyethyl)-2-[[(E)-2-(4-hydroxymethylthiazol-5-yl)ethen-1-yl]thio]-1-methyl-1-carbapen-2-em-3-carboxylate
62. Sodium (1R,5S,6S)-2-[[(Z)-2-(2-carbamoylthiazol-5-yl)ethen-1-yl]thio]-6-((1R)-1-hydroxyethyl)-1-methyl-1-carbapen-2-em-3-carboxylate
63. Sodium (1R,5S,6S)-2-[[(Z)-2-(2-aminothiazol-5-yl)ethen-1-yl]thio]-6-((1R)-1-hydroxyethyl)-1-methyl-1-carbapen-2-em-3-carboxylate
64. Sodium (1R,5S,6S)-2-[[(Z)-2-(2-N,N-dimethylcarbamoylthiazol-5-yl)ethen-1-yl]thio]-6-((1R)-1-hydroxyethyl)-1-methyl-1-carbapen-2-em-3-carboxylate
65. Sodium (1R,5S,6S)-2-[[(Z)-2-(4-carbamoylthiazol-2-yl)ethen-1-yl]thio]-6-((1R)-1-hydroxyethyl)-1-methyl-1-carbapen-2-em-3-carboxylate
66. Sodium (1R,5S,6S)-2-[[(Z)-2-[4-N-(2-hydroxyethyl)carbamoylthiazol-2-yl]ethen-1-yl]thio]-6-((1R)-1-hydroxyethyl)-1-methyl-1-carbapen-2-em-3-carboxylate
67. Sodium (1R,5S,6S)-2-[[(Z)-2-(4-N,N-dimethylcarbamoylthiazol-2-yl)ethen-1-yl]thio]-6-((1R)-1-hydroxyethyl)-1-methyl-1-carbapen-2-em-3-carboxylate 68. Sodium (1R,5S,6S)-6-((1R)-1-hydroxyethyl)-1-methyl-2-[[(Z)-2-(4-N-methylcarbamoylthiazol-2-yl)ethen-1-yl]thio]-1-carbapen-2-em-3-carboxylate
69. Sodium (1R,5S,6S)-2-[[(Z)-2-(4-N-cyanomethylcarbamoylthiazol-2-yl)ethen-1-yl]thio]-6-((1R)-1-hydroxyethyl)-1-methyl-1-carbapen-2-em-3-carboxylate
70. Sodium (1R,5S,6S)-2-[[(Z)-2-(4-N-cyanomethyl-N-methylcarbamoylthiazol-2-yl)ethen-1-yl]thio]-6-((1R)-1-hydroxyethyl)-1-methyl-1-carbapen-2-em-3-carboxylate
71. Sodium (1R,5S,6S)-2-[[(Z)-2-(4-cyanomethylthiazol-2-yl)ethen-1-yl]thio]-6-((1R)-1-hydroxyethyl)-1-methyl-1-carbapen-2-em-3-carboxylate
72. Sodium (1R,5S,6S)-2-[[(Z)-2-(4-(3-hydroxyazetidin-1-yl)carbonylthiazol-2-yl)ethen-1-yl]thio]-6-((1R)-1-hydroxyethyl)-1-methyl-1-carbapen-2-em-3-carboxylate
73. Sodium (1R,5S,6S)-2-[[(Z)-2-(4-(3-cyanoazetidin-1-yl)carbonylthiazol-2-yl)ethen-1-yl]thio]-6-((1R)-1-hydroxyethyl)-1-methyl-1-carbapen-2-em-3-carboxylate
74. Sodium (1R,5S,6S)-6-((1R)-1-hydroxyethyl)-2-[[(Z)-2-(5-hydroxymethylthiazol-2-yl)ethen-1-yl]thio]-1-methyl-1-carbapen-2-em-3-carboxylate
75. Sodium (1R,5S,6S)-2-[[(Z)-2-(4,5-dicarbamoylthiazol-2-yl)ethen-1-yl]thio]-6-((1R)-1-hydroxyethyl)-1-methyl-1-carbapen-2-em-3-carboxylate
76. Sodium (1R,5S,6S)-6-((1R)-1-hydroxyethyl)-1-methyl-2-[[(Z)-2-(thiazol-4-yl)ethen-1-yl]thio]-1-carbapen-2-em-3-carboxylate
77. Sodium (1R,5S,6S)-2-[[(Z)-2-(2-carbamoylthiazol-4-yl)ethen-1-yl]thio]-6-((1R)-1-hydroxyethyl)-1-methyl-1-carbapen-2-em-3-carboxylate
78. Sodium (1R,5S,6S)-6-((1R)-1-hydroxyethyl)-2-[[(Z)-2-(5-hydroxymethylthiazol-4-yl)ethen-1-yl]thio]-1-methyl-1-carbapen-2-em-3-carboxylate
79. Sodium (1R,5S,6S)-2-[[(Z)-2-(4-acetoxymethylthiazol-5-yl)ethen-1-yl]thio]-6-((1R)-1-hydroxyethyl)-1-methyl-1-carbapen-2-em-3-carboxylate
80. Sodium (1R,5S,6S)-2-[[(Z)-2-[4-(2-acetoxyethoxy)methylthiazol-5-yl]ethen-1-yl]thio]-6-((1R)-1-hydroxyethyl)-1-methyl-1-carbapen-2-em-3-carboxylate
81. 1-(Cyclohexyloxycarbonyloxy)ethyl (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate (diastereomer mixture)
82. 1-(Cyclohexyloxycarbonyloxy)ethyl (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate (diastereomer mixture)
83. 1-(Cyclohexyloxycarbonyloxy)ethyl (1R,5S,6S)-6-((1R)-1-hydroxyethyl)-2-[[(Z)-2-(4-hydroxymethylthiazol-2-yl)ethen-1-yl]thio]-1-methyl-1-carbapen-2-em-3-carboxylate (diastereomer mixture)
84. 1-(Cyclohexyloxycarbonyloxy)ethyl (1R,5S,6S)-2-[[(Z)-2-(4-carbamoylthiazol-5-yl)ethen-1-yl]thio]-6-((1R)-1-hydroxyethyl)-1-methyl-1-carbapen-2-em-3-carboxylate (diastereomer mixture)
85. 1-(Cyclohexyloxycarbonyloxy)ethyl (1R,5S,6S)-2-[[(Z)-2-(4-N-cyanomethylcarbamoylthiazol-5-yl)ethen-1-yl]thio]-6-((1R)-1-hydroxyethyl)-1-methyl-1-carbapen-2-em-3-carboxylate (diastereomer mixture)
86. 1-(Cyclohexyloxycarbonyloxy)ethyl (1R,5S,6S)-6-((1R)-1-hydroxyethyl)-2-[[(Z)-2-[4-N-(2-hydroxyethyl)carbamoyl-thiazol-5-yl]ethen-1-yl]thio]-1-methyl-1-carbapen-2-em-3-carboxylate (diastereomer mixture)
87. Pivaloyloxymethyl (1R,5S,6S)-2-[[(Z)-2-(2-carbamoylthiazol-5-yl)ethen-1-yl]thio]-6-((1R)-1-hydroxyethyl)-1-methyl-1-carbapen-2-em-3-carboxylate
88. 1-(Cyclohexyloxycarbonyloxy)ethyl (1R,5S,6S)-6-((1R)-1-hydroxyethyl)-2-[[(Z)-2-[4-N-(2-hydroxyethyl)carbamoylthiazol-2-yl]ethen-1-yl]thio]-1-methyl-1-carbapen-2-em-3-carboxylate (diastereomer mixture)
89. 1-(Cyclohexyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
90. Acetoxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
91. 1-(Isopropyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
92. 1-(Ethoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
93. Pivaloyl oxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
94. Cyclohexyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
95. 1-(Isobutyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
96. 1-(Cyclohexyloxycarbonyloxy)-2-methylpropan-1-yl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate (diastereomer mixture)
97. Isobutyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
98. Isopropyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
99. Isobutyryloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
100. (Pentan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
101. (Butan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
102. (1-Ethylpropan-1-yl)oxycarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
103. Isopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
104. (Propan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
105. 1-(Cyclohexyloxycarbonyloxy)ethyl (1R,5S,6S)-2-[[(Z)-2-(4-acetoxymethylthiazol-5-yl)ethen-1-yl]thio]-6-

((1R)-1-hydroxyethyl)-1-methyl-1-carbapen-2-em-3-carboxylate (diastereomer mixture)
106. Ethoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
107. Neopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
108. Methoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
109. Cyclopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
110. t-Butoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
111. Phthalidyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
112. 1-(Methoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
113. 1-(Cyclopentyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
114. (Tetrahydropyran-4-yl)oxycarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
115. 1-(Neopentyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
116. (Piperidin-1-yl)carbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
117. Allyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
118. (1R,5S,6S)-6-((1R)-1-Hydroxyethyl)-1-methyl-2-[[(Z)-2-(4-(L-valinyloxymethyl)thiazol-5-yl)ethen-1-yl]thio]-1-carbapen-2-em-3-carboxylic acid
119. 1-(t-Butoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
120. 1-(t-Butoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
121. Ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
122. (5-Methyl-2-oxo-1,3-dioxolen-4-yl)methyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
123. Phenyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
124. N,N-Di(propan-1-yl)aminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
125. (Cis-2,6-dimethylpiperidin-1-yl)carbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
126. N,N-Di-(butan-1-yl)aminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
127. Hexan-1-yl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
128. N-(Hexan-1-yl)-N-methylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
129. N,N-Diisobutylaminocarbonyloxymethyl (1R,5S,6S)-6-((1R)-1-hydroxyethyl)-2-[[(Z)-2-(4-hydroxymethylthi-azol-5-yl)ethen-1-yl]thio]-1-methyl-1-carbapen-2-em-3-carboxylate
130. N,N-Diisopropylaminocarbonyloxymethyl (1R,5S,6S)-6-((1R)-1-hydroxyethyl)-2-[[(Z)-2-(4-hydroxymethylthi-azol-5-yl)ethen-1-yl]thio]-1-methyl-1-carbapen-2-em-3-carboxylate
131. N-Cyclohexyl-N-methylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
132. N-Pentan-1-ylaminocarbonyloxymethyl (1R,5S,6S)-6-((1R)-1-hydroxyethyl)-2-[[(Z)-2-(4-hydroxymethylthi-azol-5-yl)ethen-1-yl]thio]-1-methyl-1-carbapen-2-em-3-carboxylate
133. N-Cyclohexyl-N-ethylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
134. N-Isobutyl-N-isopropylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
135. N-t-Butyl-N-ethylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate
136. 1-(N,N-Diisopropylaminocarbonyloxy)ethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate (diastereomer mixture)
137. 1-[(Cis-2,6-dimethylpiperidin-1-yl)carbonyloxy]ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)
138. N-Ethyl-N-isoamylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate
139. (5-Bromothiazol-4-yl)-methanol
140. [5-[2-(Trimethylsilyl)ethynyl]thiazol-4-yl]-methanol
141. 5-Ethynyl-4-hydroxymethylthiazole 142. N,N-Diisopropylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate 143. Sodium (5R,6S)-6-((1R)-1-hydroxyethyl)-2-[[(Z)-2-(4-hydroxy methylthiazol-5-yl)ethen-1-yl]thio]-1-carbapen-2-em-3-carboxylate 144. N,N-Diisopropylaminocarbonyloxymethyl (5R,6S)-6-((1R)-1-hydroxyethyl)-2-[[(Z)-2-(4-hydroxy methylthiazol-5-yl)ethen-1-yl]thio]-1-carbapen-2-em-3-carboxylate 145. (1R,5S,6S)-6-((1R)-1-Hydroxyethyl)-2-[[(Z)-2-(4-hydroxymethylthiazol-5-yl)ethen-1-yl]thio]-1-methyl-1-carbapen-2-em-3-carboxylic acid 146. Potassium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate 147. N,N-Diisopropylaminocarbonyloxymethyl (1R,5S,6S)-6-((1R)-1-hydroxyethyl)-2-[[(E)-2-(4-hydroxymethylthiazol-5-yl)ethen-1-yl]thio]-1-methyl-1-carbapen-2-em-3-carboxylates.

Production Process of Compounds

The compounds according to the present invention can be produced, for example, according to the following scheme. Starting compounds necessary for the synthesis of the compounds according to the present invention are commercially available or alternatively can easily be produced by a conventional method.

Among the compounds of formula (I) according to the present invention, compounds wherein $R^4$ represents a hydrogen atom or salts thereof, that is, compounds of formula (I'), are preferably be produced according to the following scheme.

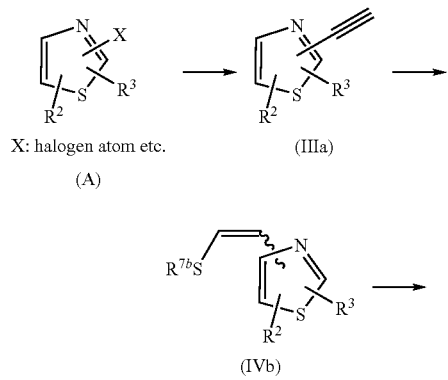

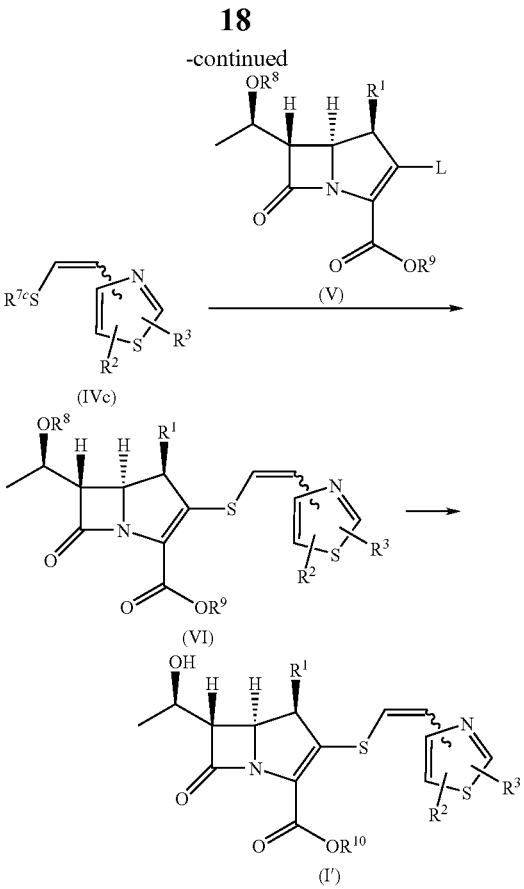

wherein $R^1$, $R^2$, and $R^3$ are as defined in formula (I); $R^{7b}$ represents a protective group of thiol as defined in $R^7$, for example, triphenylmethyl, acetyl, benzoyl, or 4-methoxybenzyl; $R^{7c}$ represents a metal ion as defined in $R^7$, for example, a lithium ion, a sodium ion, a potassium ion, a silver ion, or a mercury ion; $R^8$ represents a hydrogen atom or a protective group of hydroxyl, for example, t-butyldimethylsilyl, trimethylsilyl, triethylsilyl, 4-nitrobenzyloxycarbonyl, or 4-methoxybenzyloxycarbonyl, aryloxycarbonyl; $R^9$ represents a protective group of carboxyl, for example, 4-nitrobenzyl, 4-methoxybenzyl, diphenylmethyl, t-butyldimethylsilyl, or aryl; and $R^{10}$ represents a hydrogen atom or a metal ion such as a potassium or sodium ion; and X represents a halogen atom.

The compound of formula (IIIa) may be produced by a Sonogashira reaction between a thiazole compound of formula (A) having a leaving group such as a halogen atom and trimethylsilylacetylene and detrimethylsilylation, or a Stille coupling reaction between a thiazole compound of formula (A) and tributylethynyltin. A compound wherein one of $R^2$ and $R^3$ represents hydroxymethyl and the other represents a hydrogen atom (a compound of formula (d)) will be described as an example.

Scheme 2

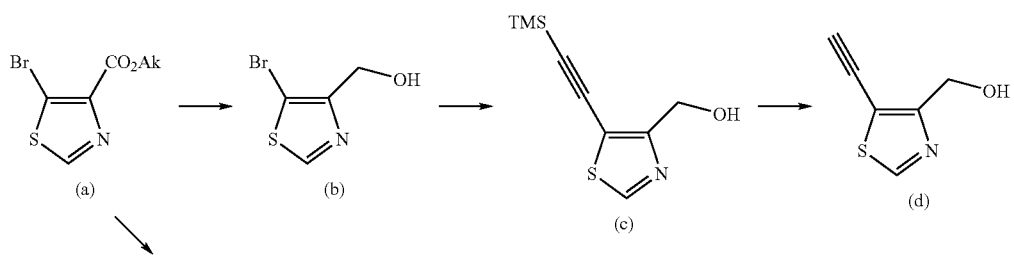

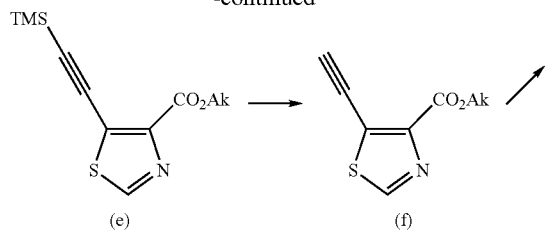

wherein Ak represents lower alkyl such as methyl, ethyl, n-propyl, isopropyl, n-butyl, i-butyl, s-butyl, t-butyl, n-pentyl, neopentyl, i-pentyl, t-pentyl, n-hexyl, or i-hexyl.

The compound of formula (b) may be produced by reacting a compound of formula (a) with a reducing agent such as sodium borohydride, diisobutylaluminum, lithium aluminum hydride in a suitable solvent, for example, acetonitrile, dichloromethane, 1,2-dichloroethane, tetrahydrofuran, diethyl ether, toluene, benzene, methanol, ethanol, or water, or a mixed solvent composed of these solvents in the presence or absence of lithium chloride, calcium chloride, cerium chloride or the like for 10 min to 72 hr.

Next, the compound of formula (c) may be produced by reacting a compound of formula (b) with various palladium complexes, for example, dichlorobis(triphenylphosphine) palladium, or bis(benzonitrile)palladium dichloride, and copper iodie, and a trivalent phosphorus reagent such as triphenylphosphine, tributylphosphine or trifurylphosphine, and one equivalent or an excessive amount of trimethylacetylene in a suitable solvent, for example, acetone, acetonitrile, dichloromethane, 1,2-dichloroethane, ethyl acetate, tetrahydrofuran, dioxane, diethyl ether, isopropyl ether, hexane, N,N-dimethylformamide, dimethylsulfoxide, toluene, benzene, methanol, ethanol, triethylamine, or hexamethylphosphoric triamide or a mixed solvent composed of these solvents, in the presence of one equivalent or an excessive amount of a base, for example, an organic base such as triethylamine, diisopropylamine, diisopropylethyl amine, or pyridine, or an inorganic base such as sodium hydroxide, potassium hydroxide, sodium hydrogencarbonate, potassium hydrogencarbonate, sodium carbonate, potassium carbonate, or cesium carbonate, at $-30°$ C. to $100°$ C. for 10 min to 72 hr.

Finally, the compound of formula (d) may be produced by adding not more than 10 equivalents of acetic acid and tetra-n-butyl ammonium fluoride, or not more than 10 equivalents of a base, for example, sodium hydroxide, potassium hydroxide, sodium hydrogencarbonate, potassium hydrogencarbonate, sodium carbonate, potassium carbonate, or cesium carbonate to the compound of formula (c) in a suitable solvent, for example, acetone, acetonitrile, dichloromethane, 1,2-dichloroethane, ethyl acetate, tetrahydrofuran, or dioxane, and allowing a reaction to preceed at $-80°$ C. to $50°$ C. for 5 min to 24 hr. After the completion of the reaction, a conventional post treatment may be carried out to give the compound of formula (d).

Alternatively, the compound of formula (d) may also be produced by a process via compounds of formulae (e) and (f). The compound of formula (e) may be produced from the compound of formula (a) in the same manner as in the step for the production of the compound of formula (c) from the compound of formula (b). The compound of formula (f) may be produced from the compound by formula (e) in the same manner as in the step for the production of the compound of formula (d) from the compound of formula (c). Finally, the step for the production of the compound of formula (d) from the compound of formula (f) may be carried out in the same manner as in the step for the production of the compound of formula (b) from the compound of formula (a).

The conversion of the compound of formula (IVb) from the compound of formula (IIIa) may be carried out by the following process. Specifically, the compound of formula (IVb) may be produced by reacting ethynylthiazole of formula (IIIa) with a corresponding thiol.

The corresponding thiol is represented by formula $R^{7b}SH$ wherein $R^{7b}$ is as defined above, and examples thereof include triphenylmethane thiol, thioacetic acid, thiobenzoic acid, and 4-methoxy-alpha-toluenethiol.

Here an explanation will be given by taking the case where $R^{7b}$ represents triphenylmethyl, as an example.

The compound of formula (IVb) may be produced by acting one equivalent or an excessive amount of triphenylmethane thiol and a catalytic amount or more of a base, for example, an organic base such as diisopropylethyl amine, triethylamine, 2,6-lutidine, or pyridine, or an inorganic base such as sodium hydride, sodium hydroxide, potassium hydroxide, sodium methoxide, sodium ethoxide, potassium-t-butoxide, sodium hydrogencarbonate, potassium hydrogencarbonate, sodium carbonate, potassium carbonate, or cesium carbonate, on the compound of formula (IIIa) in acetonitrile, acetone, N,N-dimethylformamide, N,N-dimethylacetamide, tetrahydrofuran, dioxane, methanol, ethanol, dichloromethane, toluene, hexamethylphosphoric triamide, water or the like or a mixed solvent composed of these solvents, allowing a reaction to proceed at $-80°$ C. to $+100°$ C. for 5 min to 24 hr, and then conducting conventional post treatment.

The conversion of the compound of formula (IVc) from the compound of formula (IVb) can be carried out by the following process. Here an explanation will be given by taking the case where the metal ion is a silver ion, as an example.

Specifically, the compound of formula (IVc) may be produced by adding one equivalent or an excessive amount of pyridine or silver nitrate to the compound of formula (IVb) and allowing a reaction to proceed in a solvent such as THF, acetone, methanol, dichloromethane, chloroform, or water or a mixed solvent composed of these solvents at $0°$ C. to $+50°$ C. for 5 min to 8 hr, and then filtering the reaction mixture.

In the next step, the conversion of the compound of formula (VI) from the compound of formula (IVc) may be carried out. This conversion may be carried out by the following process.

Specifically, the compound of formula (VI) may be produced by reacting the compound of formula (IVc) with the compound of formula (V) optionally adding one equivalent or an excessive amount, based on the compound of formula (IVc), of sodium iodide, for example, in acetonitrile, acetone, N,N-dimethylformamide, N,N-dimethylacetamide, tetrahydrofuran, dioxane, methanol, ethanol, dichloromethane, toluene, or hexamethylphosphoric triamide or a mixed solvent composed of these solvents at $-20°$ C. to $100°$ C. for 10 min to three days, and then conducting a conventional post treatment.

The compound of formula (V) may be, for example, a commercially available product.

Finally, the compound of formula (I') according to the present invention may be produced by removing the protective group of the compound of formula (VI) by a deprotection reaction in one stage or a plurality of stages depending on the type of the protective group.

In this case, the deprotection reaction for the removal of the protective group may vary depending upon the type of the protective group used. In general, however, the deprotection reaction may be carried out by a conventional method known in the art. When any of or the whole protective group can be removed under acidic conditions, a mineral acid such as hydrochloric acid, an organic acid such as forming acid, acetic acid, or citric acid, or a Lewis acid such as aluminum chloride maybe used. On the other hand, when the removal is carried out under reduction conditions, catalytic reduction in the presence of various catalysts may be used, or alternatively a metal reducing agent such as zinc or iron may be used. When $R^8$ represents a silyl-type protective group, for example, t-butyldimethylsilyl, trimethylsilyl, or triethylsilyl, the protective group can easily be removed by using a fluoride ion reagent, for example, tetrabutylammonium fluoride. Further, when $R^8$ represents aryloxycarbonyl and $R^9$ represents aryl, the protective group can easily be removed by using various palladium complexes, for example, tetrakis (triphenylphosphine)palladium(0).

The compound of formula (I') thus obtained may be isolated and purified, for example, by chromatography using a nonionic macro-high porous resin, gel filtration with Sephadex or the like, or reverse phase column chromatography on silica gel.

Among the compounds of general formula (I) according to the present invention, compounds of formula (I") wherein $R^4$ represents a biohydrolyzable group are preferably produced according to the following scheme.

Scheme 3

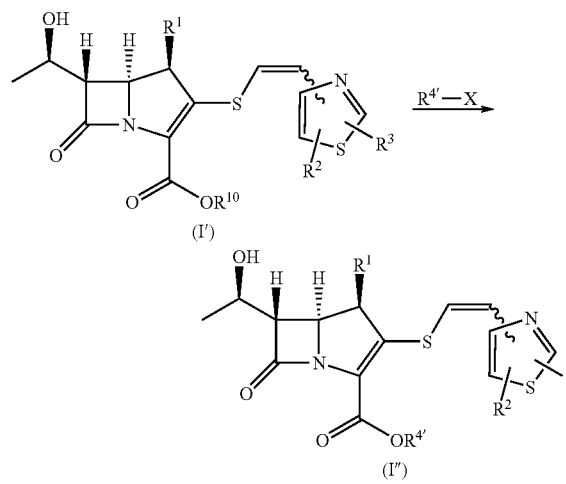

wherein $R^1$, $R^2$, and $R^3$ are as defined in formula (I); $R^{10}$ represents a hydrogen atom or a metal ion such as a potassium or sodium ion; $R^{4'}$ represents a biohydrolyzable group as defined above in connection with $R^4$ in the column of "Compounds"; and X represents a leaving group such as chlorine, bromine, iodine, —OSO$_2$CF$_3$, —OSO$_2$CH$_3$, or —OSO$_2$PhCH$_3$.

The compound of formula (I") can be produced by reacting the compound of formula (I') with one equivalent or an excessive amount of an alkyl halide, wherein $R^{4'}$—X: X represents a halogen atom, preferably iodine, bromine, or chlorine, for example, ethyl iodide, 1-(cyclohexyloxycarbonyloxy)ethyl iodide, bromomethyl acetate 1-(isopropyloxycarbonyloxy) ethyl iodide, 1-(ethoxycarbonyloxy)ethyl iodide, iodomethyl pivalate, cyclohexyloxycarbonyloxymethyl iodide, 1-(isobutyloxycarbonyloxy)ethyl iodide, 1-(cyclohexyloxycarbonyloxy)-2-methylpropan-1-yl iodide, isobutyloxycarbonyloxymethyl iodide, isopropyloxycarbonyloxymethyl iodide, isobutyryloxymethyl iodide, (pentan-1-yl)oxycarbonyloxymethyl iodide, (butan-1-yl)oxycarbonyloxymethyl iodide, (1-ethylpropan-1-yl)oxycarbonyloxymethyl iodide, isopentyloxycarbonyloxymethyl iodide, (propan-1-yl)oxymethyl iodide, ethoxycarbonyloxymethyl iodide, neopentyloxycarbonyloxymethyl iodide, methoxycarbonyloxymethyl iodide, cyclopentyloxycarbonyloxymethyl iodide, t-butoxycarbonyloxymethyl iodide, 3-bromophthalide, 1-(methoxycarbonyloxy)ethyl iodide, 1-(cyclopentyloxycarbonyloxy) ethyl iodide, (tetrahydropyran-4-yl)oxycarbonyloxymethyl iodide, 1-(neopentyloxycarbonyloxy)ethyl iodide, (piperidin-1-yl)carbonyloxymethyl iodide, aryl iodide, 1-(t-butoxycarbonyloxy)ethyl iodide, N,N-di(propan-1-yl)aminocarbonyloxymethyl iodide, phenyloxycarbonyloxymethyl iodide, (5-methyl-2-oxo-1,3-dioxolen-4-yl)methyl bromide, (Z)-2-(3-phthalidylidene)ethyl bromide, (cis-2,6-dimethylpiperidin-1-yl)carbonyloxymethyl chloride, chloromethyl N,N-di-n-butylcarbamate, 1-iodohexane, chloromethyl N-n-hexyl-N-methyl carbamate, chloromethyl N,N-diisobutylcarbamate, chloromethyl N,N-diisopropylcarbamate, chloromethyl N-cyclohexyl-N-methylcarbamate, chloromethyl N-pentan-1-ylcarbamate, chloromethyl N-cyclohexyl-N-ethylcarbamate, chloromethyl N-isobutyl-N-isopropylcarbamate, chloromethyl N-t-butyl-N-ethylcarbamate, 1-chloroethyl N,N-diisopropylcarbamate, 1-[(cis-2,6-dimethylpiperidin-1-yl)carbonyloxy] ethyl chloride, or chloromethyl N-ethyl-N-isoamylcarbamate, in a single or mixed inert solvent, for example, N,N-dimethylformamide, N,N-dimethylacetamide, N,N-diethylformamide, N,N-diethylacetamide, N-methylpyrrolidinone, N,N-dimethylimidazolidinone, dimethyl sulfoxide, sulfolane, acetonitrile, acetone, ethyl acetate, tetrahydrofuran, 1,4-dioxane, diethyl ether, anisole, dichloromethane, 1,2-dichloroethane, chloroform, toluene, benzene, hexamethylphosphoric triamide, methanol, or ethanol, optionally in the presence of one equivalent or an excessive amount of a base, for example, an organic base such as diisopropylethylamine, diazabicyclo[2,2,2]undecene, or 2,6-lutidine, or an inorganic base such as sodium hydroxide, potassium hydroxide, sodium hydrogencarbonate, potassium hydrogencarbonate, sodium carbonate, potassium carbonate, or cesium carbonate or/and a quaternary ammonium salt, for example, triethylbenzylammonium chloride, tetraethylammonium chloride, tetrabutylammonium chloride, or tetrabutylammonium bromide, at a temperature in a range of −70 to +50° C., preferably at a temperature in a range of −30° C. to +30° C., for 10 min to 24 hr.

The ester compound thus obtained was isolated and purified, for example, by precipitation, or gel filtration with Sephadex or the like, column chromatography on silica gel, or reverse phase column chromatography.

Use of Compounds/Pharmaceutical Composition

The compounds according to the present invention inhibit, in vitro, the growth of pathogenic bacteria and have antimicrobacterial activity (see Test Example 1). Further, it has been demonstrated that, also in an in vivo test, the compounds according to the present invention inhibits the growth of pathogenic bacteria and have antibacterial activity. Specifically, the carbapenem derivatives represented by formula (I) according to the present invention have potent antimicrobial activity against various pathogenic bacteria, for example, pneumococci including PRSP, *Haemophilus influenzae* including BLNAR, *Moraxella* (*Branhamella*) *catarrhalis*, and β-lactamase producing bacteria. Accordingly, the compounds according to the present invention can be said to be very useful for the prevention or treatment of bacterial infectious diseases or symptoms related thereto.

Thus, the compounds according to the present invention can be used for the prevention or treatment of bacterial infectious diseases and symptoms related thereto. Bacteria inducing such bacterial infectious diseases include those selected from the group consisting of pneumococci, *Haemophilus influenzae*, *Moraxella* (*Branhamella*) *catarrhalis*, and β-lactamase producing bacteria.

According to the present invention, there is provided a pharmaceutical composition comprising a compound represented or a pharmaceutically acceptable salt thereof according to the present invention. Preferably, the pharmaceutical composition may further comprise a pharmaceutically acceptable carrier. The pharmaceutical composition according to the present invention can be used for the prevention or treatment of bacterial infectious diseases, that is, can be used as antimicrobial agents.

As described above, according to another aspect of the present invention, there is provided a method for treating or preventing a bacterial infectious disease or a symptom related thereto, comprising the step of administering an effective amount of a compound of formula (I) or a pharmaceutically acceptable salt thereof according to the present invention to a patient requiring such treatment or prevention.

The term "effective amount" as used herein means an amount of an active component at least necessary for attaining the effect of treatment, prevention, progress suppression, or amelioration of a disease or a symptom or a condition. The term "patient" as used herein means humans or mammals excluding humans, as objects to which a compound or composition according to the present invention can be administered, for example, mice, rats, rabbits, dogs, cats, cattles, horses, pigs, and monkeys. The term "administration" means the introduction of a contemplated substance into the body of a patient as an object either orally or parenterally.

Further, according to the present invention, there is provided an antimicrobial agent comprising a compound according to the present invention or a pharmacologically acceptable salt thereof as an active component.

A compound or a pharmacologically acceptable salt thereof according to the present invention can be administered to human and non-human animals orally or parenterally by administration routes, for example, intravenous administration, intramuscular administration, subcutaneous administration, rectal administration, or percutaneous administration.

Therefore, the pharmaceutical composition comprising a compound according to the present invention may be formulated into suitable dosage forms according to the administration routes. Specifically, oral preparations include tablets, capsules, powders, granules, pills, fine subtilaes, troches, and syrups, and parenteral preparations include injections such as intravenous injections and intramuscular injections, suppositories, tapes, and ointments.

These various preparations may be prepared by conventional methods, for example, with commonly used additives (carriers) such as excipients, extenders, disintegrants, binders, lubricants, colorants, diluents, wetting agents, surfactants, dispersants, buffering agents, preservatives, solubilizers, antiseptics, corrigents, soothing agent, and stabilizers.

Excipients include, for example, lactose, fructose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose or its salt, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils. Other usable nontoxic additives include, for example, syrup, vaseline, lanoline, glycerin, ethanol, propylene glycol, citric acid, sodium chloride, sodium sulfite, sodium phosphate, β-cyclodextrin, hydroxypropyl-β-cyclodextrin, and Tween 80.

In preparing the above injections, if necessary, buffering agents, pH adjustors, stabilizers, tonicity adjusting agents, and preservatives may be added.

The content of a compound according to the present invention in the pharmaceutical composition according to the present invention may vary according to the dosage form. The content, however, is generally 0.01 to 90% by weight, preferably 0.1 to 100% by weight, more preferably 0.5 to 50% by weight, based on the whole composition.

The dose may be appropriately determined in consideration of particular conditions, for example, the age, weight, sex, type of disease, and severity of condition of patients. For example, for the treatment of infectious diseases by oral administration, the preparation may be administered, for example, usually in an amount of about 1 to 2000 mg, preferably 10 to 1000 mg per day per adult. This dose may be administered at a time daily or divided doses of 2 to 6 times daily depending upon the condition of the patient.

Compounds according to the present invention may be administered in a formulation or in combination, for example, with a DHP-1 inhibitor (a dehydrogenase-1inhibitor) such as cilastatin or an organic ion transport inhibitor such as betamipron.

The present invention is further illustrated by the following Examples that are not intended as a limitation of the invention.

EXAMPLES

Example 1

4-Hydroxymethyl-5-((Z)-2-tritylthioethen-1-yl)thiazole a) 2-Amino-4-ethoxycarbonyl-5-iodothiazole A solution of 14.53 g of 2-amino-4-ethoxycarbonylthiazole in 200 ml of THF was cooled in ice under an argon atmosphere, 20.0 g of N-iodosuccinimide was added to the cooled solution, and the mixture was stirred at the same temperature for 1.5 hr. Brine was added to the reaction solution, and the mixture was extracted with ethyl acetate. The organic layer was dried over anhydrous magnesium sulfate, was filtered, and was concentrated under the reduced pressure. The residue was purified by column chromatography on silica gel (hexane:ethyl acetate=1:1 to 1:2) to give 21.12 g of 2-amino-4-ethoxycarbonyl-5-iodothiazole.

NMR (CDCl$_3$) δ: 1.41 (3H, t, J=7.2 Hz), 4.39 (2H, q, J=7.2 Hz), 5.4 (2H, br s)

b) 4-Ethoxycarbonyl-5-iodothiazole

A solution of 10.68 g of 2-amino-4-ethoxycarbonyl-5-iodothiazole in 140 ml of DMF was cooled in ice under an argon atmosphere. t-Butylnitrite (6.15 ml) was added to the cooled solution, and the mixture was stirred at room temperature for 30 min. The reaction solution was poured into brine, and the mixture was extracted three times with ethyl acetate. The organic layers were combined, followed by washing three times with brine. The organic layer was dried over anhydrous magnesium sulfate, was filtered, and was concentrated under the reduced pressure. The residue was purified by column chromatography on silica gel (hexane:ethyl acetate=5:1 to 3:1) to give 5.08 g of 4-ethoxycarbonyl-5-iodothiazole.

NMR (CDCl$_3$) δ: 1.45 (3H, t, J=7.2 Hz), 4.46 (2H, q, J=7.2 Hz), 8.94 (1H, s)

c) 5-Ethynyl-4-methoxycarbonylthiazole

4-Ethoxycarbonyl-5-iodothiazole (71.47 g) was dissolved in 250 ml of DMF. Triethylamine (70 ml), 53.4 ml of ethynyltrimethylsilane, 960 mg of copper(I) iodide, and 3.54 g of bis(triphenylphosphine) palladium(II) dichloride were added in that order, and the mixture was stirred at 60° C. under an argon atmosphere for 1.5 hr. The reaction solution was added to 1000 ml of ethyl acetate and 500 ml of brine. The mixture was adjusted to pH 3 by the addition of 1 N aqueous hydrochloric acid. The organic layer was separated and was washed with 500 ml of sodium bicarbonate water and 500 ml of brine in that order. The organic layer was dried over anhydrous magnesium sulfate, was filtered, and was concentrated under the reduced pressure. The residue was purified by column chromatography on silica gel (hexane:ethyl acetate=4:1 to 3:1) to give 53.66 g of 5-(2-trimethylsilylethynyl)-4-ethoxycarbonylthiazole. This product was dissolved in 250 ml of methanol, 3.1 of potassium carbonate was added to the solution under ice cooling, and the mixture was stirred at the same temperature for 45 min. The reaction solution was added to 500 ml of ethyl acetate and 250 ml of brine. The organic layer was separated and was washed twice with 500 ml of brine. The organic layer was dried over anhydrous magnesium sulfate, was filtered, and was concentrated under the reduced pressure. The residue was purified by column chromatography on silica gel (hexane:ethyl acetate=2:1 to 1:1) to give 29.91 g of 5-ethynyl-4-methoxycarbonylthiazole.

NMR (CDCl$_3$) δ: 3.86 (1H, s), 4.00 (3H, s), 8.72 (1H, s)

d) 5-Ethynyl-4-hydroxymethylthiazole

A 1.0 M diisobutylaluminum hydride/toluene solution (165 ml) was added dropwise to a solution of 25.05 g of 5-ethynyl-4-methoxycarbonylthiazole in 450 ml of toluene under an argon atmosphere at −40° C. The mixture was stirred at the same temperature for one hr. Thereafter, the reaction solution was poured into brine, and 200 ml of 1 N aqueous hydrochloric acid was added thereto. The insolubles were removed by filtration through Celite, and the filtrate was extracted four times with ethyl acetate. The organic layer was dried over anhydrous magnesium sulfate, was filtered, and was concentrated under the reduced pressure. The residue was dissolved in 300 ml of ethanol and 150 ml of THF. Sodium borohydride (2.2 g) was added to the solution in an argon atmosphere, under ice cooling, and the mixture was stirred at room temperature for one hr. Brine was added to the reaction solution, the mixture was adjusted to pH 3 by the addition of 1 N aqueous hydrochloric acid, and the organic solvent was removed by distillation under the reduced pressure. The residue was extracted three times with ethyl acetate. The extract was dried over anhydrous magnesium sulfate, was filtered, and was concentrated under the reduced pressure. The residue was purified by column chromatography on silica gel (chloroform:ethyl acetate=3:1 to 1:1) to give 19.25 g of 5-ethynyl-4-hydroxymethylthiazole.

NMR (CDCl$_3$) δ: 2.75 (1H, br s), 3.60 (1H, s), 4.86 (2H, s), 8.68 (1H, s)

e) 4-Hydroxymethyl-5-((Z)-2-tritylthioethen-1-yl)thiazole

A solution of 2.73 g of 5-ethynyl-4-hydroxymethylthiazole in 65 ml of THF was cooled in ice under an argon atmosphere, and 6.5 g of triphenylmethane thiol and 440 mg of potassium-t-butoxide were added to the cooled solution. The mixture was stirred at room temperature for 2 hr. Brine was added to the reaction solution, and the mixture was extracted twice with ethyl acetate. The organic layers were combined, were washed with brine, were then dried over anhydrous magnesium sulfate, were filtered, and were concentrated under the reduced pressure. Ethyl acetate (10 ml) and 10 ml of hexane were added to the residue, and the resultant precipitate was collected by filtration to give 7.26 of the title compound.

NMR (DMSO-d$_6$) δ: 4.58 (2H, d, J=4.8 Hz), 5.17 (3H, t, J=4.8 Hz), 5.88 (1H, d, J=10.8 Hz), 6.94 (1H, d, J=10.8 Hz), 7.2-7.4 (15H, m), 8.99 (1H, s)

Example 2

4-(2-Hydroxyethoxy)methyl-5-((Z)-2-tritylthioethen-1-yl)thiazole a) 4-Chloromethyl-5-((Z)-2-tritylthioethen-1-yl)thiazole A solution of 816 mg of 4-hydroxymethyl-5-((Z)-2-tritylthioethen-1-yl)thiazole prepared in step e) in Example 1 in 25 ml of THF was cooled in ice, and 0.301 ml of triethylamine and 0.157 ml of thionyl chloride were added to the cooled solution under an argon atmosphere. The mixture was stirred at the same temperature for 20 min, brine was then added to the reaction solution, and the mixture was adjusted to pH 8 by the addition of sodium bicarbonate water. The mixture was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane:ethyl acetate=5:1 to 1:1) to give 512 mg of 4-chloromethyl-5-((Z)-2-tritylthioethen-1-yl)thiazole.

NMR (CDCl$_3$) δ: 4.77 (2H, s), 6.11 (1H, d, J=10.5 Hz), 6.64 (1H, d, J=10.5 Hz), 7.2-7.4 (15H, m), 8.71 (1H, s)

b) 4-(2-Hydroxyethoxy)methyl-5-((Z)-2-tritylthioethen-1-yl)thiazole

4-Chloromethyl-5-((Z)-2-tritylthioethen-1-yl)thiazole (5.57 g) was suspended in 100 ml of THF and 30 ml of ethylene glycol, 1.5 g of sodium hydride was added to the suspension, and the mixture was stirred at 50° C. for 37 hr. Brine was added to the reaction solution, and the mixture was extracted twice with ethyl acetate. The organic layers were combined, were washed twice with brine, were dried over anhydrous magnesium sulfate, were filtered, and were concentrated under the reduced pressure. The residue was purified by column chromatography on silica gel (ethyl acetate) to give 4.87 g of the title compound.

NMR (CDCl$_3$) δ: 3.6-3.7 (2H, m), 3.7-3.8 (2H, m), 4.73 (2H, s), 6.03 (1H, d, J=10.8 Hz), 6.68 (1H, d, J=10.8 Hz), 7.2-7.4 (15H, m), 8.72 (1H, s)

Example 3

4-N,N-Dimethylcarbamoyl-5-((Z)-2-tritylthioethen-1-yl)thiazole a) 4-Methoxycarbonyl-5-((Z)-2-tritylthioethen-1-yl)thiazole and 4-methoxycarbonyl-5-((E)-2-tritylthioethen-1-yl)thiazole In the same manner as in step e) in Example 1, 7.67 g of 4-methoxycarbonyl-5-((Z)-2-tritylthioethen-1-yl)thiazole was produced from 3.96 g of 5-ethynyl-4-methoxycarbonylthiazole.

NMR (CDCl$_3$) δ: 3.93 (3H, s), 6.31 (1H, d, J=11.2 Hz), 7.26-7.34 (15H, m), 7.67 (1H, d, J=11.2 Hz), 8.69 (1H, s)

The residue provided by concentrating the filtrate in the crystallization was recrystallized from chloroform-methanol-hexane to give 502 mg of 4-methoxycarbonyl-5-((E)-2-tritylthioethen-1-yl)thiazole.

NMR (CDCl$_3$) δ: 3.93 (3H, s), 6.35 (1H, d, J=15.9 Hz), 7.25-7.35 (15H, m), 7.70 (1H, d, J=15.9 Hz), 8.38 (1H, s)

b) 4-Carboxy-5-((Z)-2-tritylthioethen-1-yl)thiazole

A 5 N aqueous sodium hydroxide solution (8.30 ml) was added to a suspension of 7.31 g of 4-methoxycarbonyl-5-((Z)-2-tritylthioethen-1-yl)thiazole in THF, and the mixture was stirred at 60° C. for one hr. The mixture was then cooled to room temperature, and 8.50 ml of 5 N hydrochloric acid, 100 ml of ethyl acetate, and 50 ml of water were added thereto, followed by concentration to 150 ml. Hexane (100 ml) was added to the concentrate, and the precipitated solid was collected by filtration and was washed with ethyl acetate-hexane (2:1) to give 8.30 g of 4-carboxy-5-((Z)-2-tritylthioethen-1-yl)thiazole.

NMR (DMSO-d$_6$) δ: 6.24 (1H, d, J=11.0 Hz), 7.23-7.41 (15H, m), 7.58 (1H, d, J=11.0 Hz), 9.04 (1H, s)

c) 4-N,N-Dimethylcarbamoyl-5-((Z)-2-tritylthioethen-1-yl)thiazole

1-[3-(Dimethylamino)propyl]-3-ethylcarbodiimide hydrochloride (3.91 g) and 3.14 g of 1-hydroxybenzotriazole were added to a suspension of 7.34 g of 4-carboxy-5-((Z)-2-tritylthioethen-1-yl)thiazole in 100 ml of DMF, and the mixture was stirred at room temperature for 30 min. A 2 M THF solution (25.6 ml) of dimethylamine was added thereto, and the mixture was stirred at the same temperature for 9 hr. Ethyl acetate (400 ml) was added to the reaction solution, and the mixture was washed four times with 400 ml of brine and was dried over anhydrous magnesium sulfate. The solvent was removed by distillation under the reduced pressure, and the residue was recrystallized from ethyl acetate-hexane to give 5.73 g of the title compound.

NMR (CDCl$_3$) δ: 2.96 (3H, s), 3.09 (3H, s), 6.06 (1H, d, J=10.8 Hz), 6.86 (1H, d, J=10.8 Hz), 7.23-7.34 (15H, m), 8.69 (1H, s)

Example 4

4-Hydroxymethyl-2-((Z)-2-tritylthioethen-1-yl)thiazole a) 4-Ethoxycarbonyl-2-iodothiazole

A solution of 6.0 ml of t-butyl nitrite in 120 ml of acetonitrile was cooled in ice under an argon atmosphere, and 9.64 g of diiodomethane and 5.16 g of 2-amino-4-ethoxycarbonylthiazole were added to the cooled solution. The mixture was stirred at room temperature for one hr, brine was added thereto, and the mixture was extracted twice with ethyl acetate. The organic layers were combined, were washed twice with brine, were dried over anhydrous magnesium sulfate, were filtered, and were concentrated under the reduced pressure. The residue was purified by column chromatography on silica gel (hexane:ethyl acetate=5:1 to 3:1) to give 5.58 g of 4-ethoxycarbonyl-2-iodothiazole.

NMR (CDCl$_3$) δ: 1.41 (3H, t, J=7.2 Hz), 4.43 (2H, q, J=7.2 Hz), 8.14 (1H, s)

b) 2-Ethynyl-4-methoxycarbonylthiazole

4-Ethoxycarbonyl-2-iodothiazole (6.39 g) was suspended in 60 ml of triethylamine, and 253 mg of palladium acetate and 592 mg of triphenylphosphine, and 6.37 ml of ethynyltrimethylsilane were added to the suspension under an argon atmosphere, followed by stirring at 80° C. for 2 hr. The reaction solution was concentrated under the reduced pressure, ethyl acetate and brine were added to the concentrate, and the mixture was adjusted to pH 3.0 by the addition of 1 N aqueous hydrochloric acid. The mixture was extracted twice with ethyl acetate and was washed with brine. The organic layer was dried over anhydrous magnesium sulfate, was filtered, and was concentrated under the reduced pressure. The residue was purified by column chromatography on silica gel (hexane:ethyl acetate=5:1) to give 3.97 g of 2-(2-trimethylsilylethynyl)-4-ethoxycarbonylthiazole. This compound was dissolved in 30 ml of methanol, and the solution was cooled in ice. Potassium carbonate (220 mg) was added to the cooled solution, and the mixture was stirred at room temperature for 30 min. Brine was added to the reaction solution, and the mixture was extracted twice with ethyl acetate and was washed with brine. The organic layer was dried over anhydrous magnesium sulfate, was filtered, and was concentrated under the reduced pressure to give 2.50 g of 2-ethynyl-4-methoxycarbonylthiazole.

NMR (CDCl$_3$) δ: 3.51 (1H, s), 3.97 (3H, s), 8.20 (1H, s)

c) 4-Methoxycarbonyl-2-((Z)-2-tritylthioethen-1-yl)thiazole

2-Ethynyl-4-methoxycarbonylthiazole (2.50 g) was dissolved in 70 ml of THF. Triphenylmethylmercaptan (4.96 g) and 336 mg of potassium-t-butoxide were added to the solution at −60° C. under an argon atmosphere. The mixture was stirred at the same temperature for one hr. An aqueous ammonium chloride solution was added to the reaction solution, and the mixture was extracted twice with ethyl acetate. The organic layers were combined, were washed with brine, were then dried over anhydrous magnesium sulfate, were filtered, and were concentrated under the reduced pressure. The residue was purified by column chromatography on silica gel (hexane:ethyl acetate=5:1). Ethyl acetate and hexane were added to a crude product containing a target compound, and the precipitate was collected by filtration to give 3.88 g of 4-methoxycarbonyl-2-((Z)-2-tritylthioethen-1-yl)thiazole.

NMR (CDCl$_3$) δ: 3.96 (3H, s), 6.46 (1H, d, J=11.1 Hz), 6.85 (1H, d, J=11.1 Hz), 7.2-7.4 (15H, m), 8.22 (1H, s)

d) 4-Hydroxymethyl-2-((Z)-2-tritylthioethen-1-yl)thiazole

A solution of 3.48 g of 4-methoxycarbonyl-2-((Z)-2-tritylthioethen-1-yl)thiazole in 70 ml of dichloromethane was cooled in ice, and 18.7 ml of a 1.0 M diisobutylaluminum hydride/toluene solution was added dropwise to the cooled solution under an argon atmosphere. The mixture was stirred at the same temperature for one hr. Water was then added to the reaction solution, and the mixture was adjusted to pH 2.5 by the addition of 1 N aqueous hydrochloric acid. The insolubles were removed by filtration through Celite, and the filtrate was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane: ethyl acetate=1:1) to give 2.88 g of the title compound.

NMR (CDCl$_3$) δ: 4.79 (2H, s), 6.35 (1H, d, J=10.8 Hz), 6.68 (1H, d, J=10.8 Hz), 7.21 (1H, s), 7.25-7.4 (15H, m)

Example 5

4-Methyl-5-((Z)-2-tritylthioethen-1-yl)thiazole

In the same manner as in step e) in Example 1, 1.98 g of the title compound was prepared from 1.14 g of 4-methyl-5-ethynylthiazole.

NMR (CDCl$_3$) δ: 2.45 (3H, s), 5.90 (1H, d, J=10.8 Hz), 6.53 (1H, d, J=10.8 Hz), 7.26-7.35 (15H, m), 8.66 (1H, s)

Example 6

4-Carbamoyl-5-((Z)-2-tritylthioethen-1-yl)thiazole a) 4-Carbamoyl-5-ethynylthiazole Bis(benzonitrile)palladium(II) dichloride (227 mg), 239 mg of tri-tert-butylphosphine, 75 mg of copper(I) iodide, 5.55 ml of trimethylsilylacetylene, and 4.14 ml of N,N-diisopropylamine were added to a solution of 5.02 g of 4-carbamoyl-5-iodothiazole in dioxane, and the mixture was stirred at 40° C. for one day. Ethyl acetate and semi-saturated brine were added to the reaction solution, followed by separation. The organic layer was dried over anhydrous magnesium sulfate. The solvent was removed by distillation under the reduced pressure. The residue was recrystallized from dichloromethane-hexane to give a light brown solid, and 20 ml of 30% aqueous ammonia and 10 ml of THF were added to the solid. The mixture was stirred at room temperature for one hr and was concentrated to remove the solvent, and the concentrate was recrystallized from dichloromethane-ethyl acetate to give 474 mg of 4-carbamoyl-5-ethynylthiazole.

NMR (DMSO-d$_6$) δ: 4.95 (1H, s), 7.65 (1H, br s), 7.77 (1H, s), 9.08 (1H, s)

b) 4-Carbamoyl-5-((Z)-2-tritylthioethen-1-yl)thiazole

In the same manner as in step e) in Example 1, 1.77 g of the title compound was prepared from 740 mg of 4-carbamoyl-5-ethynylthiazole.

NMR (DMSO-d$_6$) δ: 6.14 (1H, d, J=11.0 Hz), 7.20-7.43 (15H, m), 7.58 (1H, br s), 7.81-7.90 (2H, m), 9.05 (1H, s)

Example 7

4-N-Methylcarbamoyl-5-((Z)-2-tritylthioethen-1-yl)thiazole

In the same manner as in step c) in Example 3, 397 mg of the title compound was prepared from 430 mg of 4-carboxy-5-((Z)-2-tritylthioethen-1-yl)thiazole and 1.0 ml of a 2.0 M solution of methylamine in THF.

NMR (CDCl$_3$) δ: 2.97 (3H, d, J=5.1 Hz), 6.20 (1H, d, J=11.0 Hz), 7.25-7.33 (15H, m), 7.54 (1H, br s), 7.99 (1H, d, J=11.0 Hz), 8.57 (1H, s)

Example 8

4-N-Cyanomethyl-N-methylcarbamoyl-5-((Z)-2-tritylthioethen-1-yl)thiazole

In the same manner as in step c) in Example 3, 781 mg of the title compound was prepared from 1.10 g of 4-carboxy-5-((Z)-2-tritylthioethen-1-yl)thiazole and 0.392 ml of 2-methylaminoacetonitrile.

NMR (DMSO-d$_6$) δ: 2.97-3.07 (3H, m), 4.48-4.58 (2H, m), 6.13 (1H, d, J=10.9 Hz), 6.82-6.96 (2H, m), 7.22-7.43 (15H, m), 9.12-9.17 (1H, m)

Example 9

4-N-cyanomethylcarbamoyl-5-((Z)-2-tritylthioethen-1-yl)thiazole

In the same manner as in step c) in Example 3, 1.24 g of the title compound was prepared from 1.41 g of 4-carboxy-5-((Z)-2-tritylthioethen-1-yl)thiazole and 609 mg of aminoacetonitrile (hydrochloride).

NMR (DMSO-d$_6$) δ: 4.23 (2H, d, J=5.9 Hz), 6.25 (1H, d, J=11.2 Hz), 7.23-7.43 (15H, m), 7.83 (1H, d, J=10.8 Hz), 9.12 (1H, s), 9.18 (1H, t, J=5.9 Hz)

Example 10

4-N-(2-Cyanoethyl)carbamoyl-5-((Z)-2-tritylthioethen-1-yl)thiazole

In the same manner as in step c) in Example 3, 439 mg of the title compound was prepared from 430 mg of 4-carboxy-5-((Z)-2-tritylthioethen-1-yl)thiazole and 0.148 ml of 2-cyanoethanol.

NMR (CDCl$_3$) δ: 2.70 (2H, t, J=6.6 Hz), 3.68 (2H, m), 6.25 (1H, d, J=11.2 Hz), 7.27-7.34 (15H, m), 7.90 (1H, d, J=11.2 Hz), 7.96 (1H, br t, J=6.3 Hz), 8.60 (1H, s)

Example 11

4-Cyanomethyl-5-((Z)-2-tritylthioethen-1-yl)thiazole

A suspension of 350 mg of 4-chloromethyl-5-((Z)-2-tritylthioethen-1-yl)thiazole, prepared in step a) in Example 2, in 7 ml of DMF was cooled in ice, and 94 mg of sodium cyanide was added to the cooled suspension under an argon atmosphere. The mixture was stirred at room temperature for 2.5 hr, and brine was then added to the reaction solution. The mixture was extracted twice with ethyl acetate, and the organic layers were combined, followed by washing with brine. The washed organic layer was dried over anhydrous magnesium sulfate, was filtered, and was concentrated under the reduced pressure. The residue was purified by column chromatography on silica gel (hexane:ethyl acetate=5:1) to give 132 mg of the title compound.

NMR (CDCl$_3$) δ: 3.87 (2H, s), 6.13 (1H, d, J=10.8 Hz), 6.47 (1H, d, J=10.8 Hz), 7.2-7.4 (15H, m), 8.72 (1H, s)

Example 12

4-(2-Methoxyethoxy)methyl-5-((Z)-2-tritylthioethen-1-yl)thiazole

In the same manner as in step b) in Example 2, 461 mg of the title compound was prepared from 436 mg of 4-chloromethyl-5-((Z)-2-tritylthioethen-1-yl)thiazole prepared in step a) in Example 2 and 7 ml of 2-methoxyethanol.

NMR (CDCl$_3$) δ: 3.34 (3H, s), 3.5-3.6 (2H, m), 3.6-3.7 (2H, m), 4.74 (2H, s), 6.00 (1H, d, J=11.1 Hz), 6.77 (1H, d, J=11.1 Hz), 7.2-7.4 (15H, m), 8.69 (1H, s)

Example 13

4-(3-Cyanoazetidin-1-yl)carbonyl-5-((Z)-2-tritylthioethen-1-yl)thiazole

In the same manner as in step c) in Example 3, 716 mg of the title compound was prepared from 859 mg of 4-carboxy-5-((Z)-2-tritylthioethen-1-yl)thiazole and 237 mg of 3-cyanoazetidine hydrochloride.

NMR (CDCl$_3$) δ: 3.44-3.52 (1H, m), 4.34-4.39 (1H, m), 4.41-4.47 (1H, m), 4.77-4.81 (1H, m), 4.86-4.91 (1H, m), 6.24 (1H, d, J=11.2 Hz), 7.27-7.34 (15H, m), 7.78 (1H, d, J=11.2 Hz), 8.61 (1H, s)

Example 14

4-N-(2-Hydroxyethyl)carbamoyl-5-((Z)-2-tritylthioethen-1-yl)thiazole

In the same manner as in step c) in Example 3, 871 mg of the title compound was prepared from 859 mg of 4-carboxy-5-((Z)-2-tritylthioethen-1-yl)thiazole and 0.24 ml of 2-aminoethanol.

NMR (CDCl$_3$) δ: 2.80 (1H, br t, J=5.4 Hz), 3.56-3.61 (2H, m), 3.79-3.83 (2H, m), 6.23 (1H, d, J=11.0 Hz), 7.26-7.33 (15H, m), 7.95 (1H, d, J=11.0 Hz), 7.96 (1H, br s), 8.59 (1H, s)

Example 15

4-N-(3-Hydroxypropan-1-yl)carbamoyl-5-((Z)-2-tritylthio ethen-1-yl)thiazole

In the same manner as in step c) in Example 3, 666 mg of the title compound was prepared from 644 mg of 4-carboxy-5-((Z)-2-tritylthioethen-1-yl)thiazole and 0.137 ml of 3-aminopropanol.

NMR (CDCl$_3$) δ: 1.75 (2H, m), 3.41 (1H, br t, J=6.6 Hz), 3.55-3.60 (2H, m), 3.61-3.66 (2H, m), 6.23 (1H, d, J=11.2 Hz), 7.26-7.33 (15H, m), 7.80 (1H, br t), 7.96 (1H, d, J=11.2 Hz), 8.59 (1H, s)

Example 16

4-N-(2-Hydroxyethyl)-N-methylcarbamoyl-5-((Z)-2-tritylthioethen-1-yl)thiazole

In the same manner as in step c) in Example 3, 651 mg of the title compound was prepared from 644 mg of 4-carboxy-5-((Z)-2-tritylthioethen-1-yl)thiazole and 0.145 ml of 2-(methylamino)ethanol.

NMR (CDCl$_3$) δ: 3.05 & 3.11 (total 3H, both s, N—Me conformer), 3.46-3.48 (2H, m), 3.82-3.84 (2H, m), 5.25 (1H, br t), 6.13 (1H, d, J=11.0 Hz), 7.07 (1H, d, J=11.0 Hz), 7.27-7.32 (15H, m), 8.68 (total 1H, both s, thiazole H (2) conformer)

Example 17

4-(Azetidin-1-yl)carbonyl-5-((Z)-2-tritylthioethen-1-yl)thiazole

In the same manner as in step c) in Example 3, 594 mg of the title compound was prepared from 644 mg of 4-carboxy-5-((Z)-2-tritylthioethen-1-yl)thiazole and 168 mg of azetidine hydrochloride.

NMR (CDCl$_3$) δ: 2.24-2.32 (2H, m), 4.15-4.19 (2H, m), 4.48-4.52 (2H, m), 6.15 (1H, d, J=11.0 Hz), 7.24-7.31 (15H, m), 7.73 (1H, d, J=11.0 Hz), 8.61 (1H, s)

Example 18

4-(3-Hydroxyazetidin-1-yl)carbonyl-5-((Z)-2-tritylthioethen-1-yl)thiazole

In the same manner as in step c) in Example 3, 0.742 g of the title compound was prepared from 0.957 g of 4-carboxy-5-((Z)-2-tritylthioethen-1-yl)thiazole and 0.757 g of 3-hydroxyazetidine tartrate.

NMR (CDCl$_3$) δ: 2.68 (1H, d, J=6.1 Hz), 3.99 (1H, m), 4.31-4.41 (2H, m), 4.60-4.74 (2H, m), 6.18 (1H, d, J=11.2 Hz), 7.23-7.33 (15H, m), 7.71 (1H, d, J=11.1 Hz), 7.57 (1H, 2s)

Example 19

4-(3-Hydroxypropan-1-yloxy)methyl-5-((Z)-2-tritylthioethen-1-yl)thiazole

In the same manner as in step b) in Example 2, 674 mg of the title compound was prepared from 665 mg of 4-chloromethyl-5-((Z)-2-tritylthioethen-1-yl)thiazole prepared in step a) in Example 2 and 3 ml of 1,3-propanediol.

NMR (CDCl$_3$) δ: 1.8-1.9 (2H, m), 3.6-3.8 (4H, m), 4.68 (2H, s), 6.02 (1H, d, J=11.1 Hz), 6.68 (1H, d, J=11.1 Hz), 7.2-7.4 (15H, m), 8.71 (1H, s)

Example 20

2-Amino-4-carbamoyl-5-((Z)-2-tritylthioethen-1-yl)thiazole a) 2-Amino-4-ethoxycarbonyl-5-ethynylthiazole 2-Amino-4-ethoxycarbonyl-5-iodothiazole (1.40 g) prepared in step a) in Example 1 was dissolved in 20 ml of N-methyl-2-pyrrolidinone. tri-n-butylethynyltin (1.63 ml), 127 mg of tri(2-furyl)phosphine, 127 mg of tris(dibenzylideneacetone)dipalladium(0), and 1.27 g of zinc chloride were added to the solution under an argon atmosphere, and the mixture was stirred at room temperature for 2.5 hr. Brine and ethyl acetate were added to the reaction solution. The insolubles were removed by filtration through Celite, and the filtrate was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane: ethyl acetate=3:1) to give 597 mg of 2-amino-4-ethoxycarbonyl-5-ethynylthiazole.

NMR (CDCl$_3$) δ: 1.39 (3H, t, J=6.9 Hz), 3.67 (1H, s), 4.39 (2H, q, J=6.9 Hz), 5.55 (2H, br s)

b) 2-Amino-4-ethoxycarbonyl-5-((Z)-2-tritylthioethen-1-yl)thiazole

In the same manner as in step e) in Example 1, 1.93 g of 2-amino-4-ethoxycarbonyl-5-((Z)-2-tritylthioethen-1-yl)thiazole was prepared from 992 mg of 2-amino-4-ethoxycarbonyl-5-ethynylthiazole.

NMR (CDCl$_3$) δ: 1.36 (3H, t, J=6.9 Hz), 4.35 (2H, q, J=6.9 Hz), 5.03 (2H, br s), 5.94 (1H, d, J=11.1 Hz), 7.2-7.4 (15H, m), 7.52 (1H, d, J=11.1 Hz), 8.02 (1H, s)

c) 2-Amino-4-carbamoyl-5-((Z)-2-tritylthioethen-1-yl)thiazole

In the same manner as in step b) in Example 3 and step c) in Example 3, 197 mg of the title compound was prepared from 501 mg of 2-amino-4-ethoxycarbonyl-5-((Z)-2-tritylthioethen-1-yl)thiazole and 8 ml of a 0.5 M ammonia/dioxane solution.

NMR (CDCl$_3$) δ: 4.87 (2H, br s), 5.42 (1H, br s), 5.88 (1H, d, J=11.1 Hz), 7.06 (1H, br s), 7.2-7.4 (15H, m), 7.77 (1H, d, J=11.1 Hz)

Example 21

4-Hydroxymethyl-5-((E)-2-tritylthioethen-1-yl)thiazole

In the same manner as in step d) in Example 4, 330 mg of the title compound was prepared from 480 mg of 4-methoxycarbonyl-5-((E)-2-tritylthioethen-1-yl)thiazole prepared in step a) in Example 3.

NMR (CDCl$_3$) δ: 2.25 (1H, t, J=5.8 Hz), 4.62 (2H, d, J=5.8 Hz), 6.11 (1H, d, J=15.6 Hz), 6.78 (1H, d, J=15.6 Hz), 7.24-7.35 (15H, m), 8.71 (1H, s)

Example 22

2-Carbamoyl-5-((Z)-2-tritylthioethen-1-yl)thiazole a) 2-Carbamoyl-5-ethynylthiazole In the same manner as in step c) in Example 1, 1.11 g of 2-carbamoyl-5-ethynylthiazole was prepared from 1.70 g of 2-carbamoyl-5-iodothiazole.

NMR (DMSO-d$_6$) δ: 4.97 (1H, s), 8.90 (1H, br s), 8.23 (1H, s), 8.29 (1H, br s)

b) 2-Carbamoyl-5-((Z)-2-tritylthioethen-1-yl)thiazole

In the same manner as in step e) in Example 1, 2.88 g of the title compound was prepared from 1.11 g of 2-carbamoyl-5-ethynylthiazole.

NMR (DMSO-d$_6$) δ: 6.06 (1H, d, J=11 Hz), 6.88 (1H, d, J=11 Hz), 7.22-7.43 (15H, m), 7.85 (1H, br s), 8.00 (1H, s), 8.16 (1H, br s)

Example 23

2-Amino-5-((Z)-2-tritylthioethen-1-yl)thiazole a) 2-Amino-5-ethynylthiazole

Tri-n-butylethynyltin (1.93 ml) and 292 mg of bis(triphenylphosphine)palladium(II) dichloride were added to 30 ml of a suspension of 1.00 g of 2-amino-5-bromothiazole in xylene, and the mixture was stirred at 80° C. for one hr, at 100° C. for 30 min, and at 120° C. for 30 min. The reaction solution was concentrated, and the residue was purified by column chromatography on silica gel (ethyl acetate:hexane=1:1) to give 1.70 mg of 2-amino-5-ethynylthiazole.

NMR (CDCl$_3$) δ: 3.30 (1H, s), 5.20 (2H, br s), 7.25 (1H, s)

b) 2-Amino-5-((Z)-2-tritylthioethen-1-yl)thiazole

In the same manner as in step e) in Example 1, 616 mg of the title compound was prepared from 275 mg of 2-amino-5-ethynylthiazole.

NMR (CDCl$_3$) δ: 4.93 (2H, br s), 5.56 (1H, d, J=10.5 Hz), 6.41 (1H, d, J=10.5 Hz), 7.07 (1H, s), 7.23-7.36 (15H, m)

Example 24

2-N,N-Dimethylcarbamoyl-5-((Z)-2-tritylthioethen-1-yl)thiazole a) 2-N,N-Dimethylcarbamoyl-5-ethynylthiazole In the same manner as in step b) in Example 4, 3.13 g of 2-N,N-dimethylcarbamoyl-5-ethynylthiazole was prepared from 5.69 g of 2-N,N-dimethylcarbamoyl-5-iodothiazole.

NMR (CDCl$_3$) δ: 3.15 (3H, s), 3.52 (1H, s), 3.58 (3H, s), 7.92 (1H, s)

b) 2-N,N-Dimethylcarbamoyl-5-((Z)-2-tritylthioethen-1-yl)thiazole

In the same manner as in step e) in Example 1, 5.27 g of the title compound was prepared from 2.80 g of 2-N,N-dimethylcarbamoyl-5-ethynylthiazole.

NMR (CDCl$_3$) δ: 3.15 (3H, s), 3.58 (3H, s), 6.08 (1H, d, J=10.7 Hz), 6.54 (1H, d, J=10.7 Hz), 7.23-7.34 (15H, m), 7.79 (1H, s)

Example 25

4-Carbamoyl-2-((Z)-2-tritylthioethen-1-yl)thiazole a) 2-Bromo-4-carbamoylthiazole THF (10 ml) and 20 ml of 30% aqueous ammonia were added to 1.51 g of 2-bromo-4-ethoxycarbonylthiazole, and the mixture was stirred at room temperature for 3 days. The reaction solution was concentrated to give 1.31 g of 2-bromo-4-carbamoylthiazole.

NMR (DMSO-d$_6$) δ: 7.65 (1H, br s), 7.85 (1H, br s), 8.27 (1H, s)

b) 4-Carbamoyl-2-ethynylthiazole

In substantially the same manner as in step b) in Example 4, 209 mg of 4-carbamoyl-2-ethynylthiazole was prepared from 2.3 g of 2-bromo-4-carbamoylthiazole.

NMR (CDCl$_3$) δ: 3.54 (1H, s), 5.67 (1H, br s), 7.15 (1H, br s), 8.18 (1H, s)

c) 4-Carbamoyl-2-((Z)-2-tritylthioethen-1-yl)thiazole

In the same manner as in step e) in Example 1, 417 mg of the title compound was prepared from 209 mg of 4-carbamoyl-2-ethynylthiazole.

NMR (CDCl$_3$) δ: 5.58 (1H, br s), 6.45 (1H, d, J=11.1 Hz), 6.59 (1H, d, J=11.1 Hz), 7.22 (1H, br s), 7.26-7.34 (15H, m), 8.11 (1H, s)

Example 26

4-N-(2-Hydroxyethyl)carbamoyl-2-((Z)-2-tritylthioethen-1-yl)thiazole

4-Methoxycarbonyl-2-((Z)-2-tritylthioethen-1-yl)thiazole (443 mg) prepared in step c) in Example 4 was dissolved in 8 ml of THF, 1.2 ml of 2-aminoethanol was added to the solution, and the mixture was stirred at 50° C. for 8 hr. THF was removed by distillation under the reduced pressure, and the residue was adjusted to pH 2 by the addition of water and aqueous hydrochloric acid, followed by extraction twice with dichloromethane. The extract was dried over anhydrous magnesium sulfate, was filtered, and was concentrated under the reduced pressure. Ethyl acetate was added to the residue, and the resultant solid was collected by filtration to give 396 mg of the title compound.

NMR (DMSO-d$_6$) δ: 3.3-3.6 (4H, m), 4.83 (1H, t, J=5.4 Hz), 6.43 (1H, d, J=10.8 Hz), 6.86 (1H, d, J=10.8 Hz), 7.2-7.4 (15H, m), 8.11 (1H, t, J=6.0 Hz), 8.28 (1H, s)

Example 27

4-N,N-Dimethylcarbamoyl-2-((Z)-2-tritylthioethen-1-yl)thiazole a) 4-Carboxy-2-((Z)-2-tritylthioethen-1-yl)thiazole In the same manner as in step b) in Example 3, 2.33 g of 4-carboxy-2-((Z)-2-tritylthioethen-1-yl)thiazole was prepared from 2.65 g of 4-methoxycarbonyl-2-((Z)-2-tritylthioethen-1-yl)thiazole prepared in step c) in Example 4.

NMR (CDCl$_3$) δ: 6.38 (1H, d, J=10.8 Hz), 6.85 (1H, d, J=10.8 Hz), 7.23-7.42 (15H, m), 8.45 (1H, s)

b) 4-N,N-Dimethylcarbamoyl-2-((Z)-2-tritylthioethen-1-yl)thiazole

In the same manner as in step c) in Example 3, 854 mg of the title compound was prepared from 1.32 g of 4-carboxy-2-((Z)-2-tritylthioethen-1-yl)thiazole and 4.6 ml of 2 M-dimethylamine/THF solution.

NMR (CDCl$_3$) δ: 3.11 (3H, s), 3.40 (3H, s), 6.39 (1H, d, J=11.1 Hz), 6.61 (1H, d, J=11.1 Hz), 7.2-7.4 (15H, m), 7.93 (1H, s)

Example 28

4-N-Methylcarbamoyl-2-((Z)-2-tritylthioethen-1-yl)thiazole

Oxalyl dichloride (0.136 ml) and three drops of DMF were added to 10 ml of a solution of 625 mg of 4-carboxy-2-((Z)-2-tritylthioethen-1-yl)thiazole, prepared in step a) in Example 27, in THF, and the mixture was stirred at room temperature for 15 min. A 2 M-methylamine/THF solution (5 ml) was added thereto at the same temperature, and the mixture was stirred for 30 min. Ethyl acetate (50 ml) and 50 ml of semi-saturated brine were added thereto. The organic layer was then dried over anhydrous magnesium sulfate, the solvent was removed by distillation under the reduced pressure, and the residue was recrystallized from ethyl acetate-hexane to give 400 mg of the title compound.

NMR (CDCl$_3$) δ: 3.00 (3H, d, J=5.1 Hz), 6.43 (1H, d, J=10.7 Hz), 6.58 (1H, d, J=10.7 Hz), 7.25-7.35 (15H, m), 8.06 (1H, s)

Example 29

4-N-Cyanomethylcarbamoyl-2-((Z)-2-tritylthioethen-1-yl)thiazole

In the same manner as in step c) in Example 3, 69 mg of the title compound was prepared from 85 mg of 4-carboxy-2-((Z)-2-tritylthioethen-1-yl)thiazole and 46 mg of aminoacetonitrile sulfate.

NMR (CDCl$_3$) δ: 4.34 (2H, d, J=5.8 Hz), 6.48 (1H, d, J=10.9 Hz), 6.58 (1H, d, J=10.9 Hz), 7.25-7.40 (15H, m), 7.76 (1H, t, J=6.0 Hz), 8.13 (1H, s)

Example 30

4-N-Cyanomethyl-N-methylcarbamoyl-2-((Z)-2-tritylthioethen-1-yl)thiazole

In the same manner as in step c) in Example 3, 91 mg of the title compound was prepared from 85 mg of 4-carboxy-2-((Z)-2-tritylthioethen-1-yl)thiazole and 21 mg of N-methylaminoacetonitrile.

NMR (CDCl$_3$) δ: 3.20, 3.61 (total 3H, both s), 4.44, 5.38 (total 2H, both s), 6.44 (1H, d, J=10.9 Hz), 6.56 (1H, d, J=11.0 Hz), 7.24-7.32 (15H, m), 8.09, 8.18 (total 1H, both s)

Example 31

4-Cyanomethyl-2-((Z)-2-tritylthioethen-1-yl)thiazole

In the same manner as in step a) in Example 2 and Example 11, 2.614 g of the title compound was prepared from 2.801 g of 4-hydroxymethyl-2-((Z)-2-tritylthioethen-1-yl)thiazole.

NMR (CDCl$_3$) δ: 3.92 (2H, s), 6.40 (1H, d, J=11.0 Hz), 6.64 (1H, d, J=10.9 Hz), 7.26-7.38 (15H, m), 8.02 (1H, s)

Example 32

4-(3-Hydroxyazetidin-1-yl)carbonyl-2-((Z)-2-tritylthioethen-1-yl)thiazole

In the same manner as in step c) in Example 3, 1.169 g of the title compound was prepared from 1.300 g of 4-carboxy-2-((Z)-2-tritylthioethen-1-yl)thiazole and 1.028 g of 3-hydroxyazetidine tartrate.

NMR (CDCl$_3$) δ: 4.05 (1H, m), 4.44 (1H, m), 4.65 (2H, m), 5.08 (1H, m), 6.37 (1H, d, J=11.0 Hz), 6.48 (1H, d, J=10.9 Hz), 7.25-7.37 (15H, m), 8.09 (1H, s)

Example 33

4-(3-Cyanoazetidin-1-yl)carbonyl-2-((Z)-2-tritylthioethen-1-yl)thiazole

In the same manner as in step c) in Example 3, 0.271 g of the title compound was prepared from 0.356 g of 4-carboxy-2-((Z)-2-tritylthioethen-1-yl)thiazole and 0.149 g of 3-cyanoazetidine hydrochloride.

NMR (CDCl$_3$) δ: 3.48 (1H, m), 4.39-4.52 (2H, m), 5.14 (2H, m), 6.40 (1H, d, J=11.0 Hz), 6.48 (1H, d, J=11.0 Hz), 7.26-7.36 (15H, m), 8.13 (1H, s)

Example 34

5-Hydroxymethyl-2-((Z)-2-tritylthioethen-1-yl)thiazole a) 5-Ethoxycarbonyl-2-iodothiazole

In the same manner as in step a) in Example 4, 1.10 g of 5-ethoxycarbonyl-2-iodothiazole was prepared from 935 mg of 2-amino-5-ethoxycarbonylthiazole.

NMR (CDCl$_3$) δ: 1.37 (3H, t, J=7.2 Hz), 4.36 (2H, q, J=7.2 Hz), 8.10 (1H, s)

b) 5-Ethoxycarbonyl-2-ethynylthiazole

In the same manner as in step a) in Example 20, 218 mg of 5-ethoxycarbonyl-2-ethynylthiazole was prepared from 997 mg of 5-ethoxycarbonyl-2-iodothiazole.

NMR (CDCl$_3$) δ: 1.39 (3H, t, J=7.2 Hz), 3.59 (1H, s), 4.39 (2H, q, J=7.2 Hz), 8.37 (1H, s)

c) 5-Ethoxycarbonyl-2-((Z)-2-tritylthioethen-1-yl)thiazole

In the same manner as in step e) in Example 1, 531 mg of 5-ethoxycarbonyl-2-((Z)-2-tritylthioethen-1-yl)thiazole was prepared from 395 mg of 5-ethoxycarbonyl-2-ethynylthiazole.

NMR (CDCl$_3$) δ: 1.39 (3H, t, J=7.2 Hz), 4.38 (2H, q, J=7.2 Hz), 6.52 (1H, d, J=11.1 Hz), 6.69 (1H, d, J=11.1 Hz), 7.2-7.4 (15H, m), 8.40 (1H, s)

d) 5-Hydroxymethyl-2-((Z)-2-tritylthioethen-1-yl)thiazole

A solution of 257 mg of 5-ethoxycarbonyl-2-((Z)-2-tritylthioethen-1-yl)thiazole in 10 ml of THF was cooled in ice, and 1.69 ml of a 1.0 M diisobutylaluminum hydride/toluene solution was added dropwise to the cooled solution under an argon atmosphere. The mixture was stirred at room temperature for 2 hr. Water was added to the reaction solution, and the mixture was adjusted to pH 2.5 by the addition of 1 N aqueous hydrochloric acid. The insolubles were removed by filtration through Celite, and the filtrate was extracted twice with ethyl acetate. The organic layers were combined, were washed with brine, were dried over anhydrous magnesium sulfate, were filtered, and were concentrated under the reduced pressure to give 234 mg of the title compound.

NMR (CDCl$_3$) δ: 4.90 (2H, s), 6.33 (1H, d, J=11.1 Hz), 6.64 (1H, d, J=11.1 Hz), 7.2-7.4 (15H, m), 7.70 (1H, s)

Example 35

4,5-Dicarbamoyl-2-((Z)-2-tritylthioethen-1-yl)thiazole a) 4,5-Diethoxycarbonyl-2-iodothiazole

In the same manner as in step a) in Example 4, 662 mg of 4,5-diethoxycarbonyl-2-iodothiazole was prepared from 900 mg of 2-amino-4,5-diethoxycarbonylthiazole.

NMR (CDCl$_3$) δ: 1.36 (3H, t, J=7.2 Hz), 1.40 (3H, t, J=7.2 Hz), 4.36 (2H, q, J=7.2 Hz), 4.44 (2H, q, J=7.2 Hz)

b) 4,5-Diethoxycarbonyl-2-ethynylthiazole 4,5-Diethoxycarbonyl-2-ethynylthiazole (539 mg) was prepared from 1.16 g of 4,5-diethoxycarbonyl-2-iodothiazole in the same manner as in step b) in Example 4, except that ethanol was used as the solvent instead of methanol.

NMR (CDCl$_3$) δ: 1.37 (3H, t, J=7.2 Hz), 1.41 (3H, t, J=7.2 Hz), 3.60 (1H, s), 4.38 (2H, q, J=7.2 Hz), 4.45 (2H, q, J=7.2 Hz)

c) 4,5-Diethoxycarbonyl-2-((Z)-2-tritylthioethen-1-yl)thiazole

In the same manner as in step e) in Example 1, 440 mg of 4,5-diethoxycarbonyl-2-((Z)-2-tritylthioethen-1-yl)thiazole was prepared from 389 mg of 4,5-diethoxycarbonyl-2-ethynylthiazole.

NMR (CDCl$_3$) δ: 1.38 (3H, t, J=7.2 Hz), 1.41 (3H, t, J=7.2 Hz), 4.38 (2H, q, J=7.2 Hz), 4.45 (2H, q, J=7.2 Hz), 6.58 (1H, d, J=11.1 Hz), 6.77 (1H, d, J=11.1 Hz), 7.2-7.4 (15H, m)

d) 4,5-Dicarbamoyl-2-((Z)-2-tritylthioethen-1-yl)thiazole

In the same manner as in steps b) and c) in Example 3, 102 mg of the title compound was prepared from 200 mg of 4,5-diethoxycarbonyl-2-((Z)-2-tritylthioethen-1-yl)thiazole and 3 ml of a 0.5 M ammonia/dioxane solution.

NMR (DMSO-d$_6$) δ: 6.58 (1H, d, J=11.1 Hz), 6.80 (1H, d, J=11.1 Hz), 7.2-7.4 (15H, m), 8.04 (1H, br s), 8.11 (1H, br s), 8.34 (1H, br s), 10.47 (1H, br s)

Example 36

4-((Z)-2-Tritylthioethen-1-yl)thiazole a) 4-Ethynylthiazole

Bromomethyltriphenylphosphonium bromide (9.83 g) was added to 100 ml of a suspension of 7.27 g of potassium-t-butoxide in THF under ice cooling, the suspension was stirred at the same temperature for 10 min, and 2.44 g of 4-formylthiazole was further added thereto. The mixture was stirred at room temperature for 2 hr. Thereafter, 100 ml of ethyl acetate and 100 ml of semi-saturated brine were added thereto, followed by separation. The organic layer was then washed with semi-saturated brine. The organic layer was dried over anhydrous magnesium sulfate, the solvent was removed by distillation under the reduced pressure, and the residue was purified by column chromatography on silica gel (dichloromethane:hexane=3:2) to give 614 mg of 4-ethynylthiazole.

NMR (CDCl$_3$) δ: 3.15 (1H, s), 7.58 (1H, d, J=2.0 Hz), 8.78 (1H, d, J=2.0 Hz)

b) 4-((Z)-2-Tritylthioethen-1-yl)thiazole

In the same manner as in step e) in Example 1, 1.22 g of the title compound was prepared from 561 mg of 4-ethynylthiazole.

NMR (CDCl$_3$) δ: 6.10 (1H, d, J=11.2 Hz), 6.54 (1H, d, J=11.2 Hz), 7.09-7.34 (15H, m), 7.47 (1H, s), 8.80 (1H, s)

Example 37

2-Carbamoyl-4-((Z)-2-tritylthioethen-1-yl)thiazole a) 4-Bromo-2-carbamoylthiazole Oxalyl dichloride (1.61 ml) was added to 100 ml of a mixed solution composed of 4-bromo-2-carboxythiazole and THF-dichloromethane (2:1), and the mixture was stirred at 60° C. for 2 hr. Under ice cooling, 15 ml of 30% aqueous ammonia was added to the reaction solution, and the mixture was stirred at the same temperature for 30 min. Ethyl acetate (50 ml) and 50 ml of semi-saturated brine were added thereto, followed by separation. The organic layer was then dried over anhydrous magnesium sulfate, the solvent was removed by distillation under the reduced pressure, and the residue was purified by column chromatography on silica gel (chloroform:methanol=40:1) to give 1.36 g of 4-bromo-2-carbamoylthiazole.

NMR (DMSO-d$_6$) δ: 7.98 (1H, br s), 8.16 (1H, s), 8.33 (1H, br s)

b) 2-Carbamoyl-4-ethynylthiazole

In the same manner as in step b) in Example 4, 694 mg of 2-carbamoyl-4-ethynylthiazole was prepared from 1.22 g of 4-bromo-2-carbamoylthiazole.

NMR (DMSO-d$_6$) δ: 7.98 (1H, br s), 8.16 (1H, s), 8.33 (1H, br s)

c) 2-Carbamoyl-4-((Z)-2-tritylthioethen-1-yl)thiazole

In the same manner as in step e) in Example 1, 1.38 g of the title compound was prepared from 597 mg of 2-carbamoyl-4-ethynylthiazole.

NMR (CDCl$_3$) δ: 5.55 (1H, br s), 6.16 (1H, d, J=11.0 Hz), 6.43 (1H, d, J=11.0 Hz), 7.25-7.36 (15H, m), 7.61 (1H, s)

Example 38

5-Hydroxymethyl-4-((Z)-2-tritylthioethen-1-yl)thiazole a) 4-Ethoxycarbonyl-5-hydroxymethylthiazole 4,5-Diethoxycarbonylthiazole (7.13 g) was dissolved in 100 ml of ethanol, 2.20 g of sodium borohydride was added to the solution in an argon atmosphere under ice cooling, and the mixture was stirred at room temperature for 12 hr. Water was added to the reaction solution, the mixture was adjusted to pH 4.5 by the addition of 1 N aqueous hydrochloric acid, and the organic solvent was removed by distillation under the reduced pressure. The remaining aqueous solution was extracted five times with chloroform, was dried over anhydrous magnesium sulfate, was filtered, and was concentrated under the reduced pressure. Ethyl acetate and hexane were added to the concentrate, and the resultant solid was collected by filtration to give 2.29 g of 4-ethoxycarbonyl-5-hydroxymethylthiazole.

NMR (CDCl$_3$) δ: 1.45 (3H, t, J=7.2 Hz), 3.65 (1H, t, br t), 4.47 (2H, q, J=7.2 Hz), 5.09 (2H, d, J=5.1 Hz), 8.69 (1H, s)

b) 5-t-Butyldimethylsilyloxymethyl-4-ethoxycarbonylthiazole

4-Ethoxycarbonyl-5-hydroxymethylthiazole (282 mg) was dissolved in 5 ml of DMF, 123 mg of imidazole and 250 mg of t-butyldimethylsilyl chloride were added to the solution in an argon atmosphere under ice cooling, and the mixture was stirred at room temperature for 1.5 hr. Brine was added to the reaction solution, and the mixture was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane:ethyl acetate=3:1) to give 374 mg of 5-t-butyldimethylsilyloxymethyl-4-ethoxycarbonylthiazole.

NMR (CDCl$_3$) δ: 0.14 (6H, s), 0.95 (9H, s), 1.43 (3H, t, J=7.2 Hz), 4.42 (2H, q, J=7.2 Hz), 5.23 (2H, s), 8.66 (1H, s)

c) 5-t-Butyldimethylsilyloxymethyl-4-formylthiazole

A 1.0 M diisobutylaluminum hydride/toluene solution (2.4 ml) was added dropwise to a solution of 578 mg of 5-t-butyldimethylsilyloxymethyl-4-ethoxycarbonylthiazole in 10 ml of toluene under an argon atmosphere at −60° C. The mixture was stirred at the same temperature for 2 hr, water and ethyl acetate were added thereto and the mixture was adjusted to pH 5.5 by the addition of 1 N aqueous hydrochloric acid. The insolubles were removed by filtration through Celite, and the filtrate was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane:ethyl acetate=5:1 to ethyl acetate only) to give 308 mg of 5-t-butyldimethylsilyloxymethyl-4-formylthiazole.

NMR (CDCl$_3$) δ: 0.14 (6H, s), 0.95 (9H, s), 5.24 (2H, s), 8.70 (1H, s), 10.17 (1H, s)

d) 5-t-Butyldimethylsilyloxymethyl-4-ethynylthiazole

In the same manner as in step a) in Example 36, 47 mg of 5-t-butyldimethylsilyloxymethyl-4-ethynylthiazole was prepared from 104 mg of 5-t-butyldimethylsilyloxymethyl-4-formylthiazole.

NMR (CDCl$_3$) δ: 0.12 (6H, s), 0.92 (9H, s), 3.31 (1H, s), 4.98 (2H, s), 8.65 (1H, s)

e) 5-t-Butyldimethylsilyloxymethyl-4-((Z)-2-tritylthioethen-1-yl)thiazole

In the same manner as in step e) in Example 1, 392 mg of 5-t-butyldimethylsilyloxymethyl-4-((Z)-2-tritylthioethen-1-yl)thiazole was prepared from 165 mg of 5-t-butyldimethylsilyloxymethyl-4-ethynylthiazole.

NMR (CDCl₃) δ: 0.06 (6H, s), 0.89 (9H, s), 4.84 (2H, s), 6.07 (1H, d, J=11.1 Hz), 6.17 (1H, d, J=11.1 Hz), 7.2-7.4 (15H, m), 8.76 (1H, m)

f) 5-Hydroxymethyl-4-((Z)-2-tritylthioethen-1-yl)thiazole 5-t-Butyldimethylsilyloxymethyl-4-((Z)-2-tritylthioethen-1-yl)thiazole (392 mg) was dissolved in 10 ml of THF, 0.7 ml of 5 N-aqueous hydrochloric acid was added to the solution, and the mixture was stirred at room temperature for 2 hr. Brine was added to the reaction solution, and the mixture was adjusted to pH 8 by the addition of sodium bicarbonate water. The mixture was extracted twice with ethyl acetate, followed by washing with brine. The organic layer was dried over anhydrous magnesium sulfate, was filtered, and was concentrated under the reduced pressure. Ethyl acetate (5 ml) and 5 ml of hexane were added to the residue, and the resultant solid was collected by filtration to give 180 mg of the title compound.

NMR (DMSO-d₆) δ: 4.65 (2H, d, J=5.4 Hz), 5.57 (1H, t, J=5.4 Hz), 5.91 (1H, d, J=10.8 Hz), 6.39 (1H, d, J=10.8 Hz), 7.2-7.4 (15H, m), 9.05 (1H, s)

Example 39

4-Ethoxycarbonyl-5-(2-trimethylsilylethynyl)thiazole a) 2-Amino-5-bromo-4-ethoxycarbonylthiazole In the same manner as in step a) in Example 1, 46.27 g of 2-amino-5-bromo-4-ethoxycarbonylthiazole was prepared from 43.05 g of 2-amino-4-ethoxycarbonylthiazole and 48.95 g of N-bromosuccinimide.

NMR (CDCl₃) δ: 1.39 (3H, t, J=7.1 Hz), 4.36 (2H, q, J=7.1 Hz), 6.05 (H, br s)

b) 5-Bromo-4-ethoxycarbonylthiazole

In the same manner as in step b) in Example 1, 31.31 g of 5-bromo-4-ethoxycarbonylthiazole was prepared from 48.65 g of 2-amino-5-bromo-4-ethoxycarbonylthiazole.

NMR (CDCl₃) δ: 1.44 (3H, t, J=7.1 Hz), 4.46 (2H, q, J=7.1 Hz), 8.79 (1H, s)

c) 4-Ethoxycarbonyl-5-(2-trimethylsilylethynyl)thiazole

5-Bromo-4-ethoxycarbonylthiazole (18.64 g) was dissolved in 80 ml of DMF. Triethylamine (22 ml), 16.7 ml of ethynyltrimethylsilane, 960 mg of copper(I) iodide, and 1.11 g of bis(triphenylphosphine)palladium(II) dichloride were added in that order to the solution, and the mixture was stirred at 90° C. under an argon atmosphere for one hr. Water (80 ml), 160 ml of ethyl acetate and 160 ml of hexane were added to the reaction solution, and the mixture was washed with (brine+aqueous hydrochloric acid), sodium bicarbonate water, and brine in that order. Activated carbon and anhydrous magnesium sulfate were added to the organic layer, and the mixture was filtered and was concentrated under the reduced pressure to give 16.45 g of the title compound.

NMR (CDCl₃) δ: 0.29 (9H, s), 1.44 (3H, t, J=7.2 Hz), 4.45 (2H, q, J=7.2 Hz), 8.65 (1H, s)

Example 40

4-Ethoxycarbonyl-5-ethynylthiazole

4-Ethoxycarbonyl-5-iodothiazole (1.45 g) was dissolved in 25 ml of N-methyl-2-pyrrolidinone. Tri-n-butylethynyltin (1.78 ml), 143 mg of tri(2-furyl)phosphine, 143 mg of tris(dibenzylideneacetone)dipalladium(0), and 1.43 g of zinc chloride were added to the solution under an argon atmosphere, and the mixture was stirred at room temperature for 40 min. Brine and ethyl acetate were added to the reaction solution. The insolubles were removed by filtration through Celite, and the filtrate was extracted twice with ethyl acetate. The organic layers were combined, were washed with brine, were dried over anhydrous magnesium sulfate, were filtered, and were concentrated under the reduced pressure. The residue was purified by column chromatography on silica gel (hexane:ethyl acetate=3:1) to give 750 mg of the title compound.

NMR (CDCl₃) δ: 1.44 (3H, t, J=7.2 Hz), 3.86 (1H, s), 4.47 (2H, q, J=7.2 Hz), 8.70 (1H, s)

Example 41

Sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) Silver salt of 4-hydroxymethyl-5-((Z)-2-mercaptoethen-1-yl)thiazole Pyridine (0.511 ml) and 6.6 ml of a 1 N aqueous silver nitrate solution was added to 50 ml of a solution of 2.5 g of 4-hydroxymethyl-5-((Z)-2-tritylthioethen-1-yl)thiazole, prepared in Example 1, in THF, and the mixture was stirred at room temperature for 30 min. The precipitated solid was collected by filtration and was washed with 50 ml of acetone, 150 ml of 50% acetone-water, and 100 ml of acetone in that order to give 2.15 g of a crude crystal (purity 780%) of a silver salt of 4-hydroxymethyl-5-[(Z)-2-mercaptoethen-1-yl]thiazole.

b) 4-Nitrobenzyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate The crude crystal of the silver salt of 4-hydroxymethyl-5-[(Z)-2-mercaptoethen-1-yl]thiazole (283 mg) was added to 10 ml of a solution of 599 mg of 4-nitrobenzyl (1R,5R,6S)-2-(diphenylphosphoryloxy)-6-((1R)-1-hydroxyethyl)-1-methyl-1-carbapen-2-em-3-carboxylate in dry acetone under an argon atmosphere at 4° C., and 303 mg of sodium iodide was added thereto. The mixture was stirred at the same temperature for 18 hr. Ethyl acetate (20 ml) and 20 ml of semi-saturated brine were added thereto, and the mixture was filtered through Celite and was washed with ethyl acetate. The filtrate was separated, the organic layer was washed with semi-saturated brine, was dried over anhydrous magnesium sulfate, and was filtered, and ethyl acetate was removed by distillation under the reduced pressure. The residue was purified by column chromatography on silica gel (chloroform:methanol=20:1) to give 298 mg of 4-nitrobenzyl (1R,5S,6S)-6-((1R)-1-hydroxyethyl)-2-[[(Z)-2-(4- hydroxymethylthiazol-5-yl)ethen-1-yl]thio]-1-methyl-1-carbapen-2-em-3-carboxylate.

NMR (DMSO-$d_6$) δ: 1.09 (3H, d, J=7.3 Hz), 1.15 (3H, d, J=6.3 Hz), 3.36 (1H, dd, $J_1$=6.1 Hz, $J_2$=2.9 Hz), 3.83 (1H, m), 4.00 (1H, m), 4.26 (1H, dd, $J_1$=10.0 Hz, $J_2$=3.0 Hz), 4.67 (2H, d, J=4.6 Hz), 5.12 (1H, d, J=5.4 Hz), 5.29-5.38 (2H, m), 5.51 (1H, d, J=13.8 Hz), 6.86 (1H, d, J=10.5 Hz), 7.33 (1H, d, J=10.5 Hz), 7.75 (2H, d, J=8.7 Hz), 8.25 (2H, d, J=8.7 Hz), 9.04 (1H, s)

c) Sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate 10% Pd—C (hydrous, water content 53%) (1.42 g) was added to a solution of 40 ml of a 1/15 M sodium phosphate buffer solution (pH 6.8) of 957 mg of 4-nitrobenzyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate in 40 ml of THF, and the mixture was stirred under a hydrogen atmosphere for 1.5 hr. The 10% Pd—C was removed by filtration and was washed with water. The filtrate was adjusted to pH 6.6 by the addition of saturated sodium bicarbonate water, followed by washing with 40 ml of ethyl acetate. The aqueous layer was concentrated to about 5 ml, and the concentrate was purified by column chromatography (2% methanol-water) on Cosmosil 40C18-PREP to give 360 mg of the title compound.

NMR (DMSO-$d_6$) δ: 0.98 (3H, d, J=7.3 Hz), 1.15 (3H, d, J=6.4 Hz), 3.08 (1H, dd, $J_1$=6.8 Hz, $J_2$=2.7 Hz), 3.38-3.51 (1H, m), 3.84-3.96 (1H, m), 4.02 (1H, dd, $J_1$=9.7 Hz, $J_2$=2.7 Hz), 4.64 (2H, d, J=5.6 Hz), 5.00 (1H, d, J=5.1 Hz), 5.24 (1H, t, J=5.6 Hz), 6.80 (1H, d, J=10.7 Hz), 7.04 (1H, d, J=10.7 Hz), 8.99 (1H, s)

Example 42

Sodium (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate a) Silver salt of 4-(2-hydroxyethoxy)methyl-5-((Z)-2-mercaptoethen-1-yl)thiazole In the same manner as in step a) in Example 41, 3.97 g of a silver salt of 4-(2-hydroxyethoxy)methyl-5-((Z)-2-mercaptoethen-1-yl)thiazole (purity 85%) was prepared from 4.83 g of 4-(2-hydroxyethoxy)methyl-5-((Z)-2-tritylthioethen-1-yl)thiazole prepared in Example 2.

b) 4-Nitrobenzyl (1R,5S,6S)-2-[[(Z)-2-[4-(2-hydroxyethoxy)methylthiazol-5-yl]ethen-1-yl]thio]-1-methyl-6-((1R)-1-triethylsilyloxy ethyl)-1-carbapen-2-em-3-carboxylate A crude crystal (3.97 g) of the silver salt of 4-(2-hydroxyethoxy)methyl-5-((Z)-2-mercaptoethen-1-yl)thiazole was added to 60 ml of a solution of 6.20 g of 4-nitrobenzyl (1R,5R,6S)-2-(diphenylphosphoryloxy)-1-methyl-6-((1R)-1-triethylsilyl-oxyethyl)-1-carbapen-2-em-3-carboxylate in dry acetonitrile under an argon atmosphere at room temperature, and 3.30 g of sodium iodide was then added thereto. The mixture was stirred at the same temperature for 18 hr. Thereafter, 200 ml of ethyl acetate and 200 ml of semi-saturated brine were added thereto, and the mixture was filtered through Celite and was washed with ethyl acetate. The filtrate was subjected to separation, and the organic layer was then washed with semi-saturated brine. The washed organic layer was dried over anhydrous magnesium sulfate and was filtered, and ethyl acetate was removed by distillation under the reduced pressure. The residue was purified by column chromatography on silica gel (chloroform:methanol=20:1) to give 4.17 g of 4-nitrobenzyl (1R,5S,6S)-2-[[(Z)-2-[4-(2-hydroxyethoxy)methylthiazol-5-yl]ethen-1-yl]thio]-1-methyl-6-((1R)-1-triethylsilyloxy ethyl)-1-carbapen-2-em-3-carboxylate.

NMR (CDCl$_3$) δ: 0.61 (6H, q, J=7.5 Hz), 0.95 (9H, t, J=7.5 Hz), 1.20 (3H, d, J=7.5 Hz), 1.27 (3H, d, J=6.3 Hz), 3.29 (1H, dd, $J_1$=5.7 Hz, $J_2$=2.7 Hz), 3.45-3.6 (1H, m), 3.65-3.7 (2H, m), 3.7-3.8 (2H, m), 4.2-4.35 (2H, m), 4.81 (2H, s), 5.29 (1H, d, J=13.8 Hz), 5.50 (1H, d, J=13.8 Hz), 6.54 (1H, d, J=10.2 Hz), 7.17 (1H, d, J=10.2 Hz), 7.67 (2H, d, J=8.7 Hz), 8.22 (2H, d, J=8.7 Hz), 8.77 (1H, s)

c) Sodium (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate 4-Nitrobenzyl (1R,5S,6S)-2-[[(Z)-2-[4-(2-hydroxyethoxy)methylthiazol-5-yl]ethen-1-yl]thio]-1-methyl-6-((1R)-1-triethylsilyloxy ethyl)-1-carbapen-2-em-3-carboxylate (3.82 g) was dissolved in 170 ml of THF and 70 ml of water. 1 N aqueous hydrochloric acid (2.8 ml) was added to the solution, and the mixture was stirred at room temperature for 50 min. The reaction solution was adjusted to pH 3.0 by the addition of saturated sodium bicarbonate water. A 1/15 M sodium phosphate buffer solution (pH 6.8) (170 ml) and 3.10 g of 10% Pd—C (hydrous, water content 53%) were added thereto, and the mixture was stirred under a hydrogen atmosphere for 1.5 hr. 10% Pd—C was removed by filtration and was washed with water, and the filtrate was adjusted to pH 7.0 by the addition of saturated sodium bicarbonate water, followed by washing with 300 ml of ethyl acetate. The aqueous layer was concentrated to about 20 ml, and the residue was purified by column chromatography on Cosmosil 40C18-PREP (5% methanol-water) to give 1.91 g of the title compound.

NMR (DMSO-$d_6$) δ: 0.99 (3H, d, J=7.2 Hz), 1.15 (3H, d, J=6.3 Hz), 3.11 (1H, dd, $J_1$=6.6 Hz, $J_2$=2.4 Hz), 3.4-3.6 (5H, m), 3.8-4.0 (1H, m), 4.05 (1H, dd, $J_1$=9.6 Hz, $J_2$=2.4 Hz), 4.6-4.7 (3H, m), 5.0-5.1 (1H, m), 6.84 (1H, d, J=10.8 Hz), 7.01 (1H, d, J=10.8 Hz), 9.02 (1H, s)

Example 43

Sodium (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate a) Silver salt of 4-N,N-dimethylcarbamoyl-5-((Z)-2-mercaptoethen-1-yl)thiazole In the same manner as in step a) in Example 41, 5.73 g of a crude crystal (purity 80%) of a silver salt of 4-N,N-carbamoyl-5-((Z)-2-mercaptoethen-1-yl)thiazole was prepared from 6.54 g of 4-N,N-dimethylcarbamoyl-5-((Z)-2-tritylthioethen-1-yl)thiazole prepared in Example 3.

b) 4-Nitrobenzyl (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate 5.73 g of the crude crystal of the silver salt of 4-N,N-dimethylcarbamoyl-5-((Z)-2-mercaptoethen-1-yl)thiazole was added to a solution of 8.51 g of 4-nitrobenzyl (1R,5R,6S)-2-(diphenylphosphoryloxy)-6-((1R)-1-hydroxyethyl)-1-methyl-1-carbapen-2-em-3-carboxylate in 100 ml of dry acetonitrile under an argon atmosphere at room temperature, and 4.29 g of sodium iodide was then added thereto. The mixture was stirred at the same temperature for 13 hr. Ethyl acetate (300 ml) and 200 ml of semi-saturated brine were added thereto, and the mixture was filtered through Celite and was washed with ethyl acetate. The filtrate was subjected to separation, and the organic layer was then washed with semi-saturated brine, was dried over anhydrous magnesium sulfate, and was filtered, and ethyl acetate was removed by distillation under the reduced pressure. The residue was purified by column chromatography on silica gel (chloroform:methanol=30:1 to 20:1) to give 4.60 g of 4-nitrobenzyl (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate.

NMR (CDCl$_3$) δ: 1.21 (3H, d, J=7.3 Hz), 1.37 (3H, d, J=6.3 Hz), 3.03 (3H, s), 3.14 (3H, s), 3.33 (1H, dd, J$_1$=6.7 Hz, J$_2$=2.8 Hz), 3.53-3.63 (1H, m), 4.23-4.33 (2H, m), 5.29 (1H, d, J=13.9 Hz), 5.55 (1H, d, J=13.9 Hz), 6.56 (1H, d, J=10.5 Hz), 7.40 (1H, d, J=10.5 Hz), 7.69 (2H, d, J=8.8 Hz), 8.24 (2H, d, J=8.8 Hz), 8.75 (1H, s)

c) Sodium (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate In the same manner as in step c) in Example 41, 2.25 g of the title compound was prepared from 4.60 g of 4-nitrobenzyl (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate.

NMR (D$_2$O) δ (HOD=4.80 ppm): 1.14 (3H, d, J=7.2 Hz), 1.29 (3H, d, J=6.3 Hz), 2.97 (3H, s), 3.15 (3H, s), 3.47 (1H, dd, J$_1$=6.2 Hz, J$_2$=2.6 Hz), 3.57-3.67 (1H, m), 4.21-4.29 (2H, m), 6.94 (1H, d, J=10.5 Hz), 6.97 (1H, d, J=10.5 Hz), 9.04 (1H, s)

Example 44

Sodium (1R,5S,6S)-6-((1R)-1-hydroxyethyl)-2-[[(Z)-2-(4-hydroxymethylthiazol-2-yl)ethen-1-yl]thio]-1-methyl-1-carbapen-2-em-3-carboxylate In the same manner as in Example 42, 90.7 mg of the title compound was prepared from 370 mg of 4-hydroxymethyl-2-((Z)-2-tritylthioethen-1-yl)thiazole prepared in Example 4.

NMR (D$_2$O) δ (HOD=4.80 ppm): 1.15 (3H, d, J=6.9 Hz), 1.28 (3H, d, J=6.3 Hz), 3.4-3.5 (1H, m), 3.6-3.7 (1H, m), 4.2-4.3 (2H, m), 4.71 (2H, s), 7.00 (1H, d, J=10.8 Hz), 7.14 (1H, d, J=10.8 Hz), 7.52 (1H, s)

Example 45

Sodium (1R,5S,6S)-6-((1R)-1-hydroxyethyl)-1-methyl-2-[[(Z)-2-(4-methylthiazol-5-yl)ethen-1-yl]thio]-1-carbapen-2-em-3-carboxylate In the same manner as in Example 43, 240 mg of the title compound was prepared from 1.95 g of 4-methyl-5-((Z)-2-tritylthioethen-1-yl)thiazole prepared in Example 5.

NMR (D$_2$O) δ (HOD=4.80 ppm): 1.11 (3H, d, J=7.4 Hz), 1.25 (3H, d, J=6.6 Hz), 2.45 (3H, s), 3.41 (1H, dd, J$_1$=6.2 Hz, J$_2$=2.6 Hz), 3.51-3.60 (1H, m), 4.15-4.28 (2H, m), 6.65 (1H, d, J=10.5 Hz), 7.05 (1H, d, J=10.5 Hz), 8.88 (1H, s)

Example 46

Sodium (1R,5S,6S)-2-[[(Z)-2-(4-carbamoylthiazol-5-yl)ethen-1-yl]thio]-6-((1R)-1-hydroxyethyl)-1-methyl-1-carbapen-2-em-3-carboxylate In the same manner as in Example 42, 287 mg of the title compound was prepared from 2.03 g of 4-carbamoyl-5-((Z)-2-tritylthioethen-1-yl)thiazole prepared in Example 6.

NMR (D$_2$O) δ (HOD=4.80 ppm): 1.15 (3H, d, J=7.3 Hz), 1.30 (3H, d, J=6.3 Hz), 3.47 (1H, dd, J$_1$=6.1 Hz, J$_2$=2.7 Hz), 3.60-3.71 (1H, m), 4.21-4.30 (2H, m), 6.97 (1H, d, J=10.7 Hz), 7.78 (1H, d, J=10.7 Hz), 8.95 (1H, s)

Example 47

Sodium (1R,5S,6S)-6-((1R)-1-hydroxyethyl)-1-methyl-2-[[(Z)-2-(4-N-methylcarbamoylthiazol-5-yl)ethen-1-yl]thio]-1-carbapen-2-em-3-carboxylate In the same manner as in Example 42, 86 mg of the title compound was prepared from 394 mg of 4-N-methylcarbamoyl-5-((Z)-2-tritylthioethen-1-yl)thiazole prepared in Example 7.

NMR (D$_2$O) δ (HOD=4.65 ppm): 1.00 (3H, d, J=7.1 Hz), 1.15 (3H, d, J=6.3 Hz), 2.80 (3H, s), 3.32 (1H, d, J=3.7 Hz), 3.48-3.52 (1H, m), 4.07-4.12 (2H, m), 6.80 (1H, d, J=10.7 Hz), 7.61 (1H, d, J=10.7 Hz), 8.79 (1H, s)

Example 48

Sodium (1R,5S,6S)-2-[[(Z)-2-(4-N-cyanomethyl-N-methylcarbamoylthiazol-5-yl)ethen-1-yl]thio]-6-((1R)-1-hydroxyethyl)-1-methyl-1-carbapen-2-em-3-carboxylate In the same manner as in Example 43, 487 mg of the title compound was prepared from 1.24 g of 4-N-cyanomethyl-N-methylcarbamoyl-5-((Z)-2-tritylthioethen-1-yl)thiazole prepared in Example 8.

NMR (D$_2$O) δ (HOD=4.65 ppm): 1.00 (3H, d, J=7.3 Hz), 1.15 (3H, d, J=6.3 Hz), 2.98, 3.10 (total 3H, both s), 3.33 (1H, dd, J$_1$=6.1 Hz, J$_2$=2.7 Hz), 3.43-3.53 (1H, m), 4.07-4.15 (2H, m), 4.32, 4.47 (total 2H, both s), 6.75-6.96 (2H, m), 8.91-8.93 (1H, m)

Example 49

Sodium (1R,5S,6S)-2-[[(Z)-2-(4-N-cyanomethylcarbamoylthiazol-5-yl)ethen-1-yl]thio]-6-((1R)-1-hydroxyethyl)-1-methyl-1-carbapen-2-em-3-carboxylate In the same manner as in Example 43, 487 mg of the title compound was prepared from 1.24 g of 4-N-cyanomethyl-carbamoyl-5-((Z)-2-tritylthioethen-1-yl)thiazole prepared in Example 9.

NMR (D$_2$O) δ (HOD=4.65 ppm): 1.00 (3H, d, J=7.3 Hz), 1.16 (3H, d, J=6.4 Hz), 3.33 (1H, dd, J$_1$=6.1 Hz, J$_2$=2.7 Hz), 3.46-3.56 (1H, m), 4.07-4.15 (2H, m), 4.26 (2H, s), 6.87 (1H, d, J=10.7 Hz), 7.67 (1H, d, J=10.7 Hz), 8.79 (1H, s)

Example 50

Sodium (1R,5S,6S)-2-[[(Z)-2-[4-N-(2-cyanoethyl)carbamoylthiazol-5-yl]ethen-1-yl]thio]-6-((1R)-1-hydroxyethyl)-1-methyl-1-carbapen-2-em-3-carboxylate In the same manner as in Example 43, 183 mg of the title compound was prepared from 415 mg of 4-N-(2-cyanoethyl)carbamoyl-5-((Z)-2-tritylthioethen-1-yl)thiazole prepared in Example 10.

NMR (D$_2$O) δ (HOD=4.80 ppm): 1.15 (3H, d, J=7.5 Hz), 1.31 (3H, d, J=6.3 Hz), 2.8-2.9 (2H, m), 3.48 (1H, dd, J$_1$=6.0 Hz, J$_2$=2.4 Hz), 3.6-3.8 (3H, m), 4.2-4.3 (2H, m), 6.98 (1H, d, J=10.5 Hz), 7.77 (1H, d, J=10.5 Hz), 8.95 (1H, s)

Example 51

Sodium (1R,5S,6S)-2-[[(Z)-2-(4-cyanomethylthiazol-5-yl)ethen-1-yl]thio]-6-((1R)-1-hydroxyethyl)-1-methyl-1-carbapen-2-em-3-carboxylate In the same manner as in Example 43, 117 mg of the title compound was prepared from 305 mg of 4-cyanomethyl-5-((Z)-2-tritylthioethen-1-yl)thiazole prepared in Example 11.

NMR (D$_2$O) δ (HOD=4.80 ppm): 1.15 (3H, d, J=6.9 Hz), 1.32 (3H, d, J=6.3 Hz), 3.48 (1H, dd, J$_1$=6.3 Hz, J$_2$=3.0 Hz), 3.55-3.7 (1H, m), 4.16 (2H, s), 4.2-4.3 (2H, m), 6.85 (1H, d, J=10.5 Hz), 6.98 (1H, d, J=10.5 Hz), 9.00 (1H, s)

Example 52

Sodium (1R,5S,6S)-6-((1R)-1-hydroxyethyl)-2-[[(Z)-2-[4-(2-methoxyethoxy)methylthiazol-5-yl]ethen-1-yl]thio]-1-methyl-1-carbapen-2-em-3-carboxylate In the same manner as in Example 43, 159 mg of the title compound was prepared from 434 mg of 4-(2-methoxyethoxy)methyl-5-((Z)-2-tritylthioethen-1-yl)thiazole prepared in Example 12.

NMR (D$_2$O) δ (HOD=4.80 ppm): 1.16 (3H, d, J=7.2 Hz), 1.32 (3H, d, J=6.3 Hz), 3.38 (3H, s), 3.45-3.5 (1H, m), 3.6-3.7 (2H, m), 3.7-3.8 (2H, m), 4.2-4.3 (2H, m), 6.82 (1H, d, J=10.5 Hz), 7.18 (1H, d, J=10.5 Hz), 8.99 (1H, s)

Example 53

Sodium (1R,5S,6S)-2-[[(Z)-2-[4-(3-cyanoazetidin-1-yl)carbonylthiazol-5-yl]ethen-1-yl]thio]-6-((1R)-1-hydroxyethyl)-1-methyl-1-carbapen-2-em-3-carboxylate In the same manner as in Example 43, 63 mg of the title compound was prepared from 694 mg of 4-(3-cyanoazetidin-1-yl)carbonyl-5-((Z)-2-tritylthioethen-1-yl)thiazole prepared in Example 13.

NMR (D$_2$O) δ (HOD=4.65 ppm): 1.00 (3H, d, J=7.1 Hz), 1.15 (3H, d, J=6.4 Hz), 3.32-3.34 (1H, m), 3.46-3.54 (1H, m), 3.64-3.72 (1H, m), 4.07-4.14 (2H, m), 4.30-4.44 (2H, m), 4.48-4.58 (2H, m), 6.84 (1H, d, J=10.5 Hz), 7.31 (1H, d, J=10.5 Hz), 8.84 (1H, s)

Example 54

Sodium (1R,5S,6S)-6-((1R)-1-hydroxyethyl)-2-[[(Z)-2-[4-N-(2-hydroxyethyl)carbamoylthiazol-5-yl]ethen-1-yl]thio]-1-methyl-1-carbapen-2-em-3-carboxylate In the same manner as in Example 42, 289 mg of the title compound was prepared from 870 mg of 4-N-(2-hydroxyethyl)carbamoyl-5-((Z)-2-tritylthioethen-1-yl)thiazole prepared in Example 14.

NMR (D$_2$O) δ (HOD=4.65 ppm): 1.04 (3H, d, J=7.2 Hz), 1.19 (3H, d, J=6.3 Hz), 3.34-3.38 (1H, m), 3.43-3.47 (2H, m), 3.50-3.56 (1H, m), 3.65-3.70 (2H, m), 4.10-4.15 (2H, m), 6.85 (1H, d, J=10.5 Hz), 7.65 (1H, d, J=10.5 Hz), 8.83 (1H, s)

Example 55

Sodium (1R,5S,6S)-6-((1R)-1-hydroxyethyl)-2-[[(Z)-2-[4-N-(3-hydroxypropan-1-yl)carbamoylthiazol-5-yl]ethen-1-yl]thio]-1-methyl-1-carbapen-2-em-3-carboxylate In the same manner as in Example 42, 284 mg of the title compound was prepared from 643 mg of 4-N-(3-hydroxypropan-1-yl)carbamoyl-2-((Z)-2-tritylthio ethen-1-yl)thiazole prepared in Example 15.

NMR (D$_2$O) δ (HOD=4.80 ppm): 1.15 (3H, d, J=7.2 Hz), 1.32 (3H, d, J=6.6 Hz), 1.8-2.0 (2H, m), 3.4-3.55 (3H, m), 3.6-3.8 (3H, m), 3.7-3.8 (2H, m), 4.2-4.35 (2H, m), 6.93 (1H, d, J=10.5 Hz), 7.74 (1H, d, J=10.5 Hz), 8.92 (1H, s)

Example 56

Sodium (1R,5S,6S)-6-((1R)-1-hydroxyethyl)-2-[[(Z)-2-[4-N-(2-hydroxyethyl)-N-methylcarbamoylthiazol-5-yl]ethen-1-yl]thio]-1-methyl-1-carbapen-2-em-3-carboxylate In the same manner as in Example 42, 105 mg of the title compound was prepared from 628 mg of 4-N-(2-hydroxyethyl)-N-methylcarbamoyl-5-((Z)-2-tritylthioethen-1-yl)thiazole prepared in Example 16.

NMR (D$_2$O) δ (HOD=4.65 ppm): 0.99 (3H, d, J=6.8 Hz), 1.15 (3H, d, J=6.1 Hz), 2.85, 3.03 (total 3H, both s), 3.29-3.33 (2H, m), 3.45-3.50 (2H, m), 3.58-3.62 (1H, m), 3.73-3.77 (1H, m), 4.09-4.13 (2H, m), 6.72-6.77 (1H, m), 6.84 (1H, d, J=10.5 Hz), 8.89, 8.91 (total 1H, both s)

Example 57

Sodium (1R,5S,6S)-2-[[(Z)-2-[4-(azetidin-1-yl)carbonylthiazol-5-yl]ethen-1-yl]thio]-6-((1R)-1-hydroxyethyl)-1-methyl-1-carbapen-2-em-3-carboxylate In the same manner as in Example 43, 230 mg of the title compound was prepared from 569 mg of 4-(azetidin-1-yl)carbonyl-5-((Z)-2-tritylthioethen-1-yl)thiazole prepared in Example 17.

NMR (D$_2$O) δ (HOD=4.65 ppm): 0.98 (3H, d, J=7.6 Hz), 1.15 (3H, d, J=6.4 Hz), 2.13-2.27 (2H, m), 3.31 (1H, dd, $J_1$=6.4 Hz, $J_2$=2.7 Hz), 3.42-3.53 (1H, m), 4.00-4.18 (6H, m), 6.77 (1H, d, J=10.8 Hz), 7.14 (1H, d, J=10.8 Hz), 8.82 (1H, s)

Example 58

Sodium (1R,5S,6S)-2-[[(Z)-2-(4-(3-hydroxyazetidin-1-yl)carbonylthiazol-5-yl)ethen-1-yl]thio]-6-((1R)-1-hydroxyethyl)-1-methyl-1-carbapen-2-em-3-carboxylate In the same manner as in Example 42, 0.282 g of the title compound was prepared from 0.742 g of 4-(3-hydroxyazetidin-1-yl)carbonyl-5-((Z)-2-tritylthioethen-1-yl)thiazole prepared in Example 18.
NMR ($D_2O$) δ (HOD=4.65 ppm): 0.98 (3H, d, J=7.4 Hz), 1.14 (3H, d, J=6.4 Hz), 3.31 (1H, dd, $J_1$=6.0 Hz, $J_2$=2.6 Hz), 3.49 (1H, m), 3.88 (1H, m), 4.02 (1H, m), 4.10 (2H, m), 4.34 (2H, m), 4.54 (1H, m), 6.78 (1H, 2d, J=10.6 Hz), 7.17 (1H, 2d, J=10.5 Hz), 8.81 (1H, s)

Example 59

Sodium (1R,5S,6S)-6-((1R)-1-hydroxyethyl)-2-[[(Z)-2-[4-(3-hydroxypropan-1-yloxy)methylthiazol-5-yl]ethen-1-yl]thio]-1-methyl-1-carbapen-2-em-3-carboxylate In the same manner as in Example 42, 210 mg of the title compound was prepared from 903 mg of 4-(3-hydroxypropan-1-yloxy)methyl-5-((Z)-2-tritylthioethen-1-yl)thiazole prepared in Example 19.
NMR ($D_2O$) δ (HOD=4.80 ppm): 1.10 (3H, d, J=7.2 Hz), 1.28 (3H, d, J=6.3 Hz), 1.75-1.85 (2H, m), 3.4-3.5 (1H, m), 3.5-3.7 (5H, m), 4.15-4.3 (2H, m), 4.68 (2H, s), 6.75 (1H, d, J=10.2 Hz), 7.69 (1H, d, J=10.2 Hz), 8.92 (1H, s)

Example 60

Sodium (1R,5S,6S)-2-[[(Z)-2-(2-amino-4-carbamoylthiazol-5-yl)ethen-1-yl]thio]-6-((1R)-1-hydroxyethyl)-1-methyl-1-carbapen-2-em-3-carboxylate In the same manner as in Example 42, 37 mg of the title compound was prepared from 182 mg of 2-amino-4-carbamoyl-5-((Z)-2-tritylthioethen-1-yl)thiazole prepared in Example 20.
NMR ($D_2O$) δ (HOD=4.80 ppm): 1.15 (3H, d, J=7.2 Hz), 1.28 (3H, d, J=6.3 Hz), 3.42 (1H, dd, $J_1$=6.0 Hz, $J_2$=2.7 Hz), 3.45-3.6 (1H, m), 4.15-4.3 (2H, m), 6.51 (1H, d, J=10.5 Hz), 7.67 (1H, d, J=10.5 Hz)

Example 61

Sodium (1R,5S,6S)-6-((1R)-1-hydroxyethyl)-2-[[(E)-2-(4-hydroxymethylthiazol-5-yl)ethen-1-yl]thio]-1-methyl-1-carbapen-2-em-3-carboxylate In the same manner as in Example 43, 36 mg of the title compound was prepared from 330 mg of 4-hydroxymethyl-5-((E)-2-tritylthioethen-1-yl)thiazole prepared in Example 21.
NMR ($D_2O$) δ (HOD=4.65 ppm): 1.01 (3H, d, J=7.1 Hz), 1.14 (3H, d, J=6.0 Hz), 3.27-3.31 (1H, m), 3.40-3.58 (1H, m), 4.05-4.14 (2H, m), 4.60 (2H, s), 6.81 (1H, d, J=15.3 Hz), 7.03 (1H, d, J=15.4 Hz), 8.67 (1H, s)

Example 62

Sodium (1R,5S,6S)-2-[[(Z)-2-(2-carbamoylthiazol-5-yl)ethen-1-yl]thio]-6-((1R)-1-hydroxyethyl)-1-methyl-1-carbapen-2-em-3-carboxylate In the same manner as in Example 42, 158 mg of the title compound was prepared from 2.88 g of 2-carbamoyl-5-((Z)-2-tritylthioethen-1-yl)thiazole prepared in Example 22.
NMR ($D_2O$) δ (HOD=4.80 ppm): 1.14 (3H, d, J=7.3 Hz), 1.30 (3H, d, J=6.6 Hz), 3.48 (1H, dd, $J_1$=6.1 Hz, $J_2$=2.7 Hz), 3.59-3.70 (1H, m), 4.22-4.30 (2H, m), 6.90 (1H, d, J=10.5 Hz), 7.12 (1H, d, J=10.5 Hz), 8.03 (1H, s)

Example 63

Sodium (1R,5S,6S)-2-[[(Z)-2-(2-aminothiazol-5-yl)ethen-1-yl]thio]-6-((1R)-1-hydroxyethyl)-1-methyl-1-carbapen-2-em-3-carboxylate In the same manner as in Example 42, 39 mg of the title compound was prepared from 596 mg of 2-amino-5-((Z)-2-tritylthioethen-1-yl)thiazole prepared in Example 23.
NMR ($D_2O$) δ (HOD=4.80 ppm): 1.13 (3H, d, J=7.3 Hz), 1.29 (3H, d, J=6.3 Hz), 3.45-3.60 (2H, m), 4.14-4.30 (2H, m), 6.25 (1H, d, J=9.5 Hz), 7.03 (1H, d, J=9.5 Hz), 7.22 (1H, s)

Example 64

Sodium (1R,5S,6S)-2-[[(Z)-2-(2-N,N-dimethylcarbamoylthiazol-5-yl)ethen-1-yl]thio]-6-((1R)-1-hydroxyethyl)-1-methyl-1-carbapen-2-em-3-carboxylate In the same manner as in Example 43, 295 mg of the title compound was prepared from 3.15 g of 2-N,N-dimethylcarbamoyl-5-((Z)-2-tritylthioethen-1-yl)thiazole prepared in Example 24.
NMR ($D_2O$) δ (HOD=4.65 ppm): 0.99 (3H, d, J=7.3 Hz), 1.15 (3H, d, J=6.6 Hz), 3.06 (3H, s), 3.20 (3H, s), 3.32 (1H, dd, $J_1$=6.1 Hz, $J_2$=2.6 Hz), 3.43-3.52 (1H, m), 4.06-4.15 (2H, m), 6.72 (1H, d, J=10.5 Hz), 6.96 (1H, d, J=10.5 Hz), 7.85 (1H, s)

Example 65

Sodium (1R,5S,6S)-2-[[(Z)-2-(4-carbamoylthiazol-2-yl)ethen-1-yl]thio]-6-((1R)-1-hydroxyethyl)-1-methyl-1-carbapen-2-em-3-carboxylate In the same manner as in Example 43, 24 mg of the title compound was prepared from 92 mg of 4-carbamoyl-2-((Z)-2-tritylthioethen-1-yl)thiazole prepared in Example 25.
NMR ($D_2O$) δ (HOD=4.65 ppm): 1.19 (3H, d, J=7.3 Hz), 1.31 (3H, d, J=6.3 Hz), 3.50 (1H, dd, $J_1$=6.1 Hz, $J_2$=2.7 Hz), 3.70-3.81 (1H, m), 4.23-4.32 (1H, m), 6.96 (1H, d, J=10.7 Hz), 7.24 (1H, d, J=10.7 Hz), 8.24 (1H, s)

Example 66

Sodium (1R,5S,6S)-6-((1R)-1-hydroxyethyl)-2-[[(Z)-2-[4-N-(2-hydroxyethyl)carbamoylthiazol-2-yl]ethen-1-yl]thio]-1-methyl-1-carbapen-2-em-3-carboxylate In the same manner as in Example 43, 75 mg of the title compound was prepared from 371 mg of 4-N-(2-hydroxyethyl)carbamoyl-2-((Z)-2-tritylthioethen-1-yl)thiazole prepared in Example 26.

NMR (D$_2$O) δ (HOD=4.80 ppm): 1.15 (3H, d, J=7.5 Hz), 1.27 (3H, d, J=6.3 Hz), 3.4-3.6 (3H, m), 3.65-3.8 (3H, m), 4.2-4.3 (2H, m), 6.93 (1H, d, J=11.1 Hz), 7.19 (1H, d, J=11.1 Hz), 8.17 (1H, s)

Example 67

Sodium (1R,5S,6S)-2-[[(Z)-2-(4-N,N-dimethylcarbamoylthiazol-2-yl)ethen-1-yl]thio]-6-((1R)-1-hydroxyethyl)-1-methyl-1-carbapen-2-em-3-carboxylate In the same manner as in Example 43, 273 mg of the title compound was prepared from 854 mg of 4-N,N-dimethylcarbamoyl-2-((Z)-2-tritylthioethen-1-yl)thiazole prepared in Example 27.

NMR (D$_2$O) δ (HOD=4.80 ppm): 1.19 (3H, d, J=6.9 Hz), 1.32 (3H, d, J=6.3 Hz), 3.14 (3H, s), 3.23 (3H, s), 3.5-3.55 (1H, m), 3.7-3.8 (1H, m), 4.2-4.35 (2H, m), 7.00 (1H, d, J=10.5 Hz), 7.24 (1H, d, J=10.5 Hz), 7.98 (1H, s)

Example 68

Sodium (1R,5S,6S)-6-((1R)-1-hydroxyethyl)-1-methyl-2-[[(Z)-2-(4-N-methylcarbamoylthiazol-2-yl)ethen-1-yl]thio]-1-carbapen-2-em-3-carboxylate In the same manner as in Example 43, 130 mg of the title compound was prepared from 745 mg of 4-N-methylcarbamoyl-2-((Z)-2-tritylthioethen-1-yl)thiazole prepared in Example 28.

NMR (D$_2$O) δ (HOD=4.65 ppm): 1.03 (3H, d, J=7.3 Hz), 1.16 (3H, d, J=6.3 Hz), 2.82 (3H, s), 3.34 (1H, dd, J$_1$=6.1 Hz, J$_2$=2.7 Hz), 3.54-3.65 (1H, m), 4.07-4.16 (2H, m), 6.77 (1H, d, J=10.8 Hz), 7.05 (1H, d, J=10.8 Hz), 8.00 (1H, s)

Example 69

Sodium (1R,5S,6S)-2-[[(Z)-2-(4-N-cyanomethylcarbamoylthiazol-2-yl)ethen-1-yl]thio]-6-((1R)-1-hydroxyethyl)-1-methyl-1-carbapen-2-em-3-carboxylate In the same manner as in Example 43, 18 mg of the title compound was prepared from 68 mg of 4-N-cyanomethylcarbamoyl-2-((Z)-2-tritylthioethen-1-yl)thiazole prepared in Example 29.

NMR (D$_2$O) δ (HOD=4.65 ppm): 1.11 (3H, d, J=7.3 Hz), 1.16 (3H, d, J=6.4 Hz), 3.33 (1H, dd, J$_1$=6.0 Hz, J$_2$=2.3 Hz), 3.55-3.63 (1H, m), 4.08-4.13 (2H, m), 4.29 (2H, s), 6.73 (1H, d, J=10.7 Hz), 7.03 (1H, d, J=10.7 Hz), 8.07 (1H, s)

Example 70

Sodium (1R,5S,6S)-2-[[(Z)-2-(4-N-cyanomethyl-N-methylcarbamoylthiazol-2-yl)ethen-1-yl]thio]-6-((1R)-1-hydroxyethyl)-1-methyl-1-carbapen-2-em-3-carboxylate In the same manner as in Example 43, 15 mg of the title compound was prepared from 90 mg of 4-N-cyanomethyl-N-methylcarbamoyl-2-((Z)-2-tritylthioethen-1-yl)thiazole prepared in Example 30.

NMR (D$_2$O) δ (HOD=4.65 ppm): 1.04 (3H, d, J=7.3 Hz), 1.16 (3H, d, J=5.6 Hz), 3.10, 3.30 total (3H, both s), 3.35 (1H, dd, J$_1$=6.0 Hz, J$_2$=2.1 Hz), 3.57-3.63 (1H, m), 4.09-4.16 (2H, m), 4.43, 4.89-5.02 (total 2H, s & m), 6.82 (1H, d, J=10.7 Hz), 7.08 (1H, d, J=10.7 Hz), 7.99, 8.05 (total 1H, both s)

Example 71

Sodium (1R,5S,6S)-2-[[(Z)-2-(4-cyanomethylthiazol-2-yl)ethen-1-yl]thio]-6-((1R)-1-hydroxyethyl)-1-methyl-1-carbapen-2-em-3-carboxylate In the same manner as in Example 43, 739 mg of the title compound was prepared from 1.48 g of 4-cyanomethyl-2-((Z)-2-tritylthioethen-1-yl)thiazole prepared in Example 31.

NMR (D$_2$O) δ (HOD=4.65 ppm): 0.98 (3H, d, J=7.1 Hz), 1.15 (3H, d, J=5.8 Hz), 3.32 (1H, m), 3.54 (1H, m), 3.89 (2H, s), 4.08-4.13 (2H, m), 6.76 (1H, d, J=10.8 Hz), 6.99 (1H, d, J=10.2 Hz), 7.37 (1H, s)

Example 72

Sodium (1R,5S,6S)-2-[[(Z)-2-(4-(3-hydroxyazetidin-1-yl)carbonylthiazol-2-yl)ethen-1-yl]thio]-6-((1R)-1-hydroxyethyl)-1-methyl-1-carbapen-2-em-3-carboxylate In the same manner as in Example 43, 208 mg of the title compound was prepared from 1.28 g of 4-(3-hydroxyazetidin-1-yl)carbonyl-2-((Z)-2-tritylthioethen-1-yl)thiazole prepared in Example 32.

NMR (D$_2$O) δ (HOD=4.65 ppm): 0.98 (3H, d, J=7.3 Hz), 1.14 (3H, d, J=6.6 Hz), 3.30 (1H, dd, J$_1$=5.9 Hz, J$_2$=2.5 Hz), 3.54-3.60 (1H, m), 3.84 (1H, m), 4.07-4.13 (2H, m), 4.27 (1H, m), 4.42-4.49 (1H, m), 4.53-4.63 (1H, m), 4.85-4.92 (1H, m), 6.62 (1H, 2d, J=10.8 Hz), 6.91 (1H, 2d, J=11.0 Hz), 7.87 (1H, 2s).

Example 73

Sodium (1R,5S,6S)-2-[[(Z)-2-(4-(3-cyanoazetidin-1-yl)carbonylthiazol-2-yl)ethen-1-yl]thio]-6-((1R)-1-hydroxyethyl)-1-methyl-1-carbapen-2-em-3-carboxylate In the same manner as in Example 43, 21 mg of the title compound was prepared from 50 mg of 4-(3-cyanoazetidin-1-yl)carbonyl-2-((Z)-2-tritylthioethen-1-yl)thiazole prepared in Example 33.

NMR (D$_2$O) δ (HOD=4.65 ppm): 1.02 (3H, 2d, J=7.1 Hz), 1.15 (3H, d, J=6.3 Hz), 3.33 (1H, dd, J$_1$=5.9 Hz, J$_2$=2.7 Hz), 3.61 (1H, m), 3.73 (1H, m), 4.12 (2H, m), 4.28 (1H, m), 4.37 (1H, m), 4.86 (1H, m), 5.08 (1H, m), 6.73 (1H, 2d, J=10.9 Hz), 7.01 (1H, d, J=11.0 Hz), 7.99 (1H, s)

Example 74

Sodium (1R,5S,6S)-6-((1R)-1-hydroxyethyl)-2-[[(Z)-2-(5-hydroxymethylthiazol-2-yl)ethen-1-yl]thio]-1-methyl-1-carbapen-2-em-3-carboxylate In the same manner as in Example 43, 38 mg of the title compound was prepared from 234 mg of 5-hydroxymethyl-2-((Z)-2-tritylthioethen-1-yl)thiazole prepared in Example 34.

NMR (D$_2$O) δ (HOD=4.80 ppm): 1.13 (3H, d, J=7.2 Hz), 1.29 (3H, d, J=6.3 Hz), 3.4-3.5 (1H, m), 3.6-3.8 (1H, m), 4.2-4.3 (2H, m), 4.84 (2H, s), 6.91 (1H, d, J=10.8 Hz), 7.09 (1H, d, J=10.8 Hz), 7.69 (1H, s)

Example 75

Sodium (1R,5S,6S)-2-[[(Z)-2-(4,5-dicarbamoylthiazol-2-yl)ethen-1-yl]thio]-6-((1R)-1-hydroxyethyl)-1-methyl-1-carbapen-2-em-3-carboxylate In the same manner as in Example 42, 13 mg of the title compound was prepared from 102 mg of 4,5-dicarbamoyl-2-((Z)-2-tritylthioethen-1-yl)thiazole prepared in Example 35.
NMR (D$_2$O) δ (HOD=4.80 ppm): 1.21 (3H, d, J=6.9 Hz), 1.34 (3H, d, J=6.0 Hz), 3.5-3.6 (1H, m), 3.7-3.8 (1H, m), 4.2-4.4 (2H, m), 6.83 (1H, d, J=10.8 Hz), 7.36 (1H, d, J=10.8 Hz)

Example 76

Sodium (1R,5S,6S)-6-((1R)-1-hydroxyethyl)-1-methyl-2-[[(Z)-2-(thiazol-4-yl)ethen-1-yl]thio]-1-carbapen-2-em-3-carboxylate In the same manner as in Example 42, 354 mg of the title compound was prepared from 1.20 g of 4-((Z)-2-tritylthioethen-1-yl)thiazole prepared in Example 36.
NMR (D$_2$O) δ (HOD=4.80 ppm): 1.18 (3H, d, J=7.3 Hz), 1.31 (3H, d, J=6.3 Hz), 3.45-3.50 (1H, m), 3.61-3.77 (1H, m), 4.22-4.31 (2H, m), 6.85 (1H, d, J=10.7 Hz), 6.91 (1H, d, J=10.7 Hz), 7.77 (1H, s), 9.01 (1H, s)

Example 77

Sodium (1R,5S,6S)-2-[[(Z)-2-(2-carbamoylthiazol-4-yl)ethen-1-yl]thio]-6-((1R)-1-hydroxyethyl)-1-methyl-1-carbapen-2-em-3-carboxylate In the same manner as in Example 42, 174 mg of the title compound was prepared from 1.38 g of 2-carbamoyl-4-((Z)-2-tritylthioethen-1-yl)thiazole prepared in Example 37.
NMR (D$_2$O) δ (HOD=4.65 ppm): 1.03 (3H, d, J=7.3 Hz), 1.16 (3H, d, J=6.3 Hz), 3.30-3.35 (1H, m), 3.55-3.62 (1H, m), 4.07-4.15 (2H, m), 6.62 (1H, d, J=11.0 Hz), 6.72 (1H, d, J=11.0 Hz), 7.70 (1H, s)

Example 78

Sodium (1R,5S,6S)-6-((1R)-1-hydroxyethyl)-2-[[(Z)-2-(5-hydroxymethylthiazol-4-yl)ethen-1-yl]thio]-1-methyl-1-carbapen-2-em-3-carboxylate In the same manner as in Example 43, 9 mg of the title compound was prepared from 180 mg of 5-hydroxymethyl-4-((Z)-2-tritylthioethen-1-yl)thiazole prepared in Example 38.
NMR (D$_2$O) δ (HOD=4.80 ppm): 1.16 (3H, d, J=7.2 Hz), 1.29 (3H, d, J=6.3 Hz), 3.45 (1H, dd, J$_1$=6.0 Hz, J$_2$=2.7 Hz), 3.6-3.75 (1H, m), 4.2-4.3 (2H, m), 4.86 (2H, s), 6.74 (1H, d, J=10.5 Hz), 6.83 (1H, d, J=10.5 Hz), 8.97 (1H, s)

Example 79

Sodium (1R,5S,6S)-2-[[(Z)-2-(4-acetoxymethylthiazol-5-yl)ethen-1-yl]thio]-6-((1R)-1-hydroxyethyl)-1-methyl-1-carbapen-2-em-3-carboxylate a) 4-Nitrobenzyl (1R,5S,6S)-2-[[(Z)-2-(4-hydroxymethylthiazol-5-yl)ethen-1-yl]thio]-1-methyl-6-((1R)-1-triethylsilyloxyethyl)-1-carbapen-2-em-3-carboxylate In the same manner as in step b) in Example 42, 582 mg of 4-nitrobenzyl (1R,5S,6S)-2-[[(Z)-2-(4-hydroxymethylthiazol-5-yl)ethen-1-yl]thio]-1-methyl-6-((1R)-1-triethylsilyloxyethyl)-1-carbapen-2-em-3-carboxylate was prepared from 653 mg of the crude crystal of the silver salt of 4-hydroxymethyl-5-((Z)-2-mercaptoethen-1-yl)thiazole prepared in step a) in Example 41.
NMR (CDCl$_3$) δ: 0.55-0.65 (6H, m), 0.9-1.0 (9H, m), 1.20 (3H, d, J=7.2 Hz), 1.28 (3H, d, J=6.3 Hz), 3.29 (1H, dd, J$_1$=5.7 Hz, J$_2$=2.7 Hz), 3.45-3.6 (1H, m), 4.2-4.35 (2H, m), 4.85 (2H, s), 5.29 (1H, d, J=13.8 Hz), 5.50 (1H, d, J=13.8 Hz), 6.53 (1H, d, J=10.5 Hz), 7.12 (1H, d, J=10.5 Hz), 7.68 (2H, d, J=8.7 Hz), 8.22 (2H, d, J=8.7 Hz), 8.76 (1H, s)

b) 4-Nitrobenzyl (1R,5S,6S)-2-[[(Z)-2-(4-acetoxymethylthiazol-5-yl)ethen-1-yl]thio]-1-methyl-6-((1R)-1-triethylsilyloxyethyl)-1-carbapen-2-em-3-carboxylate N,N-Dimethylaminopyridine (37 mg), 0.133 ml of pyridine, and 0.114 ml of acetic anhydride were added to 3 ml of a solution of 695 mg of 4-nitrobenzyl (1R,5S,6S)-2-[[(Z)-2-(4-hydroxymethylthiazol-5-yl)ethen-1-yl]thio]-1-methyl-6-((1R)-1-triethylsilyloxyethyl)-1-carbapen-2-em-3-carboxylate in THF, and the mixture was stirred at room temperature for 1.5 hr. Ethyl acetate was added to the reaction solution, and the mixture was washed with brine, was dried over anhydrous magnesium sulfate, and was filtered. Silica gel (5 g) was added to the filtrate, the mixture was filtered, and the filtrate was concentrated under the reduced pressure to give 730 mg of 4-nitrobenzyl (1R,5S,6S)-2-[[(Z)-2-(4-acetoxymethylthiazol-5-yl)ethen-1-yl]thio]-1-methyl-6-((1R)-1-triethylsilyloxyethyl)-1-carbapen-2-em-3-carboxylate.
NMR (CDCl$_3$) δ: 0.55-0.65 (6H, m), 0.9-1.0 (9H, m), 1.21 (3H, d, J=7.2 Hz), 1.28 (3H, d, J=6.4 Hz), 2.10 (3H, s), 3.30 (1H, dd, J$_1$=6.0 Hz, J$_2$=2.9 Hz), 3.5-3.6 (1H, m), 4.2-4.3 (2H, m), 5.25-5.35 (3H, m), 5.50 (1H, d, J=13.7 Hz), 6.59 (1H, d, J=10.5 Hz), 7.19 (1H, d, J=10.5 Hz), 7.68 (2H, d, J=9.0 Hz), 8.23 (2H, d, J=9.0 Hz), 8.79 (1H, s)

c) Sodium (1R,5S,6S)-2-[[(Z)-2-(4-acetoxymethylthiazol-5-yl)ethen-1-yl]thio]-6-((1R)-1-hydroxyethyl)-1-methyl-1-carbapen-2-em-3-carboxylate In the same manner as in step c) in Example 42, 305 mg of the title compound was prepared from 725 mg of 4-nitrobenzyl (1R,5S,6S)-2-[[(Z)-2-(4-acetoxymethylthiazol-5-yl)ethen-1-yl]thio]-1-methyl-6-((1R)-1-triethylsilyloxyethyl)-1-carbapen-2-em-3-carboxylate.
NMR (D$_2$O) δ (HOD=4.80 ppm): 1.12 (3H, d, J=7.2 Hz), 1.28 (3H, d, J=6.3 Hz), 2.09 (3H, s), 3.44 (1H, dd, J$_1$=6.3 Hz, J$_2$=2.7 Hz), 3.5-3.65 (1H, m), 4.2-4.3 (2H, m), 5.29 (2H, s), 6.81 (1H, d, J=10.5 Hz), 7.12 (1H, d, J=10.5 Hz), 8.96 (1H, s)

Example 80

Sodium (1R,5S,6S)-2-[[(Z)-2-[4-(2-acetoxyethoxy)methylthiazol-5-yl]ethen-1-yl]thio]-6-((1R)-1-hydroxyethyl)-1-methyl-1-carbapen-2-em-3-carboxylate a) 4-Nitrobenzyl (1R,5S,6S)-2-[[(Z)-2-[4-(2-acetoxyethoxy)methylthiazol-5-yl]ethen-1-yl]thio]-1-methyl-6-((1R)-1-triethylsilyloxyethyl)-1-carbapen-2-em-3-carboxylate In the same manner as in step b) in Example 79, 319 mg of 4-nitrobenzyl (1R,5S,6S)-2-[[(Z)-2-[4-(2-acetoxyethoxy)methylthiazol-5-yl]ethen-1-yl]thio]-1-methyl-6-((1R)-1-triethylsilyloxyethyl)-1-carbapen-2-em-3-carboxylate was prepared from 270 mg of 4-nitrobenzyl (1R,5S,6S)-2-[[(Z)-2-[4-(2-hydroxyethoxy)methylthiazol-5-yl]ethen-1-yl]thio]-1-methyl-6-((1R)-1-triethylsilyloxy ethyl)-1-carbapen-2-em-3-carboxylate prepared in step b) in Example 42.

NMR (CDCl$_3$) δ: 0.55-0.65 (6H, m), 0.9-1.0(9H, m), 1.20 (3H, d, J=7.3 Hz), 1.28 (3H, d, J=6.3 Hz), 2.07 (3H, s), 3.29 (1H, dd, J$_1$=5.8 Hz, J$_2$=2.9 Hz), 3.5-3.6 (1H, m), 3.7-3.75 (2H, m), 4.2-4.3 (4H, m), 4.81 (2H, s), 5.30 (1H, d, J=14.2 Hz), 5.51 (1H, d, J=14.2 Hz), 6.53 (1H, d, J=10.5 Hz), 7.24 (1H, d, J=10.5 Hz), 7.68 (2H, d, J=8.8 Hz), 8.23 (2H, d, J=8.8 Hz), 8.75 (1H, s)

b) Sodium (1R,5S,6S)-2-[[(Z)-2-[4-(2-acetoxy-ethoxy)methylthiazol-5-yl]ethen-1-yl]thio]-6-((1R)-1-hydroxyethyl)-1-methyl-1-carbapen-2-em-3-carboxylate In the same manner as in step c) in Example 42, 135 mg of the title compound was prepared from 315 mg of 4-nitrobenzyl (1R,5S,6S)-2-[[(Z)-2-[4-(2-acetoxyethoxy)methylthiazol-5-yl]ethen-1-yl]thio]-1-methyl-6-((1R)-1-triethylsilyloxyethyl)-1-carbapen-2-em-3-carboxylate.

NMR (D$_2$O) δ (HOD=4.80 ppm): 1.21 (3H, d, J=7.2 Hz), 1.29 (3H, d, J=6.3 Hz), 2.07 (3H, s), 3.4-3.5 (1H, m), 3.55-3.65 (1H, m), 3.75-3.85 (2H, m), 4.2-4.3 (4H, m), 6.80 (1H, d, J=10.5 Hz), 7.13 (1H, d, J=10.5 Hz), 8.96 (1H, s)

Example 81

1-(Cyclohexyloxycarbonyloxy)ethyl (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate (diastereomer mixture)

A solution (2 ml) of 0.147 mg of 1-(cyclohexyloxycarbonyloxy)ethyl iodide in hexane was added to a solution of 51.8 mg of sodium (1R,5S,6S)-2-[[(Z)-2-[4-(2-hydroxyethoxy)methylthiazol-5-yl]ethen-1-yl]thio]-6-((1R)-1-hydroxyethyl)-1-methyl-1-carbapen-2-em-3-carboxylate in 2 ml of N,N-dimethylacetamide under an argon atmosphere at −10° C. The mixture was stirred at the same temperature for one hr, and 2 ml of hexane was then added to the reaction solution, followed by separation into an upper layer and a lower layer. Brine was added to the lower layer, and the mixture was extracted twice with ethyl acetate. The organic layers were combined, were washed twice with brine, were dried over anhydrous magnesium sulfate, were filtered, and were concentrated under the reduced pressure, and the residue was purified by column chromatography on silica gel (chloroform:methanol=20:1) to give 61.7 mg of the title compound.

NMR (CDCl$_3$) δ: 1.2-2.0 (19H, m), 3.2-3.3 (1H, m), 3.5-3.6 (1H, m), 3.65-3.8 (4H, m), 4.2-4.3 (2H, m), 4.6-4.7 (1H, m), 4.81 (2H, s), 6.52 (1H, d, J=10.2 Hz), 6.85-7.0 (1H, m), 7.1-7.2 (1H, m), 8.77, 8.78 (total 1H, 2s)

Example 82

1-(Cyclohexyloxycarbonyloxy)ethyl (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate (diastereomer mixture)

In the same manner as in Example 81, 969 mg of the title compound was prepared from 667 mg of sodium (1R,5S,6S)-2-[[(Z)-2-(4-N,N-dimethylcarbamoylthiazol-5-yl)ethen-1-yl]thio]-6-((1R)-1-hydroxyethyl)-1-methyl-1-carbapen-2-em-3-carboxylate prepared in Example 43.

NMR (CDCl$_3$) δ: 1.19 (3H, d, J=7.3 Hz), 1.20-2.00 (16H, m), 3.03 (3H, m), 3.14 (3H, m), 3.26-3.31 (1H, m), 3.50-3.60 (1H, m), 4.21-4.30 (2H, m), 4.60-4.71 (1H, m), 6.55 (1H, d, J=10.5 Hz), 6.90-6.96 (1H, m), 7.36-7.40 (1H, m), 8.76 (1H, m)

Example 83

1-(Cyclohexyloxycarbonyloxy)ethyl (1R,5S,6S)-6-((1R)-1-hydroxyethyl)-2-[[(Z)-2-(4-hydroxymethylthiazol-2-yl)ethen-1-yl]thio]-1-methyl-1-carbapen-2-em-3-carboxylate (diastereomer mixture)

In the same manner as in Example 81, 52.7 mg of the title compound was prepared from 42.9 mg of sodium (1R,5S,6S)-6-((1R)-1-hydroxyethyl)-2-[[(Z)-2-(4-hydroxymethylthiazol-2-yl)ethen-1-yl]thio]-1-methyl-1-carbapen-2-em-3-carboxylate and 48 mg of 1-(cyclohexyloxycarbonyloxy)ethyl iodide.

NMR (CDCl$_3$) δ: 1.2-2.0 (19H, m), 3.25-3.35 (1H, m), 3.6-3.75 (1H, m), 4.2-4.3 (2H, m), 4.6-4.7 (1H, m), 4.7-4.9 (2H, m), 6.8-7.0 (3H, m), 7.26 (1H, s)

Example 84

1-(Cyclohexyloxycarbonyloxy)ethyl (1R,5S,6S)-2-[[(Z)-2-(4-carbamoylthiazol-5-yl)ethen-1-yl]thio]-6-((1R)-1-hydroxyethyl)-1-methyl-1-carbapen-2-em-3-carboxylate (diastereomer mixture)

In the same manner as in Example 81, 54 mg of the title compound was prepared from 70 mg of sodium (1R,5S,6S)-2-[[(Z)-2-(4-carbamoylthiazol-5-yl)ethen-1-yl]thio]-6-((1R)-1-hydroxyethyl)-1-methyl-1-carbapen-2-em-3-carboxylate prepared in Example 46.

NMR (CDCl$_3$) δ: 1.19 (3H, d, J=6.7 Hz), 1.21-2.00 (16H, m), 3.26-3.32 (1H, m), 3.53-3.65 (1H, m), 4.20-4.31 (2H, m), 4.60-4.71 (1H, m), 5.63 (1H, brs), 6.69 (1H, d, J=10.5 Hz), 6.88-6.96 (1H, m), 7.43 (1H, brs), 8.37-8.42 (1H, m), 8.69 (1H, m)

Example 85

1-(Cyclohexyloxycarbonyloxy)ethyl (1R,5S,6S)-2-[[(Z)-2-(4-N-cyanomethylcarbamoylthiazol-5-yl)ethen-1-yl]thio]-6-((1R)-1-hydroxyethyl)-1-methyl-1-carbapen-2-em-3-carboxylate (diastereomer mixture)

In the same manner as in Example 81, 57 mg of the title compound was prepared from 60 mg of sodium (1R,5S,6S)-2-[[(Z)-2-(4-N-cyanomethylcarbamoylthiazol-5-yl)ethen-1-yl]thio]-6-((1R)-1-hydroxyethyl)-1-methyl-1-carbapen-2-em-3-carboxylate prepared in Example 49.

NMR (CDCl$_3$) δ: 1.20 (3H, d, J=7.3 Hz), 1.21-2.00 (16H, m), 3.26-3.32 (1H, m), 3.53-3.66 (1H, m), 4.22-4.32 (2H, m), 4.34-4.38 (2H, m), 4.60-4.71 (1H, m), 6.69 (1H, d, J=10.7 Hz), 6.89-6.96 (1H, m), 7.91-7.97 (1H, m), 8.31-8.36 (1H, m), 8.70 (1H, m)

Example 86

1-(Cyclohexyloxycarbonyloxy)ethyl (1R,5S,6S)-6-((1R)-1-hydroxyethyl)-2-[[(Z)-2-[4-N-(2-hydroxyethyl)carbamoyl-thiazol-5-yl]ethen-1-yl]thio]-1-methyl-1-carbapen-2-em-3-carboxylate (diastereomer mixture)

In the same manner as in Example 81, 85.6 mg of the title compound was prepared from 69 mg of sodium (1R,5S,6S)-6-((1R)-1-hydroxyethyl)-2-[[(Z)-2-[4-N-(2-hydroxyethyl)carbamoyl-thiazol-5-yl]ethen-1-yl]thio]-1-m ethyl-1-carbapen-2-em-3-carboxylate.
NMR (CDCl$_3$) δ: 1.2-2.0 (19H, m), 3.25-3.3 (1H, m), 3.5-3.6 (3H, m), 3.8-3.9 (2H, m), 4.2-4.3 (2H, m), 4.6-4.7 (1H, m), 6.69 (1H, d, J=10.8 Hz), 6.9-7.0 (1H, m), 8.0-8.1 (1H, m), 8.39 (1H, d, J=10.8 Hz), 8.67, 8.68 (total 1H, both s)

Example 87

Pivaloyloxymethyl (1R,5S,6S)-2-[[(Z)-2-(2-carbamoylthiazol-5-yl)ethen-1-yl]thio]-6-((1R)-1-hydroxyethyl)-1-methyl-1-carbapen-2-em-3-carboxylate In the same manner as in Example 81, 78 mg of the title compound was prepared from 74 mg of sodium (1R,5S,6S)-2-[[(Z)-2-(2-carbamoylthiazol-5-yl)ethen-1-yl]thio]-6-((1R)-1-hydroxyethyl)-1-methyl-1-carbapen-2-em-3-carboxylate prepared in Example 62 and 0.031 ml of iodomethyl pivalate.
NMR (CDCl$_3$) δ: 1.20 (3H, d, J=7.3 Hz), 1.23 (9H, s), 1.34 (3H, d, J=6.4 Hz), 3.28-3.34 (1H, m), 3.46-3.62 (1H, m), 4.22-4.33 (2H, m), 5.55 (1H, brs), 5.88 (1H, d, J=5.6 Hz), 6.00 (1H, d, J=5.6 Hz), 6.61 (1H, d, J=10.3 Hz), 6.98 (1H, d, J=10.3 Hz), 7.10 (1H, brs), 7.91 (1H, s)

Example 88

1-(Cyclohexyloxycarbonyloxy)ethyl (1R,5S,6S)-6-((1R)-1-hydroxyethyl)-2-[[(Z)-2-[4-N-(2-hydroxyethyl)carbamoylthiazol-2-yl]ethen-1-yl]thio]-1-methyl-1-carbapen-2-em-3-carboxylate (diastereomer mixture)

In the same manner as in Example 81, 45 mg of the title compound was prepared from 38.5 mg of sodium (1R,5S,6S)-6-((1R)-1-hydroxyethyl)-2-[[(Z)-2-[4-N-(2-hydroxyethyl)carbamoyl-thiazol-2-yl]ethen-1-yl]thio]-1-m ethyl-1-carbapen-2-em-3-carboxylate and 123 mg of 1-(cyclohexyloxycarbonyloxy)ethyl iodide.
NMR (CDCl$_3$) δ: 1.1-2.0 (19H, m), 3.25-3.4 (2H, m), 3.6-4.0 (4H, m), 4.2-4.35 (2H, m), 4.6-4.7 (1H, m), 6.78 (1H, d, J=10.5 Hz), 6.85-7.0 (2H, m), 7.9-8.0 (1H, m), 8.06, 8.08 (total 1H, 2s)

Example 89

1-(Cyclohexyloxycarbonyloxy)ethyl(1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 484 mg of the title compound was prepared from 379 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 1.1-2.0 (19H, m), 2.6-2.7 (1H, m), 3.2-3.3 (1H, m), 3.45-3.6 (1H, m), 4.2-4.3 (2H, m), 4.6-4.75 (1H, m), 4.8-4.9 (2H, m), 6.51 (1H, d, J=10.2 Hz), 6.9-7.0 (1H, m), 7.05-7.15 (1H, m), 8.77, 8.78 (total 1H, 2s)

Example 90

Acetoxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 146 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate prepared in Example 41 and 0.047 ml of bromomethyl acetate. NMR (CDCl$_3$) δ: 1.21 (3H, d, J=7.3 Hz), 1.35 (3H, d, J=6.3 Hz), 1.83 (1H, d, J=4.8 Hz), 2.14 (3H, s), 2.50 (1H, t, J=5.9 Hz), 3.29 (1H, dd, J$_1$=6.8 Hz, J$_2$=2.8 Hz), 3.51-3.61 (1H, m), 4.22-4.31 (2H, m), 4.86 (2H, d, J=5.9 Hz), 5.89 (1H, d, J=5.6 Hz), 5.97 (1H, d, J=5.6 Hz), 6.52 (1H, d, J=10.5 Hz), 7.13 (1H, d, J=10.5 Hz), 8.79 (1H, s)

Example 91

1-(Isopropyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 137 mg of the title compound was prepared from 133 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate prepared in Example 41 and 110 mg of 1-(isopropyloxycarbonyloxy)ethyl iodide.
NMR (CDCl$_3$) δ: 1.19 (3H, d, J=7.3 Hz), 1.26-1.37 (9H, m), 1.61-1.65 (3H, m), 1.80 (1H, d, J=4.7 Hz), 2.50 (1H, t, J=5.9 Hz), 3.28 (1H, dd, J$_1$=6.7 Hz, J$_2$=2.8 Hz), 3.51-3.61 (1H, m), 4.22-4.30 (2H, m), 4.85 (2H, d, J=5.9 Hz), 4.87-4.96 (1H, m), 6.52 (1H, d, J=10.2 Hz), 6.90-6.95 (1H, m), 7.09-7.14 (1H, m), 8.78 (1H, m)

Example 92

1-(Ethoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 167 mg of the title compound was prepared from 145 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 148 mg of 1-(ethoxycarbonyloxy)ethyl iodide.
NMR (CDCl$_3$) δ: 1.19 (3H, d, J=6.9 Hz), 1.3-1.4 (6H, m), 1.6-1.7 (3H, m), 2.05-2.2 (1H, m), 2.8-2.9 (1H, m), 3.05-3.1 (1H, m), 3.45-3.6 (1H, m), 4.2-4.3 (4H, m), 4.8-4.9 (2H, m), 6.51 (1H, d, J=10.5 Hz), 6.9-7.0 (1H, m), 7.1-7.2 (1H, m), 8.77, 8.78 (total 1H, both s)

Example 93

Pivaloyl oxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 93 mg of the title compound was prepared from 104 mg of sodium (1R,5S,6S)-

6-((1R)-1-hydroxyethyl)-2-[[(Z)-2-(4-hydroxymethylthiazol-5-yl)ethen-1-yl]thio]-1-methyl-1-carbapen-2-em-3-carboxylate prepared in Example 41 and 0.049 ml of iodomethyl pivalate.

NMR (CDCl$_3$) δ: 1.20 (3H, d, J=7.2 Hz), 1.23 (9H, s), 1.34 (3H, d, J=6.4 Hz), 1.80 (1H, d, J=4.8 Hz), 2.45 (1H, t, J=5.8 Hz), 3.29 (1H, dd, J$_1$=6.4 Hz, J$_2$=2.6 Hz), 3.50-3.60 (1H, m), 4.22-4.30 (2H, m), 4.86 (2H, d, J=5.6 Hz), 5.89 (1H, d, J=5.6 Hz), 6.00 (1H, d, J=5.6 Hz), 6.51 (1H, d, J=10.4 Hz), 7.13 (1H, d, J=10.4 Hz), 8.78 (1H, m)

Example 94

Cyclohexyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 372 mg of the title compound was prepared from 374 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 336 mg of cyclohexyloxycarbonyloxymethyl iodide.

NMR (DMSO-d$_6$) δ: 1.08 (3H, d, J=7.3 Hz), 1.14 (3H, d, J=6.4 Hz), 1.20-1.88 (10H, m), 3.78-3.86 (1H, m), 3.94-4.03 (1H, m), 4.24 (1H, dd, J$_1$=9.8 Hz, J$_2$=2.9 Hz), 4.56-4.64 (1H, m), 4.67 (2H, d, J=5.6 Hz), 5.13 (1H, d, J=5.1 Hz), 5.33 (1H, t, J=5.6 Hz), 5.78 (1H, d, J=6.2 Hz), 5.89 (1H, d, J=6.2 Hz), 6.86 (1H, d, J=10.4 Hz), 7.37 (1H, d, J=10.4 Hz), 9.07 (1H, s)

Example 95

1-(Isobutyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 334 mg of the title compound was prepared from 346 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate prepared in Example 41 and 278 mg of 1-(isobutyloxycarbonyloxy)ethyl iodide.

NMR (CDCl$_3$) δ: 0.92-0.96 (6H, m), 1.19 (3H, d, J=7.3 Hz), 1.32-1.37 (3H, m), 1.64-1.71 (3H, m), 1.79 (1H, m), 1.92-2.04 (1H, m), 2.48 (1H, t, J=6.1 Hz), 3.26-3.31 (1H, m), 3.49-3.60 (1H, m), 3.93-3.99 (2H, m), 4.22-4.30 (2H, m), 4.85 (2H, d, J=6.1 Hz), 6.51 (1H, d, J=10.3 Hz), 6.89-6.96 (1H, m), 7.08-7.14 (1H, m), 8.78 (1H, m)

Example 96

1-(Cyclohexyloxycarbonyloxy)-2-methylpropan-1-yl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate (diastereomer mixture)

In the same manner as in Example 81, 84 mg of the title compound was prepared from 367 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 300 mg of 1-(cyclohexyloxycarbonyloxy)-2-methylpropan-1-yl iodide.

NMR (CDCl$_3$) δ: 1.1-2.2 (23H, m), 3.2-3.3 (1H, m), 3.5-3.6 (1H, m), 4.2-4.3 (2H, m), 4.6-4.7 (1H, m), 4.8-4.9 (2H, m), 6.5-6.6 (1H, m), 6.6-6.7 (1H, m), 7.1-7.2 (1H, m), 8.75-8.8 (1H, m)

Example 97

Isobutyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 294 mg of the title compound was prepared from 344 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 264 mg of isobutyloxycarbonyloxymethyl iodide.

NMR (CDCl$_3$) δ: 0.94 (6H, d, J=6.6 Hz), 1.19 (3H, d, J=7.2 Hz), 1.34 (3H, d, J=6.3 Hz), 1.9-2.05 (1H, m), 2.1-2.25 (1H, m), 2.75-2.9 (1H, m), 3.28 (1H, dd, J$_1$=6.6 Hz, J$_2$=2.7 Hz), 3.5-3.6 (1H, m), 3.98 (2H, d, J=6.6 Hz), 4.2-4.3 (2H, m), 4.8-4.9 (2H, m), 5.91 (1H, d, J=5.4 Hz), 5.97 (1H, d, J=5.4 Hz), 6.51 (1H, d, J=10.5 Hz), 7.15 (1H, d, J=10.5 Hz), 8.78 (1H, s)

Example 98

Isopropyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 203 mg of the title compound was prepared from 348 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 252 mg of isopropyloxycarbonyloxymethyl iodide.

NMR (CDCl$_3$) δ: 1.19 (3H, d, J=7.2 Hz), 1.3-1.4 (9H, m), 2.05-2.1 (1H, m), 2.7-2.8 (1H, m), 3.28 (1H, dd, J$_1$=6.6 Hz, J$_2$=2.7 Hz), 3.5-3.6 (1H, m), 4.2-4.3 (2H, m), 4.85 (2H, d, J=5.4 Hz), 4.9-5.0 (1H, m), 5.89 (1H, d, J=5.4 Hz), 5.97 (1H, d, J=5.4 Hz), 6.51 (1H, d, J=10.5 Hz), 7.14 (1H, d, J=10.5 Hz), 8.78 (1H, s)

Example 99

Isobutyryloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 360 mg of the title compound was prepared from 325 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 220 mg of isobutyryloxymethyl iodide.

NMR (CDCl$_3$) δ: 1.05-1.25 (9H, m), 1.33 (3H, d, J=6.3 Hz), 2.55-2.7 (1H, m), 3.28 (1H, dd, J$_1$=6.6 Hz, J$_2$=2.4 Hz), 3.5-3.6 (1H, m), 4.2-4.3 (2H, m), 4.84 (2H, s), 5.89 (1H, d, J=5.4 Hz), 5.99 (1H, d, J=5.4 Hz), 6.52 (1H, d, J=10.5 Hz), 7.16 (1H, d, J=10.5 Hz), 8.78 (1H, s)

Example 100

(Pentan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 168 mg of the title compound was prepared from 150 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 162 mg of (pentan-1-yl)oxycarbonyloxymethyl iodide.

NMR (CDCl$_3$) δ: 0.87-0.91 (3H, m), 1.20 (3H, d, J=7.4 Hz), 1.27-1.36 (7H, m), 1.65-1.74 (3H, m), 2.41 (1H, t, J=6.1 Hz), 3.28 (1H, dd, J$_1$=6.7 Hz, J$_2$=2.8 Hz), 3.55 (1H, m), 4.19 (2H, t, J=6.7 Hz), 4.22-4.28 (2H, m), 4.85 (2H, d, J=5.9 Hz), 5.91 (1H, d, J=5.6 Hz), 5.97 (1H, d, J=5.6 Hz), 6.51 (1H, d, J=10.2 Hz), 7.14 (1H, dd, J$_1$=10.2 Hz, J$_2$=1.0 Hz), 8.78 (1H, s)

Example 101

(Butan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 223 mg of the title compound was prepared from 175 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 164 mg of (butan-1-yl)oxycarbonyloxymethyl iodide.

NMR (CDCl$_3$) δ: 0.92 (3H, t, J=7.5 Hz), 1.20 (3H, d, J=7.2 Hz), 1.3-1.5 (5H, m), 1.6-1.7 (2H, m), 3.28 (1H, dd, J$_1$=6.9 Hz, J$_2$=2.7 Hz), 3.5-3.6 (1H, m), 4.15-4.3 (4H, m), 4.86 (2H, s), 5.90 (1H, d, J=5.7 Hz), 5.97 (1H, d, J=5.7 Hz), 6.51 (1H, d, J=10.2 Hz), 7.14 (1H, d, J=10.2 Hz), 8.79 (1H, s)

Example 102

(1-Ethylpropan-1-yl)oxycarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in Example 81, 154 mg of the title compound was prepared from 149 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 120 mg of (1-ethylpropan-1-yl)oxycarbonyloxymethyl iodide.

NMR (CDCl$_3$) δ: 0.85-0.95 (6H, m), 1.20 (3H, d, J=7.2 Hz), 1.34 (3H, d, J=6.3 Hz), 1.55-1.7 (4H, m), 1.8-1.9 (1H, m), 2.45-2.55 (1H, m), 3.28 (1H, dd, J$_1$=6.6 Hz, J$_2$=2.4 Hz), 3.5-3.6 (1H, m), 4.2-4.3 (2H, m), 4.6-4.7 (1H, m), 4.86 (2H, d, J=5.7 Hz), 5.91 (1H, d, J=5.4 Hz), 5.98 (1H, d, J=5.4 Hz), 6.50 (1H, d, J=10.5 Hz), 7.13 (1H, d, J=10.5 Hz), 8.78 (1H, s)

Example 103

Isopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 153 mg of the title compound was prepared from 150 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 120 mg of isopentyloxycarbonyloxymethyl iodide.

NMR (CDCl$_3$) δ: 0.91 (6H, d, J=6.6 Hz), 1.20 (3H, d, J=7.2 Hz), 1.34 (3H, d, J=6.0 Hz), 1.5-1.6 (2H, m), 1.6-1.8 (1H, m), 1.8-1.9 (1H, m), 2.45-2.55 (1H, m), 3.28 (1H, dd, J$_1$=6.9 Hz, J$_2$=2.7 Hz), 3.5-3.6 (1H, m), 4.2-4.3 (4H, m), 4.8-4.85 (2H, m), 5.90 (1H, d, J=5.7 Hz), 5.97 (1H, d, J=5.7 Hz), 6.51 (1H, d, J=10.2 Hz), 7.14 (1H, d, J=10.2 Hz), 8.78 (1H, s)

Example 104

(Propan-1-yl)oxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 177 mg of the title compound was prepared from 150 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 109 mg of (propan-1-yl)oxymethyl iodide.

NMR (CDCl$_3$) δ: 0.96 (3H, t, J=7.5 Hz), 1.20 (3H, d, J=6.9 Hz), 1.35 (3H, d, J=6.3 Hz), 1.65-1.75 (2H, m), 1.75-1.85 (1H, m), 2.45-2.55 (1H, m), 3.28 (1H, dd, J$_1$=6.6 Hz, J$_2$=2.7 Hz), 3.5-3.6 (1H, m), 4.1-4.35 (4H, m), 4.86 (2H, d, J=6.0 Hz), 5.91 (1H, d, J=5.7 Hz), 5.97 (1H, d, J=5.7 Hz), 6.51 (1H, d, J=10.2 Hz), 7.14 (1H, d, J=10.2 Hz), 8.78 (1H, s)

Example 105

1-(Cyclohexyloxycarbonyloxy)ethyl (1R,5S,6S)-2-[[(Z)-2-(4-acetoxymethylthiazol-5-yl)ethen-1-yl]thio]-6-((1R)-1-hydroxyethyl)-1-methyl-1-carbapen-2-em-3-carboxylate (diastereomer mixture)

In the same manner as in Example 81, 159 mg of the title compound was prepared from 130 mg of sodium (1R,5S,6S)-2-[[(Z)-2-(4-acetoxymethylthiazol-5-yl)ethen-1-yl]thio]-6-((1R)-1-hydroxyethyl)-1-methyl-1-carbapen-2-em-3-carboxylate prepared in Example 79 and 104 mg of 1-(cyclohexyloxycarbonyloxy)ethyl iodide.

NMR (CDCl$_3$) δ: 1.2-2.1 (19H, m), 2.10 (3H, s), 3.25-3.3 (1H, m), 3.5-3.6 (1H, m), 4.2-4.3 (2H, m), 4.6-4.75 (1H, m), 5.31 (2H, s), 6.57 (1H, d, J=10.5 Hz), 6.9-7.0 (1H, m), 7.1-7.2 (1H, m), 8.80, 8.81 (total 1H, 2s)

Example 106

Ethoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 203 mg of the title compound was prepared from 214 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 146 mg of ethoxycarbonyloxymethyl iodide.

NMR (CDCl$_3$) δ: 1.20 (3H, d, J=7.3 Hz), 1.30-1.35 (6H, m), 1.74 (1H, d, J=4.6 Hz), 2.42 (1H, t, J=6.1 Hz), 3.28 (1H, dd, J$_1$=6.8 Hz, J$_2$=2.7 Hz), 3.5-3.6 (1H, m), 4.2-4.3 (4H, m), 4.8-4.9 (2H, m), 5.91 (1H, d, J=5.6 Hz), 5.98 (1H, d, J=5.6 Hz), 6.51 (1H, d, J=10.2 Hz), 7.29 (1H, d, J=10.2 Hz), 8.78 (1H, s)

Example 107

Neopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 193 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 129 mg of neopentyloxycarbonyloxymethyl iodide.

NMR (CDCl$_3$) δ: 0.95 (9H, s), 1.19 (3H, d, J=7.2 Hz), 1.34 (3H, d, J=6.3 Hz), 2.2-2.3 (1H, m), 2.9-3.0 (1H, m), 3.28 (1H, dd, J$_1$=6.6 Hz, J$_2$=2.4 Hz), 3.5-3.6 (1H, m), 3.89 (2H, s), 4.2-4.3 (2H, m), 4.85 (2H, d, J=4.8 Hz), 5.92 (1H, d, J=6.0 Hz), 5.97 (1H, d, J=6.0 Hz), 6.52 (1H, d, J=10.2 Hz), 7.15 (1H, d, J=10.2 Hz), 8.78 (1H, s)

Example 108

Methoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 148 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 103 mg of methoxycarbonyloxymethyl iodide.

NMR (CDCl$_3$) δ: 1.18 (3H, d, J=7.2 Hz), 1.32 (3H, d, J=6.3 Hz), 2.75-2.9 (1H, m), 3.28 (1H, dd, J$_1$=6.6 Hz, J$_2$=2.7 Hz), 3.35-3.5 (1H, m), 3.5-3.6 (1H, m), 3.84 (3H, s), 4.2-4.3 (2H, m), 4.8-4.9 (2H, m), 5.90 (1H, d, J=5.4 Hz), 5.97 (1H, d, J=5.4 Hz), 6.52 (1H, d, J=10.2 Hz), 7.16 (1H, d, J=10.2 Hz), 8.79 (1H, s)

Example 109

Cyclopentyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 167 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 128 mg of cyclopentyloxycarbonyloxymethyl iodide.

NMR (CDCl$_3$) δ: 1.19 (3H, d, J=6.9 Hz), 1.33 (3H, d, J=6.0 Hz), 1.5-1.9 (8H, m), 2.4-2.5 (1H, m), 3.0-3.2 (1H, m), 3.28 (1H, dd, J$_1$=6.6 Hz, J$_2$=2.4 Hz), 3.5-3.6 (1H, m), 4.2-4.3 (2H, m), 4.85 (2H, s), 5.1-5.2 (1H, m), 5.88 (1H, d, J=5.7 Hz), 5.96 (1H, d, J=5.7 Hz), 6.52 (1H, d, J=10.2 Hz), 7.15 (1H, d, J=10.2 Hz), 8.79 (1H, s)

Example 110 t-Butoxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 214 mg of the title compound was prepared from 176 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 135 mg of t-butoxycarbonyloxymethyl iodide.

NMR (CDCl$_3$) δ: 1.18 (3H, d, J=7.2 Hz), 1.33 (3H, d, J=6.3 Hz), 1.49 (9H, s), 2.5-2.6 (1H, m), 3.2-3.3 (2H, m), 3.5-3.6 (1H, m), 4.26 (1H, dd, J$_1$=9.3 Hz, J$_2$=2.4 Hz), 4.84 (2H, d, J=3.3 Hz), 5.84 (1H, d, J=5.7 Hz), 5.93 (1H, d, J=5.7 Hz), 6.52 (1H, d, J=9.9 Hz), 7.15 (1H, d, J=9.9 Hz), 8.78 (1H, s)

Example 111

Phthalidyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

The title compound (122 mg) was prepared from 162 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 128 mg of 3-bromophthalide in the same manner as in Example 81, except that only DMA was used as the solvent and the reaction was carried out at room temperature.

NMR (CDCl$_3$) δ: 1.20-1.24 (3H, m), 1.30-1.34 (3H, m), 1.69 & 1.75 (total 1H, br s×2), 2.43 (1H, m), 3.28-3.31 (1H, m), 3.54-3.61 (1H, m), 4.24-4.27 (total 1H, d×2, J=2.9 Hz), 4.2 & 4.8 (total 1H, br s×2), 4.82-4.87 (total 1H, d×2, J=5.2 Hz), 6.45-6.53 (total 1H, d×2, J=10.3 Hz), 7.07-7.17 (total 1H, d×2, J=10.3 Hz), 7.52 & 7.56 (total 1H, s×2), 7.64-7.77 (3H, m), 7.91-7.95 (total 1H, m), 8.73 & 8.79 (total 1H, s×2)

Example 112

1-(Methoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 145 mg of the title compound was prepared from 163 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 140 mg of 1-(methoxycarbonyloxy)ethyl iodide.

NMR (CDCl$_3$) δ: 1.19 (3H, d, J=7.2 Hz), 1.3-1.4 (3H, m), 1.6-1.7 (3H, m), 2.1-2.3 (1H, m), 2.8-3.0 (1H, m), 3.25-3.3 (1H, m), 3.5-3.6 (1H, m), 3.81, 3.83 (total 3H, 2 s), 4.2-4.3 (2H, m), 4.85 (2H, d, J=3.9 Hz), 6.52 (1H, d, J=10.2 Hz), 6.9-7.0 (1H, m), 7.1-7.2 (1H, m), 8.79 (1H, s)

Example 113

1-(Cyclopentyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 187 mg of the title compound was prepared from 162 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 148 mg of 1-(cyclopentyloxycarbonyloxy)ethyl iodide.

NMR (CDCl$_3$) δ: 1.18 (3H, d, J=7.2 Hz), 1.3-1.4 (3H, m), 1.5-2.0 (11H, m), 2.2-2.4 (1H, m), 2.9-3.05 (1H, m), 3.25-3.35 (1H, m), 3.45-3.6 (1H, m), 4.2-4.3 (2H, m), 4.85 (2H, d,

J=4.8 Hz), 5.1-5.2 (1H, m), 6.52 (1H, d, J=10.5 Hz), 6.85-7.0 (1H, m), 7.1-7.2 (1H, m), 8.77, 8.78 (total 1H, 2s)

Example 114

(Tetrahydropyran-4-yl)oxycarbonyloxymethyl (1R, 5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in Example 81, 194 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 136 mg of (tetrahydropyran-4-yl)oxycarbonyloxymethyl iodide.

NMR (CDCl$_3$) δ: 1.19 (3H, d, J=7.5 Hz), 1.33 (3H, d, J=6.0 Hz), 1.7-1.9 (2H, m), 1.9-2.05 (2H, m), 2.4-2.6 (1H, m), 3.0-3.2 (1H, m), 3.25-3.3 (1H, m), 3.45-3.6 (3H, m), 3.85-4.0 (2H, m), 4.2-4.3 (2H, m), 4.8-4.95 (3H, m), 5.88 (1H, d, J=5.7 Hz), 6.00 (1H, d, J=5.7 Hz), 6.52 (1H, d, J=10.5 Hz), 7.16 (1H, d, J=10.5 Hz), 8.79 (1H, s)

Example 115

1-(Neopentyloxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 100 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 170 mg of 1-(neopentyloxycarbonyloxy)ethyl iodide.

NMR (CDCl$_3$) δ: 0.95 (9H, s), 1.19 (3H, d, J=6.9 Hz), 1.3-1.4 (3H, m), 1.6-1.7 (3H, m), 2.0-2.1 (1H, m), 2.7-2.85 (1H, m), 3.25-3.3 (1H, m), 3.5-3.6 (1H, m), 3.8-3.95 (2H, m), 4.2-4.3 (2H, m), 4.85 (2H, s), 6.51 (1H, d, J=10.5 Hz), 6.9-7.0 (1H, m), 7.1-7.2 (1H, m), 8.78 (1H, s)

Example 116

(Piperidin-1-yl)carbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 192 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 130 mg of (piperidin-1-yl)carbonyloxymethyl iodide.

NMR (CDCl$_3$) δ: 1.19 (3H, d, J=7.5 Hz), 1.33 (3H, d, J=6.0 Hz), 1.45-1.65 (6H, m), 2.25-2.4 (1H, m), 2.75-2.9 (1H, m), 3.27 (1H, dd, J$_1$=6.9 Hz, J$_2$=2.7 Hz), 3.4-3.6 (5H, m), 4.2-4.3 (2H, m), 4.85 (2H, d, J=5.1 Hz), 5.92 (1H, d, J=5.7 Hz), 5.99 (1H, d, J=5.7 Hz), 6.51 (1H, d, J=10.5 Hz), 7.13 (1H, d, J=10.5 Hz), 8.78 (1H, s)

Example 117

Allyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 984 mg of the title compound was prepared from 1.00 g of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate prepared in Example 41, 538 mg of allyl bromide, and 415 mg of allyl iodide.

NMR (CDCl$_3$) δ: 1.20 (3H, d, J=7.3 Hz), 1.35 (3H, d, J=6.1 Hz), 3.29 (1H, dd, J$_1$=6.6 Hz, J$_2$=2.7 Hz), 3.54 (1H, m), 4.25-4.28 (2H, m), 4.73 (1H, m), 4.85-4.89 (3H, m), 5.28 (1H, d, J=10.5 Hz), 5.48 (1H, m), 5.95-6.04 (1H, m), 6.53 (1H, d, J=10.5 Hz), 7.11 (1H, d, J=10.2 Hz), 8.77 (1H, s)

Example 118

(1R,5S,6S)-6-((1R)-1-Hydroxyethyl)-1-methyl-2-[[(Z)-2-(4-(L-valyloxymethyl)thiazol-5-yl)ethen-1-yl]thio]-1-carbapen-2-em-3-carboxylic acid a) Allyl (1R,5S,6S)-6-((1R)-1-hydroxyethyl)-1-methyl-2-[[(Z)-2-(4-(N-4-nitrobenzyloxycarbonyl-L-valyloxymethyl)thiazol-5-yl)ethen-1-yl]thio]-1-carbapen-2-em-3-carboxylate Allyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (970 mg) was dissolved in 10 ml of N,N-dimethylacetamide. 4-Dimethylaminopyridine (281 mg), 441 mg of 1-[3-(dimethylamino)propyl]-3-ethylcarbodiimide hydrochloride, and 681 mg of N-4-nitrobenzyloxycarbonyl-L-valine were added to the solution, and the mixture was stirred at room temperature overnight. The reaction mixture was poured into 50 ml of 20% brine and 50 ml of ethyl acetate, followed by separation. The organic layer was dried over magnesium sulfate. The magnesium sulfate was removed by filtration, and the solvent was removed by distillation under the reduced pressure. The crude product was purified by column chromatography on silica gel (ethyl acetate:n-hexane=2:1, and subsequently ethyl acetate:n-hexane=5:1) to give 517 mg of allyl (1R,5S,6S)-6-((1R)-1-hydroxyethyl)-1-methyl-2-[[(Z)-2-(4-(N-4-nitrobenzyloxycarbonyl-L-valyloxymethyl)thiazol-5-yl)ethen-1-yl]thio]-1-carbapen-2-em-3-carboxylate.

NMR (CDCl$_3$) δ: 0.83 (3H, d, J=6.8 Hz), 0.93 (3H, d, J=6.8 Hz), 1.20 (3H, d, J=7.3 Hz), 1.36 (3H, d, J=6.3 Hz), 2.05 (1H, m), 3.30 (1H, dd, J$_1$=6.8 Hz, J$_2$=2.7 Hz), 3.55 (1H, m), 4.27-4.35 (3H, m), 4.71-4.76 (1H, m), 4.84-4.89 (1H, m), 5.16-5.50 (6H, m), 5.94-6.04 (1H, m), 6.61 (1H, d, J=10.5 Hz), 7.15 (1H, d, J=10.5 Hz), 7.51 (2H, d, J=8.5 Hz), 8.22 (2H, d, J=8.8 Hz), 8.79 (1H, s)

b) (1R,5S,6S)-6-((1R)-1-Hydroxyethyl)-1-methyl-2-[[(Z)-2-(4-(N-4-nitrobenzyloxycarbonyl-L-valyloxymethyl)thiazol-5-yl)ethen-1-yl]thio]-1-carbapen-2-em-3-carboxylic acid Allyl (1R,5S,6S)-6-((1R)-1-hydroxyethyl)-1-methyl-2-[[(Z)-2-(4-(N-4-nitrobenzyloxycarbonyl-L-valinyloxymethyl)thiazol-5-yl)ethen-1-yl]thio]-1-carbapen-2-em-3-carboxylate (500 mg) and 250 mg of dimedone were dissolved in 10 ml of tetrahydrofuran. Tetrakistriphenylphosphine palladium (82 mg) was added to the solution, and the mixture was stirred under an argon atmosphere at room temperature for 30 min. The reaction mixture was poured into 50 ml of 20% brine and 50 ml of ethyl acetate, and the mixture was adjusted to pH 0.6 by the addition of a 1 N aqueous hydrochloric acid solution, followed by separation. The organic layer was dried over anhydrous magnesium sulfate, and the solid was removed by filtration, and the solvent was removed by distillation under the reduced pressure. The residue was purified by column chromatography on Sephadex LH-20 (dichloromethane: methanol=1:1) to give 317 mg of (1R,5S,6S)-6-((1R)-1-hydroxyethyl)-1-methyl-2-[[(Z)-2-(4-(N-4-nitrobenzyloxycarbonyl-L-valyloxymethyl)thiazol-5-yl)ethen-1-yl]thio]-1-carbapen-2-em-3-carboxylic acid.

NMR (CDCl$_3$) δ: 0.82-0.85 (6H, m), 1.03 (3H, d, J=7.3 Hz), 1.14 (3H, d, J=6.3 Hz), 1.99-2.04 (1H, m), 3.29 (1H, dd, J$_1$=6.2 Hz, J$_2$=2.8 Hz), 3.73 (1H, m), 3.92-3.98 (1H, m), 4.19 (1H, dd, J$_1$=10.0 Hz, J$_2$=2.7 Hz), 5.09 (1H, d, J=4.9 Hz), 5.19 (2H, s), 5.29 (1H, d, J=12.4 Hz), 5.40 (1H, d, J=12.4 Hz), 6.94 (1H, d, J=10.5 Hz), 7.21 (1H, d, J=10.5 Hz), 7.62 (2H, d, J=8.8 Hz), 7.87 (2H, d, J=8.3 Hz), 8.25 (2H, d, J=8.8 Hz), 8.32 (1H, s), 9.12 (1H, s)

c) (1R,5S,6S)-6-((1R)-1-Hydroxyethyl)-1-methyl-2-[[(Z)-2-(4-(L-valyloxymethyl)thiazol-5-yl)ethen-1-yl]thio]-1-carbapen-2-em-3-carboxylic acid In the same manner as in step c) in Example 41, 27 mg of (1R,5S,6S)-6-((1R)-1-hydroxyethyl)-1-methyl-2-[[(Z)-2-(4-(L-valyloxymethyl)thiazol-5-yl)ethen-1-yl]thio]-1-carbapen-2-em-3-carboxylic acid was prepared from 150 mg of (1R,5S,6S)-6-((1R)-1-hydroxyethyl)-1-methyl-2-[[(Z)-2-(4-(N-4-nitrobenzyloxy-carbonyl-L-valyloxymethyl)thiazol-5-yl)ethen-1-yl]thio]-1-carbapen-2-em-3-carboxylic acid.

NMR (CDCl$_3$) δ: 0.75 (3H, d, J=7.1 Hz), 0.77 (3H, d, J=7.1 Hz), 0.96 (3H, d, J=7.3 Hz), 1.14 (3H, d, J=6.3 Hz), 2.07-2.15 (1H, m), 3.29 (1H, dd, J$_1$=6.1 Hz, J$_2$=2.7 Hz), 3.44 (1H, m), 3.85 (1H, d, J=4.4 Hz), 4.06-4.12 (2H, m), 5.26 (1H, d, J=12.4 Hz), 5.42 (1H, d, J=12.7 Hz), 6.71 (1H, d, J=10.5 Hz), 7.00 (1H, d, J=10.5 Hz), 8.82 (1H, s)

Example 119

1-(t-Butoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 89 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 162 mg of 1-(t-butoxycarbonyloxy)ethyl iodide.

NMR (CDCl$_3$) δ: 1.1-1.2 (3H, m), 1.3-1.4 (3H, m), 1.49 (9H, s), 1.55-1.7 (3H, m), 2.0-2.1 (1H, m), 2.7-2.85 (1H, m), 3.27 (1H, dd, J$_1$=6.6 Hz, J$_2$=2.7 Hz), 3.5-3.6 (1H, m), 4.2-4.3 (2H, m), 4.85 (2H, s), 6.51 (1H, d, J=10.5 Hz), 6.8-6.9 (1H, m), 7.1-7.2 (1H, m), 8.78, 8.79 (total 1H, 2s)

Example 120

1-(t-Butoxycarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in Example 81, 89 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 162 mg of 1-(t-butoxycarbonyloxy)ethyl iodide.

NMR (CDCl$_3$) δ: 1.15-1.25 (3H, m), 1.3-1.4 (3H, m), 1.49 (9H, s), 1.55-1.7 (3H, m), 2.0-2.1 (1H, m), 2.7-2.85 (1H, m), 3.27 (1H, dd, J$_1$=6.6 Hz, J$_2$=2.7 Hz), 3.5-3.6 (1H, m), 4.2-4.3 (2H, m), 4.85 (2H, s), 6.51 (1H, d, J=10.5 Hz), 6.85-6.95 (1H, m), 7.05-7.15 (1H, m), 8.78, 8.79 (total 1H, 2s)

Example 121

Ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 143 mg of the title compound was prepared from 265 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 0.063 ml of ethyl iodide.

NMR (CDCl$_3$) δ: 1.20 (3H, d, J=7.3 Hz), 1.34-1.41 (6H, m), 1.80 (1H, d, J=4.6 Hz), 2.51 (1H, t, J=6.0 Hz), 3.29 (1H, dd, J$_1$=6.8 Hz, J$_2$=2.7 Hz), 3.48-3.59 (1H, m), 4.23-4.44 (4H, m), 4.85 (2H, d, J=6.0 Hz), 6.53 (1H, d, J=10.5 Hz), 7.10 (1H, d, J=10.5 Hz), 8.78 (1H, s)

Example 122

(5-Methyl-2-oxo-1,3-dioxolen-4-yl)methyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in Example 81, 156 mg of the title compound was prepared from 160 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 122 mg of (5-methyl-2-oxo-1,3-dioxolen-4-yl)methyl bromide.

NMR (DMSO-d$_6$) δ: 1.08 (3H, d, J=6.9 Hz), 1.14 (3H, d, J=6.3 Hz), 2.20 (3H, s), 3.25-3.35 (1H, m), 3.75-3.9 (1H, m), 3.9-4.05 (1H, m), 4.2-4.3 (1H, m), 4.67 (2H, d, J=5.4 Hz), 5.1-5.2 (3H, m), 5.25-5.35 (1H, m), 6.86 (1H, d, J=10.8 Hz), 7.33 (1H, d, J=10.8 Hz), 9.05 (1H, s)

Example 123

Phenyloxycarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 278 mg of the title compound was prepared from 226 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 243 mg of phenyloxycarbonyloxymethyl iodide.

NMR (CDCl$_3$) δ: 1.21 (3H, d, J=7.5 Hz), 1.34 (3H, d, J=6.3 Hz), 2.05-2.25 (1H, m), 2.7-2.9 (1H, m), 3.30 (1H, dd, J$_1$=6.6 Hz, J$_2$=2.4 Hz), 3.5-3.6 (1H, m), 4.2-4.35 (2H, m), 4.85 (2H, d, J=5.4 Hz), 5.98 (1H, d, J=5.7 Hz), 6.11 (1H, d, J=5.7 Hz), 6.51 (1H, d, J=10.5 Hz), 7.15 (1H, d, J=10.5 Hz), 7.2-7.35 (3H, m), 7.35-7.45 (2H, m), 8.72 (1H, s)

Example 124

N,N-Di(propan-1-yl)aminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in Example 81, 179 mg of the title compound was prepared from 159 mg of sodium (1R,5S,6S)-

6-((1R)-1-hydroxyethyl)-2-[[(Z)-2-(4-hydroxymethylthiazol-5-yl)ethen-1-yl]thio]-1-methyl-1-carbapen-2-em-3-carboxylate and 135 mg of N,N-di(propan-1-yl)aminocarbonyloxymethyl iodide.

NMR (CDCl₃) δ: 0.8-0.95 (6H, m), 1.19 (3H, d, J=7.5 Hz), 1.34 (3H, d, J=6.3 Hz), 1.45-1.6 (4H, m), 2.1-2.25 (1H, m), 2.6-2.8 (1H, m), 3.1-3.3 (5 H, m), 3.5-3.6 (1H, m), 4.2-4.3 (2H, m), 4.85 (2H, d, J=4.8 Hz), 5.92 (1H, d, J=5.7 Hz), 5.99 (1H, d, J=5.7 Hz), 6.50 (1H, d, J=10.5 Hz), 7.12 (1H, d, J=10.5 Hz), 8.77 (1H, s)

Example 125

(Cis-2,6-dimethylpiperidin-1-yl)carbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) (Cis-2,6-dimethylpiperidin-1-yl)carbonyloxymethyl chloride A solution (24 ml) of 2.39 ml of chloromethyl chloroformate in toluene was added dropwise to 46 ml of a solution of 9.11 ml of cis-2,6-dimethylpiperidine in toluene under ice cooling over a period of 10 min, and the mixture was stirred at room temperature for 16 hr. 1 N hydrochloric acid (60 ml) was added thereto, followed by separation. The organic layer was washed with 60 ml of a 5% aqueous sodium hydrogencarbonate solution and 60 ml of 20% brine, was dried over anhydrous magnesium sulfate, and was filtered, and the solvent was removed by distillation under the reduced pressure to give 12.7 g of (cis-2,6-dimethylpiperidin-1-yl)carbonyloxymethyl chloride.

NMR (CDCl₃) δ: 1.23 (6H, d, J=7.1 Hz), 1.46-1.81 (6H, m), 4.34 (2H, m), 5.83 (2H, s)

b) (Cis-2,6-dimethylpiperidin-1-yl)carbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate Sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (300 mg) was added to 5 ml of a solution of 183 mg of (cis-2,6-dimethylpiperidin-1-yl)carbonyloxymethyl chloride in DMSO, and the mixture was stirred at room temperature for 18 hr. Ethyl acetate (20 ml) and 20 ml of 20% brine were added thereto, followed by separation. The organic layer was washed twice with 20% brine, was dried over anhydrous magnesium sulfate, and was filtered, and ethyl acetate was removed by distillation under the reduced pressure. The residue was purified by column chromatography on silica gel (ethyl acetate:methanol=15:1) to give 273 mg of the title compound.

NMR (CDCl₃) δ: 1.19-1.22 (9H, m), 1.34 (3H, d, J=6.3 Hz), 1.44-1.76 (6H, m), 2.10 (1H, d, J=4.4 Hz), 2.63 (1H, t, J=6.0 Hz), 3.28 (1H, dd, J₁=2.8 Hz, J₂=6.7 Hz), 3.54 (1H, m), 4.25-4.35 (4H, m), 4.85 (2H, d, J=5.8 Hz), 5.94 (1H, d, J=5.6 Hz), 6.02 (1H, d, J=5.6 Hz), 6.51 (1H, d, J=10.5 Hz), 7.12 (1H, d, J=10.5 Hz), 8.78 (1H, s)

Example 126

N,N-Di-(butan-1-yl)aminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) Chloromethyl N,N-di-n-butylcarbamate Chloromethyl chloroformate (5.0 ml) was added dropwise to 100 ml of a solution of 11.7 ml of triethylamine and 11.3 ml of N,N-di-n-butylamine in cyclopentyl methyl ether under ice cooling, and the mixture was stirred at room temperature for 13 hr. 2 N hydrochloric acid (100 ml) was added thereto, followed by separation. The organic layer was washed with 100 ml of a 5% aqueous sodium hydrogencarbonate solution and 100 ml of semi-saturated brine, was dried over anhydrous magnesium sulfate, and was filtered, and the solvent was removed by distillation under the reduced pressure to give 12.7 g of chloromethyl N,N-di-n-butylcarbamate.

NMR (CDCl₃) δ: 0.92 (6H, t, J=7.3 Hz), 1.25-1.37 (4H, m), 1.47-1.58 (4H, m), 3.18-3.30 (4H, m), 5.79 (2H, m)

b) N,N-Di(butan-1-yl)aminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 220 mg of the title compound was prepared from 154 mg of chloromethyl N,N-di-n-butylcarbamate and 233 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl₃) δ: 0.86-0.94 (6H, m), 1.19 (3H, d, J=7.3 Hz), 1.23-1.36 (7H, m), 1.43-1.57 (4H, m), 1.98 (1H, d, J=4.6 Hz), 2.57 (1H, t, J=6.0 Hz), 3.14-3.31 (5H, m), 3.49-3.59 (1H, m), 4.21-4.30 (2H, m), 4.86 (2H, d, J=6.0 Hz), 5.92 (1H, d, J=5.6 Hz), 5.99 (1H, d, J=5.6 Hz), 6.51 (1H, d, J=10.2 Hz), 7.12 (1H, d, J=10.2 Hz), 8.77 (1H, s)

Example 127

Hexan-1-yl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in Example 81, 162 mg of the title compound was prepared from 218 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate and 0.095 ml of 1-iodohexane.

NMR (CDCl₃) δ: 0.86-0.91 (3H, m), 1.20 (3H, d, J=7.3 Hz), 1.24-1.37 (7H, m), 1.38-1.48 (2H, m), 1.70-1.79 (2H, m), 3.29 (1H, dd, J₁=6.6 Hz, J₂=2.6 Hz), 3.48-3.59 (1H, m), 4.19-4.39 (4H, m), 4.85 (1H, s), 6.53 (1H, d, J=10.2 Hz), 7.09 (1H, d, J=10.2 Hz), 8.77 (1H, s)

Example 128

N-(Hexan-1-yl)-N-methylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) Chloromethyl N-n-hexyl-N-methylcarbamate In the same manner as in step a) in Example 126, 4.64 g of chloromethyl N-n-hexyl-N-methylcarbamate was prepared from 3.17 g of N-n-hexyl-N-methylamine and 2.22 ml of chloromethyl chloroformate.

NMR (CDCl$_3$) δ: 0.86-0.94 (3H, m), 1.25-1.37 (6H, m), 1.47-1.60 (2H, m), 2.91, 2.94 (total 3H, s each), 3.65-3.81 (2H, m), 5.78, 5.80 (total 2H, s each)

b) N-(Hexan-1-yl)-N-methylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in step b) in Example 125, 206 mg of the title compound was prepared from 134 mg of chloromethyl N-n-hexyl-N-methylcarbamate and 217 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 0.83-0.91 (3H, m), 1.19 (3H, d, J=7.3 Hz), 1.22-1.31 (6H, m), 1.34 (3H, d, J=6.3 Hz), 1.45-1.56 (2H, m), 1.93-1.99 (1H, m), 2.56 (1H, t, J=5.9 Hz), 2.90, 2.91 (total 3H, each s), 3.20-3.31 (3H, m), 3.49-3.60 (2H, m), 4.21-4.30 (2H, m), 4.86 (2H, d, J=5.9 Hz), 5.90-5.94 (1H, m), 5.96-6.00 (1H, m), 6.51 (1H, d, J=10.2 Hz), 7.12 (1H, d, J=10.2 Hz), 8.78 (1H, s)

Example 129

N,N-Diisobutylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) Chloromethyl N,N-diisobutylcarbamate

In the same manner as in step a) in Example 126, 4.64 g of chloromethyl N,N-diisobutylcarbamate was prepared from 3.55 g of N,N-diisobutylamine and 2.22 ml of chloromethyl chloroformate.

NMR (CDCl$_3$) δ: 0.75-0.94 (12H, m), 1.87-2.05 (2H, m), 3.06 (1H, d, J=7.6 Hz), 3.12 (1H, d, J=7.6 Hz), 5.80 (2H, s)

b) N,N-diisobutylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 242 mg of the title compound was prepared from 159 mg of chloromethyl N,N-diisobutylcarbamate and 241 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 0.82-0.90 (12H, m), 1.19 (3H, d, J=7.3 Hz), 1.34 (3H, d, J=6.3 Hz), 1.85-2.02 (3H, m), 2.57-2.62 (1H, m), 3.00-3.17 (4H, m), 3.27 (1H, dd, J$_1$=6.8 Hz, J$_2$=2.7 Hz), 3.46-3.59 (1H, m), 4.19-4.30 (2H, m), 4.86 (2H, d, J=5.9 Hz), 5.93 (1H, d, J=5.5 Hz), 5.98 (1H, d, J=5.5 Hz), 6.51 (1H, d, J=10.2 Hz), 7.12 (1H, d, J=10.2 Hz), 8.78 (1H, s)

Example 130

N,N-Diisopropylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in step b) in Example 125, 150 mg of the title compound was prepared from 133 mg of chloromethyl N,N-diisopropylcarbamate and 231 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 1.18-1.23 (15H, m), 1.34 (3H, d, J=6.4 Hz), 1.99 (1H, d, J=4.4 Hz), 2.57 (1H, t, J=5.9 Hz), 3.27 (1H, dd, J$_1$=6.8 Hz, J$_2$=2.6 Hz), 3.48-3.59 (1H, m), 3.78 (1H, brs), 4.06 (1H, brs), 4.21-4.30 (2H, m), 4.86 (2H, d, J=5.9 Hz), 5.93 (1H, d, J=5.6 Hz), 5.98 (1H, d, J=5.6 Hz), 6.51 (1H, d, J=10.2 Hz), 7.12 (1H, d, J=10.2 Hz), 8.78 (1H, s)

Example 131

N-Cyclohexyl-N-methylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate a) Chloromethyl N-cyclohexyl-N-methylcarbamate

A solution (44 ml) of 4.39 ml of N-methylcyclo-N-hexylamine and 5.44 ml of triethylamine in toluene was added dropwise to 27 ml of a solution of 2.67 ml of chloromethyl chloroformate in toluene over a period of 5 min while cooling in an ice bath, and the mixture was stirred at room temperature for 17 hr. 1 N hydrochloric acid (60 ml) was added thereto, followed by separation. The organic layer was then washed with 60 ml of a 5% aqueous sodium hydrogencarbonate solution and 60 ml of 20% brine, was dried over anhydrous magnesium sulfate, and was filtered, and the solvent was removed by distillation under the reduced pressure to give 5.76 g of chloromethyl N-cyclohexyl-N-methylcarbamate.

NMR (CDCl$_3$) δ: 1.06-1.80 (10H, m), 2.79, 2.85 (total 3H, s each), 3.82, 4.00 (total 1H, m each), 5.80, 5.82 (total 2H, s each)

b) N-Cyclohexyl-N-methylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 165 mg of the title compound was prepared from 122 mg of chloromethyl N-cyclohexyl-N-methylcarbamate and 200 mg of sodium (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate.

NMR (CDCl$_3$) δ: 1.04-1.41 (6H, m), 1.20 (3H, d, J=7.3 Hz), 1.34 (3H, d, 16.3 Hz), 1.67 (2H, m), 1.78 (2H, m), 1.99 (1H, m), 2.56 (1H, m), 2.78, 2.82 (total 3H, s each), 3.28 (1H, dd, J$_1$=2.7 Hz, J$_2$=6.8 Hz), 3.54 (1H, m), 3.85, 3.98 (total 1H, m each), 4.25-4.28 (2H, m), 4.86 (2H, d, J=5.6 Hz), 5.92-6.01 (2H, m), 6.51 (1H, d, J=10.2 Hz), 7.12 (1H, d, J=10.2 Hz), 8.78 (1H, s)

Example 132

N-Pentan-1-ylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate a) Chloromethyl N-pentan-1-ylcarbamate

A solution of 3.84 ml of n-pentylamine and 5.02 ml of triethylamine in 38 ml of toluene was added dropwise to 24 ml of a solution of 2.39 ml of chloromethyl chloroformate in toluene while cooling in an ice bath over a period of 15 min, and the mixture was stirred at room temperature for 15 hr. 1 N hydrochloric acid (60 ml) was added thereto, followed by separation. The organic layer was washed with 60 ml of a 5% aqueous sodium hydrogencarbonate solution and 60 ml of 20% brine, was dried over anhydrous magnesium sulfate, and was filtered. The solvent was removed by distillation under the reduced pressure, and the residue was purified by column chromatography on silica gel (n-hexane:ethyl acetate=3:1) to give 3.31 g of chloromethyl N-pentan-1-ylcarbamate.

NMR (CDCl$_3$) δ: 0.89-0.92 (3H, m), 1.27-1.39 (4H, m), 1.49-1.60 (2H, m), 3.16-3.25 (2H, m), 4.86 (1H, m), 5.75 (2H, s)

b) N-Pentan-1-ylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 125 mg of the title compound was prepared from 160 mg of chloromethyl N-pentan-1-yl-N-methylcarbamate and 300 mg of sodium (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate.

NMR (CDCl$_3$) δ: 0.89 (3H, m), 1.19 (3H, d, J=7.3 Hz), 1.24-1.30 (4H, m), 1.34 (3H, d, J=6.1 Hz), 1.50 (2H, m), 2.62 (1H, m), 3.19 (2H, m), 3.28 (1H, dd, J$_1$=2.6 Hz, J$_2$=6.7 Hz), 3.55 (1H, m), 4.24-4.27 (2H, m), 4.85 (2H, m), 4.92 (1H, m), 5.88 (1H, d, J=5.9 Hz), 5.96 (1H, d, J=5.9 Hz), 6.51 (1H, d, J=10.5 Hz), 7.12 (1H, d, J=10.2 Hz), 8.78 (1H, s)

Example 133

N-Cyclohexyl-N-ethylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate a) Chloromethyl N-cyclohexyl-N-ethylcarbamate

In the same manner as in step a) in Example 125, 6.44 g of chloromethyl N-cyclohexyl-N-ethylcarbamate was prepared from 10 ml of N-ethyl-N-cyclohexylamine and 2.68 ml of chloromethyl chloroformate.

NMR (CDCl$_3$) δ: 1.04-1.82 (13H, m), 3.16-3.29 (2H, m), 3.74, 3.92 (total 1H, m each), 5.82 (2H, s)

b) N-Cyclohexyl-N-ethylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in step b) in Example 125, 285 mg of the title compound was prepared from 190 mg of chloromethyl N-cyclohexyl-N-ethylcarbamate and 300 mg of sodium (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate.

NMR (CDCl$_3$) δ: 1.05-1.42 (6H, m), 1.20 (3H, d, J=7.3 Hz), 1.34 (3H, d, J=6.3 Hz), 1.72-1.78 (4H, m), 1.96 (1H, m), 2.54 (1H, m), 3.15-3.29 (3H, m), 3.54 (1H, m), 3.76, 3.91 (total 1H, m), 4.24-4.27 (2H, m), 4.85 (2H, d, J=5.9 Hz), 5.93 (1H, d, J=5.6 Hz), 6.02 (1H, d, J=5.6 Hz), 6.51 (1H, d, J=10.2 Hz), 7.12 (1H, d, J=10.2 Hz), 8.77 (1H, s)

Example 134

N-Isobutyl-N-isopropylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate a) Chloromethyl N-isobutyl-N-isopropylcarbamate

Toluene (9 ml), 1.42 ml of N,N-diisopropylethylamine, and 0.56 ml of chloromethyl chloroformate were added in that order to 870 mg of N-isobutylisopropylamine, and the mixture was stirred at room temperature for 16 hr. 1 N hydrochloric acid (15 ml) was added thereto, followed by separation. The organic layer was washed with 15 ml of a 5% aqueous sodium hydrogencarbonate solution and 15 ml of 20% brine, was dried over anhydrous magnesium sulfate, and was filtered. The solvent was removed by distillation under the reduced pressure to give 1.23 g of chloromethyl N-isobutyl-N-isopropylcarbamate.

NMR (CDCl$_3$) δ: 0.90 (6H, d, J=6.6 Hz), 1.19-1.27 (6H, m), 1.86-2.00 (1H, m), 3.00, 3.07 (total 2H, d each, J=7.3 Hz), 3.94-3.99 (1H, m), 5.79, 5.82 (2H, each)

b) N-Isobutyl-N-isopropylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate In the same manner as in step b) in Example 125, 279 mg of the title compound was prepared from 177 mg of chloromethyl N-isobutyl-N-isopropylcarbamate and 300 mg of sodium (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate.

NMR (CDCl$_3$) δ: 0.85-0.89 (6H, m), 1.18-1.28 (9H, m), 1.34 (3H, d, J=6.3 Hz), 1.85-1.95 (2H, m), 2.55 (1H, t, J=6.0 Hz), 2.99-3.04 (2H, m), 3.27 (1H, dd, J$_1$=2.7 Hz, J$_2$=6.8 Hz), 3.54 (1H, m), 3.94-4.00 (1H, m), 4.23-4.26 (2H, m), 4.86 (2H, d, J=5.6 Hz), 5.91-6.03 (2H, m), 6.51 (1H, d, J=10.2 Hz), 7.12 (1H, d, J=10.2 Hz), 8.77 (1H, s)

Example 135

N-t-Butyl-N-ethylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate a) Chloromethyl N-t-butyl-N-ethylcarbamate

In the same manner as in step a) in Example 125, 5.54 g of chloromethyl N-t-butyl-N-ethylcarbamate was prepared from 9.15 ml of N-t-butylethylamine and 2.67 ml of chloromethyl chloroformate.

NMR (CDCl$_3$) δ: 1.14 (3H, t, J=6.9 Hz), 1.43 (9H, s), 3.40 (2H, q, J=7.1 Hz), 5.80 (2H, s)

b) N-t-Butyl-N-ethylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 273 mg of the title compound was prepared from 180 mg of chloromethyl N-t-butyl-N-ethylcarbamate and 300 mg of sodium (1R, 5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 1.11 (3H, t, J=7.1 Hz), 1.19 (3H, d, J=7.3 Hz), 1.34 (3H, d, J=6.3 Hz), 1.41 (9H, s), 2.06 (1H, m), 2.63 (1H, m), 3.27 (1H, dd, J$_1$=2.7 Hz, J$_2$=6.8 Hz), 3.39 (2H, q, J=7.0 Hz), 3.50-3.58 (1H, m), 4.24-4.27 (2H, m), 4.85 (2H, d, J=4.6 Hz), 5.91 (1H, d, J=5.6 Hz), 6.00 (1H, d, J=5.6 Hz), 6.51 (1H, d, J=10.2 Hz), 7.12 (1H, d, J=10.2 Hz), 8.77 (1H, s)

Example 136

1-(N,N-Diisopropylaminocarbonyloxy)ethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate (diastereomer mixture)

a) 1-Chloroethyl N,N-diisopropylcarbamate

In the same manner as in step a) in Example 125, 10.2 g of 1-chloroethyl N,N-diisopropylcarbamate was prepared from 15.4 ml of N,N-diisopropylamine and 5.40 ml of 1-chloroethyl chloroformate.

NMR (CDCl$_3$) δ: 1.23 (12H, d, J=6.8 Hz), 1.83 (3H, d, J=5.9 Hz), 3.76 (1H, m), 4.11 (1H, m), 6.65 (1H, q, J=5.8 Hz)

b) 1-(N,N-Diisopropylaminocarbonyloxy)ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 92 mg of the title compound was prepared from 247 mg of 1-chloroethyl N,N-diisopropylcarbamate and 400 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 1.16-1.22 (15H, m), 1.32-1.35 (3H, m), 1.60-1.64 (3H, m), 1.86 (1H, m), 2.55 (1H, m), 3.25-3.29 (1H, m), 3.48-3.56 (1H, m), 3.75 (1H, m), 4.08 (1H, m), 4.22-4.26 (2H, m), 4.84, 4.86 (total 2H, s each), 6.50-6.53 (1H, m), 7.00-7.11 (2H, m), 8.76, 8.77 (total 1H, s each)

Example 137

1-[(Cis-2,6-dimethylpiperidin-1-yl)carbonyloxy] ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

a) 1-[(Cis-2,6-dimethylpiperidin-1-yl)carbonyloxy] ethyl chloride

In the same manner as in step a) in Example 125, 6.01 g of 1-[(cis-2,6-dimethylpiperidin-1-yl)carbonyloxy]ethyl chloride was prepared from 8.45 g of cis-2,6-dimethylpiperidine and 3.66 ml of 1-chloroethyl chloroformate.

NMR (CDCl$_3$) δ: 1.21-1.29 (6H, m), 1.45-1.86 (9H, m), 4.28-4.38 (2H, m), 6.60-6.68 (1H, m)

b) 1-[(Cis-2,6-dimethylpiperidin-1-yl)carbonyloxy] ethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate (diastereomer mixture)

In the same manner as in step b) in Example 125, 98 mg of the title compound was prepared from 283 mg of 1-[(cis-2,6-dimethylpiperidin-1-yl)carbonyloxy]ethyl chloride and 404 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 1.15-1.27 (9H, m), 1.31-1.37 (3H, m), 1.40-1.81 (9H, m), 1.92 (1H, brs), 2.59 (1H, brs), 3.25-3.30 (1H, m), 3.47-3.58 (1H, m), 4.18-4.39 (4H, m), 4.82-4.87 (2H, m), 6.51 (1H, d, J=10.5 Hz), 6.97-7.13 (2H, m), 8.78 (1H, m)

Example 138

N-Ethyl-N-isoamylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate a) Chloromethyl N-ethyl-N-isoamylcarbamate In the same manner as in step a) in Example 125, 207 mg of chloromethyl N-ethyl-N-isoamylcarbamate was prepared from 228 mg of N-ethyl-N-isoamylamine and 0.089 ml of chloromethyl chloroformate.

NMR (CDCl$_3$) δ: 0.93 (6H, d, J=6.4 Hz), 1.10-1.19 (3H, m), 1.44-1.49 (2H, m), 1.55-1.62 (1H, m), 3.18-3.38 (4H, m), 5.80 (2H, s)

b) N-Ethyl-N-isoamylaminocarbonyloxymethyl (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate In the same manner as in step b) in Example 125, 213 mg of the title compound was prepared from 202 mg of chloromethyl N-ethyl-N-isoamylcarbamate and 328 mg of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate.

NMR (CDCl$_3$) δ: 0.83-0.94 (6H, m), 1.07-1.13 (3H, m), 1.19 (3H, d, J=7.2 Hz), 1.23-1.42 (3H, m), 1.34 (3H, d, J=6.4 Hz), 1.87-1.95 (1H, m), 2.48 (1H, t, J=5.9 Hz), 3.19-3.34 (5H, m), 3.48-3.59 (1H, m), 4.21-4.30 (2H, m), 4.86 (2H, d, J=5.6 Hz), 5.90-5.94 (1H, m), 5.97-6.02 (1H, m), 6.51 (1H, d, J=10.2 Hz), 7.12 (1H, d, J=10.2 Hz), 8.77 (1H, s)

Example 139

(5-Bromothiazol-4-yl)-methanol

Calcium chloride dihydrate (29.4 g), 11.80 g of ethyl 5-bromothiazole-4-carboxylate, and 30 ml of THF were added in that order to 60 ml of water, and the mixture was stirred. The temperature of the reaction solution was regulated to 0 to 2° C., and 3.78 g of sodium borohydride was introduced into the reaction solution at a reaction solution temperature of 5° C. or below. The reaction solution was stirred at a reaction solution temperature of 2 to 7° C. for 2 hr. Thereafter, 22 ml of acetone and 20 ml of 5 N hydrochloric acid were introduced in that order into the reaction solution at a reaction solution temperature of 7° C. or below. The mixture was stirred at the same temperature for 30 min and was adjusted to pH 5 by the addition of a 5 N aqueous sodium hydroxide solution. The reaction mixture was extracted with 120 ml of ethyl acetate. The separated aqueous layer was extracted with 120 ml of ethyl acetate. The organic layers were then combined, were washed with 60 ml of 5% sodium bicarbonate water, 30 ml of 5% sodium bicarbonate water, and 30 ml of 20% brine in that order. The aqueous layers were combined and were extracted with 120 ml of ethyl acetate. The organic layers were combined, were dried over anhydrous magnesium sulfate, and were filtered, and the solvent was removed by distillation to separate the solid and thus to give 7.64 g of (5-bromothiazol-4-yl)-methanol.

NMR (CDCl$_3$) δ: 2.73 (1H, t, J=6.3 Hz), 4.76 (2H, d, J=6.3 Hz), 8.78 (1H, s)

Example 140

[5-[2-(Trimethylsilyl)ethynyl]thiazol-4-yl]-methanol (5-Bromothiazol-4-yl)-methanol (6.15 g), 8.9 ml of triethylamine, 61 mg of copper(I) iodide, 5.4 ml of trimethylsilylacetylene, and 223 mg of bis(triphenylphosphine) palladium(II) dichloride were added in that order to 25 ml of DMF, the mixture was stirred, and the air in the system was replaced by argon. The reaction mixture was stirred with heating at 90° C. for 90 min and was then allowed to stand for cooling. Toluene (74 ml) and 25 ml of water were added to the reaction mixture, and the aqueous layer was separated. Water (25 ml) was added to the organic layer, and the mixture was adjusted to pH 2 by the addition of 5 N hydrochloric acid, followed by separation of the aqueous layer. The organic layer was washed with 25 ml of 5% sodium bicarbonate water and 25 ml of 10% brine in that order and was then treated with 1.4 g of activated carbon and anhydrous magnesium sulfate. The solvent was removed by distillation, and the solid was separated to give 5.35 g of [5-[2-(trimethylsilyl)ethynyl]thiazol-4-yl]-methanol.

NMR (CDCl$_3$) δ: 0.26 (9H, s), 2.75 (1H, t, J=6.3 Hz), 4.83 (2H, d, J=6.3 Hz), 8.64 (1H, s)

Example 141

5-Ethynyl-4-hydroxymethylthiazole

Potassium carbonate (39 mg) was added to a solution of 6.02 g of [5-[2-(trimethylsilyl)ethynyl]thiazol-4-yl]-methanol in 12 ml of methanol, and the mixture was stirred at room temperature for 10 min. A 10% aqueous citric acid solution (6 ml) was added thereto, and the mixture was stirred for 30 min. The reaction mixture was then extracted with 90 ml of ethyl acetate. The organic layer was washed with 12 ml of 5% sodium bicarbonate water and 12 ml of 20% brine in that order and was treated with 0.8 g of activated carbon and anhydrous magnesium sulfate. Toluene (15 ml) was added to the organic layer, the mixture was concentrated, and the precipitated solid was collected by filtration to give 3.11 g of 5-ethynyl-4-hydroxymethylthiazole.

NMR (CDCl$_3$) δ: 3.48 (1H, t, J=6.32 Hz), 3.60 (1H, s), 4.85 (2H, d, J=6.32 Hz), 8.69 (1H, s)

Example 142

N,N-Diisopropylaminocarbonyloxymethyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate Chloromethyl N,N-diisopropylcarbamate (2.81 g) and 2.76 g of triethyl benzyl ammonium chloride were added to 50 ml of a solution of 4.89 g of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate in N,N-dimethylacetamide, and the mixture was stirred at 30° C. for 5 hr. The reaction solution was washed twice with 180 ml of heptane. Thereafter, 125 ml of ethyl acetate and 125 ml of 20% brine were added thereto, followed by separation. The organic layer was washed three times with 125 ml of 10% brine, was dried over anhydrous magnesium sulfate, and was filtered, and ethyl acetate was removed by distillation under the reduced pressure to give 6.01 g of the title compound.

Example 143

Sodium (5R,6S)-6-((1R)-1-hydroxyethyl)-2-[[(Z)-2-(4-hydroxymethylthiazol-5-yl)ethen-1-yl]thio]-1-carbapen-2-em-3-carboxylate a) 4-Nitrobenzyl (5R,6S)-6-((1R)-1-hydroxyethyl)-2-[[(Z)-2-(4-hydroxymethylthiazol-5-yl)ethen-1-yl]thio]-1-carbapen-2-em-3-carboxylate 4-Nitrobenzyl (5R,6S)-6-((1R)-1-hydroxyethyl)-2-[[(Z)-2-(4-hydroxymethylthiazol-5-yl)ethen-1-yl]thio]-1-carbapen-2-em-3-carboxylate (2.76 g) was prepared in substantially the same manner as in step b) in Example 41, except that 4.13 g of 4-nitrobenzyl (5R,6S)-2-(diphenylphosphoryloxy)-6-((1R)-1-hydroxyethyl)-1-carbapen-2-em-3-carboxylate was used instead of 4-nitrobenzyl (1R,5R,6S)-2-(diphenylphosphoryloxy)-6-((1R)-1-hydroxyethyl)-1-methyl-1-carbapen-2-em-3-carboxylate.

NMR (DMSO-d$_6$) δ: 1.14 (3H, d, J=6.4 Hz), 3.30-3.39 (1H, m), 3.41-3.54 (2H, m), 3.93-4.03 (1H, m), 4.18-4.27 (1H, m), 4.66 (2H, d, J=5.8 Hz), 5.13 (1H, d, J=5.1 Hz), 5.31 (1H, t, J=5.8 Hz), 5.36 (1H, d, J=13.8 Hz), 5.50 (1H, d, J=13.8 Hz), 6.83 (1H, d, J=10.5 Hz), 7.27 (1H, d, J=10.5 Hz), 7.75 (2H, d, J=8.7 Hz), 8.26 (2H, d, J=8.7 Hz), 9.03 (1H, s)

b) Sodium (5R,6S)-6-((1R)-1-hydroxyethyl)-2-[[(Z)-2-(4-hydroxymethylthiazol-5-yl)ethen-1-yl]thio]-1-carbapen-2-em-3-carboxylate In the same manner as in step c) in Example 41, 259 mg of the title compound was prepared from 1.10 g of 4-nitrobenzyl (5R,6S)-6-((1R)-1-hydroxyethyl)-2-[[(Z)-2-(4-hydroxymethyl-thiazol-5-yl)ethen-1-yl]thio]-1-carbapen-2-em-3-carboxy late.

NMR (DMSO-d$_6$) δ: 1.13 (3H, d, J=6.3 Hz), 2.95-3.04 (1H, m), 3.12-3.24 (2H, m), 3.84-3.95 (1H, m), 3.97-4.06 (1H, m), 4.63 (2H, d, J=5.8 Hz), 5.02 (1H, d, J=4.8 Hz), 5.23 (1H, t, J=5.8 Hz), 6.79 (1H, d, J=10.0 Hz), 6.99 (1H, d, J=10.0 Hz), 9.00 (1H, s)

Example 144

N,N-Diisopropylaminocarbonyloxymethyl (5R,6S)-6-((1R)-1-hydroxyethyl)-2-[[(Z)-2-(4-hydroxymethylthiazol-5-yl)ethen-1-yl]thio]-1-carbapen-2-em-3-carboxylate Chloromethyl N,N-diisopropylcarbamate (54 mg) and 75 mg of n-tetrabutyl ammonium bromide were added to 2 ml of a solution of 100 mg of sodium (5R,6S)-6-((1R)-1-hydroxyethyl)-2-[[(Z)-2-(4-hydroxymethylthiazol-5-yl)ethen-1-yl]thio]-1-carbapen-2-em-3-carboxylate in N,N-dimethylacetamide, and the mixture was stirred at 30° C. for 3.5 hr. Ethyl acetate (10 ml) and 10 ml of semi-saturated brine were added to the reaction solution, followed by separation. The organic layer was washed three times with 10 ml of semi-saturated brine, was dried over anhydrous magnesium sulfate, and was filtered. Ethyl acetate was removed by distillation under the reduced pressure, and the residue was purified by column chromatography on silica gel (ethyl acetate:methanol=15:1) to give 108 mg of the title compound.

NMR (CDCl$_3$) δ: 1.22 (12H, d, J=6.8 Hz), 1.33 (3H, d, J=6.3 Hz), 3.07-3.22 (2H, m), 3.30-3.40 (1H, m), 3.79 (1H, brs), 4.07 (1H, brs), 4.19-4.30 (2H, m), 4.84 (2H, s), 5.94 (1H, d, J=5.6 Hz), 6.02 (1H, d, J=5.6 Hz), 6.50 (1H, d, J=10.3 Hz), 7.08 (1H, d, J=10.3 Hz), 8.77 (1H, s)

Example 145

(1R,5S,6S)-6-((1R)-1-Hydroxyethyl)-2-[[(Z)-2-(4-hydroxymethylthiazol-5-yl)ethen-1-yl]thio]-1-methyl-1-carbapen-2-em-3-carboxylic acid 1 N Hydrochloric acid (7.10 ml) was added to 120 ml of an aqueous solution of 2.73 g of sodium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate at room temperature, and the mixture was stirred for 3 min. The reaction mixture was extracted twice with 150 ml of ethyl acetate. The extract was dried over anhydrous magnesium sulfate and was filtered, and ethyl acetate was removed by distillation under the reduced pressure until the amount of ethyl acetate was reduced to 50 ml. Hexane (200 ml) was added, and the precipitated solid was collected by filtration to give 1.63 g of the title compound.

NMR (DMSO-d$_6$) δ: 1.16 (3H, d, J=7.3 Hz), 1.14 (3H, d, J=6.3 Hz), 3.28 (1H, dd, J$_1$=6.2 Hz, J$_2$=2.8 Hz), 3.69-3.80 (1H, m), 3.93-4.01 (1H, m), 4.19 (1H, dd, J$_1$=10.0 Hz, J$_2$=2.7 Hz), 4.66 (2H, s), 5.09 (1H, brs), 5.32 (1H, brs), 6.84 (1H, d, J=10.7 Hz), 7.29 (1H, d, J=10.7 Hz), 9.05 (1H, s)

Example 146

Potassium (1R,5S,6S)-6-((1R)-1-hydroxyethyl)-2-[[(Z)-2-(4-hydroxymethylthiazol-5-yl)ethen-1-yl]thio]-1-methyl-1-carbapen-2-em-3-carboxylate A 10% Pd—C catalyst (hydrous, water content 53%) (500 mg) was added to a mixed solution of 1.00 g of 4-nitrobenzyl (1R,5S,6S)-6-((1R)-1-hydroxyethyl)-2-[[(Z)-2-(4-hydroxymethyl-thiazol-5-yl)ethen-1-yl]thio]-1-methyl-1-carbapen-2-em-3-carboxylate in 2.5 ml of water and 7.5 ml of THF, and the mixture was stirred under a hydrogen atmosphere while maintaining the temperature in a range of 30° C. to 35° C. for 3 hr. The catalyst was filtered, and 1.7 ml of a 1 M aqueous potassium hydrogencarbonate solution and 0.061 ml of 2-ethyl hexanoate were added to the filtrate. The mixture was washed with 80 ml of ethyl acetate, and the aqueous layer was concentrated to about 10 ml. The precipitated insolubles were removed by filtration, and the filtrate was further concentrated to about 8 ml. Acetone (60 ml) was added thereto, and the mixture was stirred under ice cooling for one hr. The precipitated solid was collected by filtration to give 432 mg of the title compound.

NMR (DMSO-d$_6$) δ: 0.96 (3H, d, J=7.3 Hz), 1.14 (3H, d, J=6.4 Hz), 3.06 (1H, dd, J$_1$=6.8 Hz, J$_2$=2.7 Hz), 3.37-3.48 (1H, m), 3.86-3.94 (1H, m), 4.01 (1H, dd, J$_1$=9.6 Hz, J$_2$=2.7 Hz), 4.63 (2H, d, J=5.4 Hz), 5.00 (1H, d, J=5.1 Hz), 5.24 (1H, t, J=5.4 Hz), 6.78 (1H, d, J=10.7 Hz), 7.02 (1H, d, J=10.7 Hz), 8.99 (1H, s)

Example 147

N,N-Diisopropylaminocarbonyloxymethyl (1R,5S,6S)-6-((1R)-1-hydroxyethyl)-2-[[(E)-2-(4-hydroxymethylthiazol-5-yl)ethen-1-yl]thio]-1-methyl-1-carbapen-2-em-3-carboxylate In the same manner as in Example 144, 90.9 mg of the title compound was prepared from 50.4 mg of chloromethyl N,N-diisopropylcarbamate and 87.8 mg of sodium (1R,5S,6S)-6-((1R)-1-hydroxyethyl)-2-[[(E)-2-(4-hydroxymethylthiazol-5-yl)ethen-1-yl]thio]-1-methyl-1-carbapen-2-em-3-carboxylate.

NMR (CDCl$_3$) δ: 1.14-1.26 (15H, m), 1.34 (3H, d, J=6.4 Hz), 3.27 (1H, dd, J$_1$=7.0 Hz, J$_2$=2.6 Hz), 3.49-3.57 (1H, m), 3.79 (1H, brs), 4.07 (1H, brs), 4.21-4.29 (2H, m), 4.81 (2H, s), 5.90 (1H, d, J=5.6 Hz), 6.00 (1H, d, J=5.6 Hz), 6.74 (1H, d, J=15.2 Hz), 7.12 (1H, d, J=15.2 Hz), 8.64 (1H, s)

The compounds prepared in the Examples are shown in Tables 1 to 10.

In the tables, Me represents methyl, Et represents ethyl, iPr represents isopropyl, nPr represents n-propyl, nBu represents n-butyl, tBu represents tert-butyl, Tr represents trityl(triphenylmethyl), TMS represents trimethylsilyl, and E/Z represents the conformation at the thioethenyl site.

TABLE 1

| Example | Structure |
| --- | --- |
| 1 | TrS—CH=CH—(thiazole)-CH$_2$OH |
| 2 | TrS—CH=CH—(thiazole)-CH$_2$-O-CH$_2$CH$_2$OH |
| 3 | TrS—CH=CH—(thiazole)-C(O)N(CH$_3$)$_2$ |
| 4 | TrS—CH=CH—(thiazole)-CH$_2$OH |
| 5 | TrS—CH=CH—(4-methylthiazole) |
| 6 | TrS—CH=CH—(thiazole)-C(O)NH$_2$ |
| 7 | TrS—CH=CH—(thiazole)-C(O)NHCH$_3$ |

TABLE 1-continued

| Example | Structure |
|---|---|
| 8 | TrS-CH=CH-[thiazole]-C(=O)-N(Me)-CH2-CN |
| 9 | TrS-CH=CH-[thiazole]-C(=O)-NH-CH2-CN |
| 10 | TrS-CH=CH-[thiazole]-C(=O)-NH-CH2CH2-CN |
| 11 | TrS-CH=CH-[thiazole]-CH2-CN |
| 12 | TrS-CH=CH-[thiazole]-CH2-O-CH2CH2-OMe |
| 13 | TrS-CH=CH-[thiazole]-C(=O)-N(azetidine-3-CN) |
| 14 | TrS-CH=CH-[thiazole]-C(=O)-NH-CH2CH2-OH |
| 15 | TrS-CH=CH-[thiazole]-C(=O)-NH-CH2CH2CH2-OH |

TABLE 1-continued

| Example | Structure |
|---|---|
| 16 | TrS-CH=CH-[thiazole]-C(=O)-N(Me)-CH2CH2-OH |
| 17 | TrS-CH=CH-[thiazole]-C(=O)-N(azetidine) |
| 18 | TrS-CH=CH-[thiazole]-C(=O)-N(azetidine-3-OH) |
| 19 | TrS-CH=CH-[thiazole]-CH2-O-CH2CH2CH2-OH |
| 20 | TrS-CH=CH-[2-amino-thiazole]-C(=O)-NH2 |

TABLE 2

| Example | Structure |
|---|---|
| 21 | TrS-CH=CH-[thiazole]-CH2-OH |
| 22 | TrS-CH=CH-[thiazole-2-CONH2] |

TABLE 2-continued

| Example | Structure |
|---|---|
| 23 | TrS–CH=CH–[5-thiazolyl, 2-NH2] |
| 24 | TrS–CH=CH–[thiazol-5-yl, 2-C(O)N(CH3)2] |
| 25 | TrS–CH=CH–[2-thiazolyl, 4-CONH2] |
| 26 | TrS–CH=CH–[2-thiazolyl, 4-C(O)NH-CH2CH2OH] |
| 27 | TrS–CH=CH–[2-thiazolyl, 4-C(O)N(CH3)2] |
| 28 | TrS–CH=CH–[2-thiazolyl, 4-C(O)NHCH3] |
| 29 | TrS–CH=CH–[2-thiazolyl, 4-C(O)NH-CH2CN] |
| 30 | TrS–CH=CH–[2-thiazolyl, 4-C(O)N(CH3)-CH2CN] |
| 31 | TrS–CH=CH–[2-thiazolyl, 4-CH2CN] |
| 32 | TrS–CH=CH–[2-thiazolyl, 4-C(O)-N(azetidin-3-ol)] |
| 33 | TrS–CH=CH–[2-thiazolyl, 4-C(O)-N(3-cyanoazetidin-1-yl)] |
| 34 | TrS–CH=CH–[2-thiazolyl, 5-CH2OH] |
| 35 | TrS–CH=CH–[2-thiazolyl, 4-CONH2, 5-CONH2] |
| 36 | TrS–CH=CH–[4-thiazolyl] |
| 37 | TrS–CH=CH–[4-thiazolyl, 2-CONH2] |
| 38 | TrS–CH=CH–[4-thiazolyl, 5-CH2OH] |
| 39 | TMS–C≡C–[thiazol-5-yl, 4-CO2Et] |
| 40 | HC≡C–[thiazol-5-yl, 4-CO2Et] |

TABLE 3

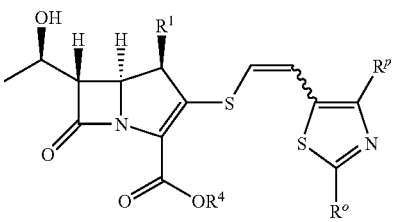

| Example | R¹ | E/Z | R° | R^p | R⁴ |
| --- | --- | --- | --- | --- | --- |
| 41 | CH₃ | Z | H | CH₂OH | Na |
| 42 | CH₃ | Z | H | CH₂O(CH₂)₂OH | Na |
| 43 | CH₃ | Z | H | CON(CH₃)₂ | Na |
| 45 | CH₃ | Z | H | CH₃ | Na |
| 46 | CH₃ | Z | H | CONH₂ | Na |
| 47 | CH₃ | Z | H | CONHCH₃ | Na |
| 48 | CH₃ | Z | H | CON(CH₃)CH₂CN | Na |
| 49 | CH₃ | Z | H | CONHCH₂CN | Na |
| 50 | CH₃ | Z | H | CONH(CH₂)₂CN | Na |
| 51 | CH₃ | Z | H | CH₂CN | Na |
| 52 | CH₃ | Z | H | CH₂O(CH₂)₂OCH₃ | Na |
| 53 | CH₃ | Z | H | 1-acetylazetidin-3-yl-CN | Na |
| 54 | CH₃ | Z | H | CONH(CH₂)₂OH | Na |
| 55 | CH₃ | Z | H | CONH(CH₂)₃OH | Na |
| 56 | CH₃ | Z | H | CON(CH₃)CH₂CH₂OH | Na |

TABLE 3-continued

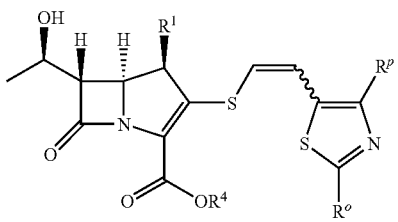

| Example | R¹ | E/Z | R° | R^p | R⁴ |
| --- | --- | --- | --- | --- | --- |
| 57 | CH₃ | Z | H | 1-acetylazetidine | Na |
| 58 | CH₃ | Z | H | 1-acetyl-3-hydroxyazetidine | Na |
| 59 | CH₃ | Z | H | CH₂O(CH₂)₃OH | Na |
| 60 | CH₃ | Z | NH₂ | CONH₂ | Na |
| 61 | CH₃ | E | H | CH₂OH | Na |
| 62 | CH₃ | Z | CONH₂ | H | Na |
| 63 | CH₃ | Z | NH₂ | H | Na |
| 64 | CH₃ | Z | CON(CH₃)₂ | H | Na |
| 79 | CH₃ | Z | H | CH₂OCOCH₃ | Na |
| 80 | CH₃ | Z | H | CH₂O(CH₂)₂OCOCH₃ | Na |

TABLE 4

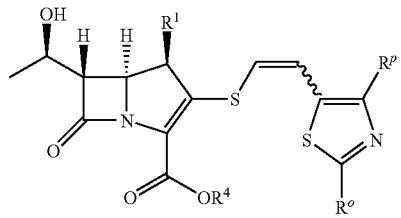

| Example | R¹ | E/Z | R° | R^p | R⁴ |
| --- | --- | --- | --- | --- | --- |
| 81 | CH₃ | Z | H | CH₂O(CH₂)₂OH | 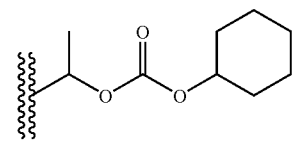 |
| 82 | CH₃ | Z | H | CON(CH₃)₂ | 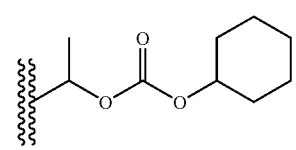 |
| 84 | CH₃ | Z | H | CONH₂ | 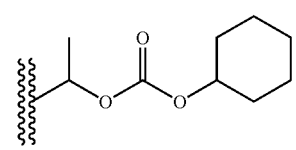 |

TABLE 4-continued

| Example | R¹ | E/Z | Rᵒ | Rᵖ | R⁴ |
|---|---|---|---|---|---|
| 85 | CH₃ | Z | H | CONHCH₂CN | cyclohexyl carbonate (sec) |
| 86 | CH₃ | Z | H | CONH(CH₂)₂OH | cyclohexyl carbonate (sec) |
| 87 | CH₃ | Z | CONH₂ | H | CH₂OCOtBu |
| 89 | CH₃ | Z | H | CH₂OH | cyclohexyl carbonate (sec) |
| 90 | CH₃ | Z | H | CH₂OH | CH₂OCOCH₃ |
| 91 | CH₃ | Z | H | CH₂OH | C(CH₃)OCOOiPr |
| 92 | CH₃ | Z | H | CH₂OH | C(CH₃)OCOOEt |
| 93 | CH₃ | Z | H | CH₂OH | CH₂OCOtBu |
| 94 | CH₃ | Z | H | CH₂OH | cyclohexyl carbonate (CH₂) |
| 95 | CH₃ | Z | H | CH₂OH | isobutyl carbonate (sec) |
| 96 | CH₃ | Z | H | CH₂OH | cyclohexyl carbonate (iPr-CH) |
| 97 | CH₃ | Z | H | CH₂OH | isobutyl carbonate (CH₂) |
| 98 | CH₃ | Z | H | CH₂OH | isopropyl carbonate (CH₂) |

TABLE 4-continued

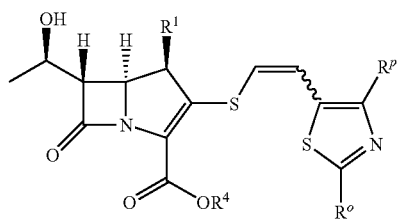

| Example | R¹ | E/Z | R° | Rᵖ | R⁴ |
|---|---|---|---|---|---|
| 99 | CH₃ | Z | H | CH₂OH | ![](isobutyrate ester) |
| 100 | CH₃ | Z | H | CH₂OH | ![](pentyl carbonate) |

TABLE 5

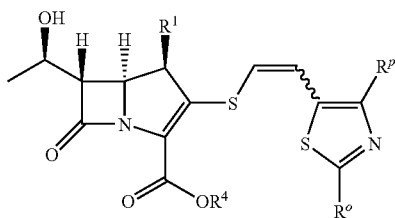

| Example | R¹ | E/Z | R° | Rᵖ | R⁴ |
|---|---|---|---|---|---|
| 101 | CH₃ | Z | H | CH₂OH | CH₂OCOOnBu |
| 102 | CH₃ | Z | H | CH₂OH | ![](3-pentyl carbonate) |
| 103 | CH₃ | Z | H | CH₂OH | ![](isopentyl carbonate) |
| 104 | CH₃ | Z | H | CH₂OH | CH₂OCOOnPr |
| 105 | CH₃ | Z | H | CH₂OCOCH₃ | ![](cyclohexyl carbonate) |
| 106 | CH₃ | Z | H | CH₂OH | CH₂OCOOEt |
| 107 | CH₃ | Z | H | CH₂OH | ![](neopentyl carbonate) |
| 108 | CH₃ | Z | H | CH₂OH | CH₂OCOOCH₃ |

TABLE 5-continued

| Example | R¹ | E/Z | R⁰ | Rᵖ | R⁴ |
|---|---|---|---|---|---|
| 109 | CH₃ | Z | H | CH₂OH | cyclopentyl carbonate CH₂ group |
| 110 | CH₃ | Z | H | CH₂OH | CH₂OCOOtBu |
| 111 | CH₃ | Z | H | CH₂OH | phthalide |
| 112 | CH₃ | Z | H | CH₂OH | CH(CH₃)OCOOCH₃ |
| 113 | CH₃ | Z | H | CH₂OH | 1-(cyclopentyloxycarbonyloxy)ethyl |
| 114 | CH₃ | Z | H | CH₂OH | (tetrahydropyran-4-yloxycarbonyloxy)methyl |
| 115 | CH₃ | Z | H | CH₂OH | 1-(neopentyloxycarbonyloxy)ethyl |
| 116 | CH₃ | Z | H | CH₂OH | (piperidin-1-ylcarbonyloxy)methyl |
| 117 | CH₃ | Z | H | CH₂OH | CH₂CH=CH₂ |
| 118 | CH₃ | Z | H | CH₂-O-C(=O)-CH(NH₂)-CH(CH₃)₂ (valine ester) | H |
| 119 | CH₃ | Z | H | CH₂OH | CH(CH₃)OCOOtBu |

TABLE 6

| Example | R¹ | E/Z | Rᵒ | Rᵖ | R⁴ |
|---------|-----|-----|-----|--------|-----|
| 120 | CH₃ | Z | H | CH₂OH | *tert-butyl carbonate of sec-alkyl* |
| 121 | CH₃ | Z | H | CH₂OH | Et |
| 122 | CH₃ | Z | H | CH₂OH | (5-methyl-2-oxo-1,3-dioxol-4-yl)methyl |
| 123 | CH₃ | Z | H | CH₂OH | phenyl carbonate methyl |
| 124 | CH₃ | Z | H | CH₂OCOCH₃ | N,N-dipropylcarbamoyloxymethyl |
| 125 | CH₃ | Z | H | CH₂OH | (2,6-dimethylpiperidine-1-carbonyloxy)methyl |
| 126 | CH₃ | Z | H | CH₂OH | N,N-dibutylcarbamoyloxymethyl |
| 127 | CH₃ | Z | H | CH₂OH | n-heptyl |
| 128 | CH₃ | Z | H | CH₂OH | N-hexyl-N-methylcarbamoyloxymethyl |

TABLE 6-continued
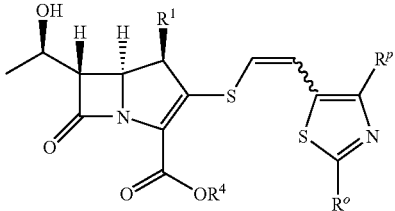
| Example | R¹ | E/Z | Rᵒ | Rᵖ | R⁴ |
|---|---|---|---|---|---|
| 129 | CH₃ | Z | H | CH₂OH | 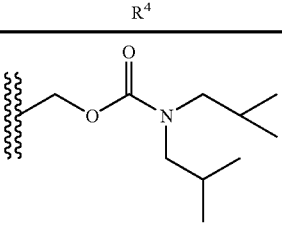 |
| 130 | CH₃ | Z | H | CH₂OH | 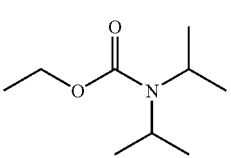 |
| 131 | CH₃ | Z | H | CH₂OH | 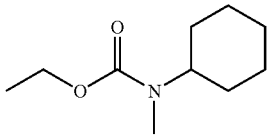 |
| 132 | CH₃ | Z | H | CH₂OH | 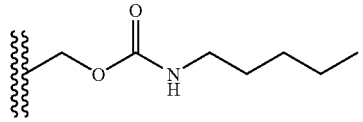 |
| 133 | CH₃ | Z | H | CH₂OH | 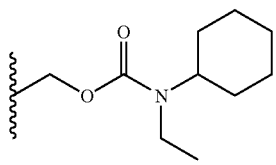 [SMILES: *COC(=O)N(CC)C1CCCCC1] |
TABLE 7
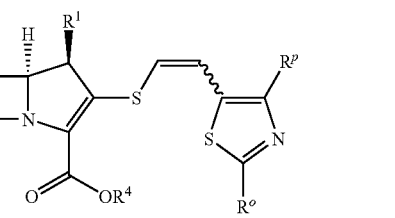
| Example | R¹ | E/Z | Rᵒ | Rᵖ | R⁴ |
|---|---|---|---|---|---|
| 134 | CH₃ | Z | H | CH₂OH | 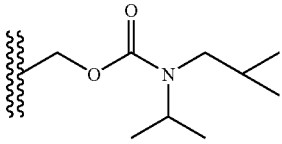 |
| 135 | CH₃ | Z | H | CH₂OH | 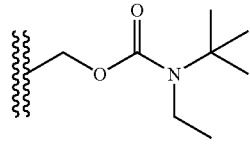 |

TABLE 7-continued

| Example | R¹ | E/Z | R° | R^p | R⁴ |
|---|---|---|---|---|---|
| 136 | CH₃ | Z | H | CH₂OH | 1-(N,N-diisopropylcarbamoyloxy)ethyl |
| 137 | CH₃ | Z | H | CH₂OH | 1-(2,6-dimethylpiperidin-1-ylcarbonyloxy)ethyl |
| 138 | CH₃ | Z | H | CH₂OH | (N-ethyl-N-isopentylcarbamoyloxy)methyl |
| 143 | H | Z | H | CH₂OH | Na |
| 144 | H | Z | H | CH₂OH | ethyl N,N-diisopropylcarbamate |
| 145 | CH₃ | Z | H | CH₂OH | H |
| 146 | CH₃ | Z | H | CH₂OH | K |
| 147 | CH₃ | E | H | CH₂OH | ethyl N,N-diisopropylcarbamate |

TABLE 8

| Example | structure |
|---|---|
| 139 | 5-bromo-4-(hydroxymethyl)thiazole |
| 140 | 5-(trimethylsilylethynyl)-4-(hydroxymethyl)thiazole |
| 141 | 5-ethynyl-4-(hydroxymethyl)thiazole |

TABLE 9

| Example | R¹ | E/Z | R^p | R^q | R⁴ |
|---|---|---|---|---|---|
| 44 | CH₃ | Z | H | CH₂OH | Na |
| 65 | CH₃ | Z | H | CONH₂ | Na |
| 66 | CH₃ | Z | H | CONH(CH₂)₂OH | Na |
| 67 | CH₃ | Z | H | CON(CH₃)₂ | Na |
| 68 | CH₃ | Z | H | CONHCH₃ | Na |
| 69 | CH₃ | Z | H | CONHCH₂CN | Na |
| 70 | CH₃ | Z | H | CON(CH₃)CH₂CN | Na |
| 71 | CH₃ | Z | H | CH₂CN | Na |

TABLE 9-continued

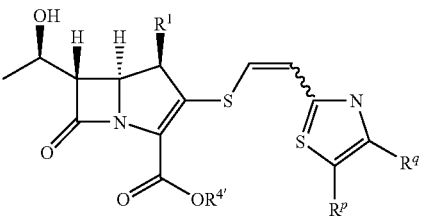

| Example | R¹ | E/Z | R^p | R^q | R⁴ |
|---------|-----|-----|-----|-----|-----|
| 72 | CH₃ | Z | H | (N-acetyl-azetidin-3-ol) | Na |
| 73 | CH₃ | Z | H | (N-acetyl-azetidine-3-CN) | Na |
| 74 | CH₃ | Z | CH₂OH | H | Na |
| 75 | CH₃ | Z | CONH₂ | CONH₂ | Na |
| 83 | CH₃ | Z | H | CH₂OH | (cyclohexyl carbonate group) |
| 88 | CH₃ | Z | H | CONH(CH₂)₂OH | (cyclohexyl carbonate group) |

TABLE 10

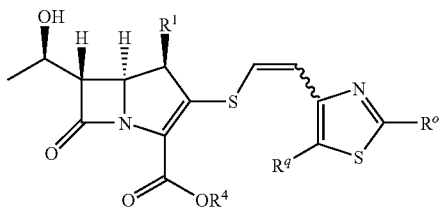

| Example | R¹ | E/Z | R° | R^q | R⁴ |
|---------|-----|-----|-----|-----|-----|
| 76 | CH₃ | Z | H | H | Na |
| 77 | CH₃ | Z | CONH₂ | H | Na |
| 78 | CH₃ | Z | H | CH₂OH | Na |

Test Example 1

Antimicrobial Activity

The minimum inhibitory concentrations (MIC, μg/ml) of representative compounds, among the novel carbapenem derivatives of the present invention, to various pathogenic bacteria were measured in accordance with the method described in CHEMOTHERAPY, vol. 16, No. 1, 99, 1968. The results are shown in Table 11. The culture medium for the measurement is Sensitivity Disk agar-N+5% Horse blood, and the amount of inoculants used is $10^6$ CFU/ml.

IPM (imipenem) was used as a comparative substance.

TABLE 11

| Example No. | 41 | 61 | 43 | 44 | 78 | IPM |
|-------------|-----|-----|-----|-----|-----|-----|
| S. aureus 209P JC-1 | 0.031 | 0.063 | 0.063 | 0.031 | 0.031 | 0.016 |
| S. pneumoniae R6 | 0.008 | 0.031 | 0.008 | 0.008 | 0.008 | 0.008 |
| S. pneumoniae 197 | 0.125 | 1 | 0.125 | 0.25 | 0.25 | 1 |
| S. pneumoniae PRC53 | 0.063 | 0.25 | 0.063 | 0.063 | 0.063 | 0.125 |
| E. coli W4680 | 1 | 8 | 4 | 4 | 8 | 0.125 |
| K. pneumoniae GN69 | 0.5 | 8 | 4 | 4 | 8 | 0.125 |
| M. catarrhalis W-500 | 0.063 | 0.063 | 0.125 | 0.063 | 0.25 | 0.063 |
| H. influenzae Rd | 0.031 | 0.031 | 0.031 | 0.031 | 0.031 | 1 |
| H. influenzae 870 | 0.125 | 0.125 | 0.25 | 0.125 | 0.125 | 4 |
| H. influenzae PRC44 | 0.125 | 0.125 | 0.125 | 0.063 | 0.063 | 16 |

The invention claimed is:

1. A compound of formula (III) or a pharmaceutically acceptable salt thereof:

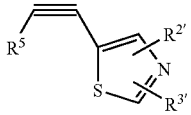
(III)

wherein
one of $R^{2'}$ and $R^{3'}$ represents
hydroxy lower alkyl,
hydroxy lower alkyl protected by a protective group of hydroxyl,
lower alkoxy-lower alkyl, or
lower alkoxycarbonyl, and
the other represents a hydrogen atom, and
$R^5$ represents a hydrogen atom or a protective group of alkynyl.

2. The compound or pharmaceutically acceptable salt thereof according to claim 1, wherein, in formula (III), one of $R^{2'}$ and $R^{3'}$ represents
hydroxymethyl,
acetoxymethyl,
methoxycarbonyl, or
ethoxycarbonyl, and
the other represents a hydrogen atom.

3. A compound of formula (IV) or a pharmaceutically acceptable salt thereof:

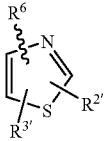
(IV)

wherein
$R^{2'}$ and $R^{3'}$, which may be the same or different, each represent
a hydrogen atom,
a halogen atom,
amino,
substituted amino,
hydroxy lower alkyl,
cyano lower alkyl,
lower alkoxy-lower alkyl,
substituted lower alkoxy-lower alkyl,
lower alkoxy-lower alkoxy-lower alkyl,
substituted lower alkoxy-lower alkoxy-lower alkyl,
acyloxy lower alkyl,
substituted acyloxy lower alkyl,
carbamoyl,
mono-lower alkylcarbamoyl,
substituted mono-lower alkylcarbamoyl,
di-lower alkylcarbamoyl,
substituted di-lower alkylcarbamoyl,
lower alkoxycarbonyl,
azetidinylcarbonyl, or
substituted azetidinylcarbonyl, and
$R^6$ represents $R^7$—S—C≡C— wherein $R^7$ represents a hydrogen atom, a metal ion, or a protective group of thiol.

4. The compound or pharmaceutically acceptable salt thereof according to claim 3, wherein, in formula (IV), one of $R^{2'}$ and $R^{3'}$ represents
hydroxy lower alkyl,
hydroxy lower alkyl protected by a protective group of hydroxyl,
lower alkoxy-lower alkyl, or
lower alkoxycarbonyl, and
the other represents a hydrogen atom.

5. The compound or pharmaceutically acceptable salt thereof according to claim 4, wherein, in formula (IV), one of $R^{2'}$ and $R^{3'}$ represents
hydroxymethyl,
acetoxymethyl,
methoxycarbonyl, or
ethoxycarbonyl, and
the other represents a hydrogen atom.

6. The compound or pharmaceutically acceptable salt thereof according to claim 3, wherein $R^6$ is present at the 5-position on the thiazole ring in formula (IV).

* * * * *